US006753411B2

(12) United States Patent
Baumann et al.

(10) Patent No.: US 6,753,411 B2
(45) Date of Patent: Jun. 22, 2004

(54) PROTECTION-OF-TELOMERE-1 (POT-1) PROTEINS

(75) Inventors: Peter Baumann, Boulder, CO (US); Thomas R. Cech, Potomac, MD (US)

(73) Assignee: The Regents of the University of Colorado, Colorado ( * ) Notice: Subject to any disclaimer, the term of this patent is extended or adjusted under 35 U.S.C. 154(b) by 0 days.

(21) Appl. No.: 09/816,248

(22) Filed: Mar. 26, 2001

(65) Prior Publication Data

US 2002/0137703 A1 Sep. 26, 2002

(51) Int. Cl.[7] .................. C07K 14/435; C07H 21/04
(52) U.S. Cl. ............... 530/350; 435/193; 536/23.1; 536/23.5
(58) Field of Search .................. 530/350; 435/193; 536/23.1, 23.5

(56) References Cited

U.S. PATENT DOCUMENTS

| | | | |
|---|---|---|---|
| 6,046,307 A | 4/2000 | Shay et al. | 530/324 |
| 6,054,442 A | 4/2000 | Chen et al. | 514/45 |
| 6,110,955 A | 8/2000 | Nudelman et al. | 514/411 |
| 6,156,763 A | 12/2000 | Kerwin et al. | 514/279 |
| 6,194,206 B1 | 2/2001 | West et al. | 435/375 |
| 6,312,922 B1 * | 11/2001 | Edwards et al. | 435/69.1 |

OTHER PUBLICATIONS

Isogai et al, NCBI Database, National Center for Biotechnology Information, National Library of Medicine, NIH (Bethesda, MD, USA). Accession No. BAB14110, Sep. 29, 2000.*
Isogai et al. NCBI Database, National Center for Biotechnology Information, National Library of Medicine, NIH (Bethesda, MD, USA). Accession No. AK022580, Sep. 29, 2000.*
Isogai et al. NCBI Database, National Center for Biotechnology Information, National Library of Medicine, NIH (Bethesda, MD, USA). Accession No. BAA1988, Feb. 22, 2000.*
Isogai et al. NCBI Database, National Center for Biotechnology Information, National Library of Medicine, NIH (Bethesda, MD, USA). Accession No. AK001935, Feb. 22, 2000.*
Isogai et al. National Center for Biotechnology Information, National Library of Medicine, NIH (Bethesda, MD, USA), Accession No. BAA91568, Feb. 22, 2000.*
J.P. Cooper, "Telomere Transitions in Yeast: The End of the Chromosome As We Know It", *Genetics & Development*, Apr. 2000, pp. 169–177; @ 2000 Elsevier Science Ltd.
McEachern et al., "Telomeres and Their Control", *Annu. Rev. Genet. 2000*, vol. 34, pp. 331–358; Annual Reviews.
C.M. Price, "Telomeres and Telomerase: Broad Effects on Cell Growth ", *Genetics & Development*, Apr. 1999, vol. 9, No. 2, pp. 218–224; Elsevier Science Ltd.

Bodnar et al., "Extension of Life–Span by Introduction of Telomerase into Normal Human Cells", *Science*, Jan. 1998, vol. 279, pp. 349–352.
Gottschling et al., Telomere Proteins: Specific Recognition and Protection of the Natural Termini of Oxytricha Macronuclear DNA, *Cell*, Oct. 1986, vol. 47, No. 2, pp. 195–205;Cell Press; Cell Press.
C. M. Price, "Telomeric DNA–protein Interactions of Oxytricha Macronuclear DNA", *Gene & Development*, Oct. 1987, vol. 1, No. 8, pp. 783–793, Cold Spring Harbor Laboratory.
Horvath, "Crystal Structure of the Oxytricha nova Telomere End Binding Protein Complexed with Single Strand DNA", *Cell*, Dec. 1998, vol. 95, pp. 963–974, Cell Press.
G. Fang et al., "Oxytricha Telomere–binding Protein: Separable DNA–binding and Dimerization Domains of the α–subunit", *Genes & Development*, May 1993, vol. 7, No. 5, pp. 870–882, Cold Spring Harbor Lab.
Froelich–Ammon et al., "Modulation of Telomerase Activity by Telomere DNA–binding Proteins in Oxytricha", *Genes & Development*, 1998, vol. 12, pp. 1504–1514, Cold Spring Harbor Laboratory.
Makarov et al., "Long G Tails at Both Ends of Human Chromosomes Suggest a C Strand Degradation Mechanism for Telomere Shortening", *Cell*, Mar. 1997, vol. 88, pp. 657–666, Cell Press.
Haering et al., "Analysis of Telomerase Catalytic Subunit Mutants in vivo and vitro in Schizosaccharomyces Pombe", *PNAS*, Jun. 2000, vol. 97, No. 12, pp. 6367–6372.
Baumann et al., "Protection of Telomeres by the KU Protein in Fission Yeast ", *Molecular Biology of the Cell*, Oct. 2000, vol. 11, pp. 3265–3275, The American Society for Cell Biology.
Nakamura et al., "Two Modes of Survival of Fission Yeast Without Telomerase", *Science*, Oct. 1998 vol. 282, pp. 493–496, Am. Assoc. for the Advancement of Science.
Aigner et al., "Euplotes Telomerase Contains an La Motif Protein Produced by Apparent Translational Frameshifting", *The EMBO Journal*, 2000, vol. 19, No. 22, pp. 6230–6239: European Molecular Biology Org.
Rosenberg et al., "Grafting Genetically Modified Cells to the Damaged Brain: Restorative Effects of NGF Expression", *Science*, Dec. 1988, vol. 242, pp. 1575–1578.

(List continued on next page.)

*Primary Examiner*—Carla J. Myers
(74) *Attorney, Agent, or Firm*—Foley & Lardner LLP

(57) ABSTRACT

A protein identified in humans and *Schizosaccharomyces pombe*, Pot1p, binds single-stranded telomeric DNA and both stabilizes chromosome ends and regulates telomerase activity. Compounds that stabilize or disrupt the Pot1p-DNA interaction will be useful in regulating the telomere length of a cell. Because telomere length is involved in the regulation of cellular life-span, the life-span of useful cell populations may be prolonged or undesirable cells may be caused to cease proliferation. The identification of a Pot1 protein and its encoding DNA provides methods of screening useful compounds or diagnosing illnesses that involve altered expression or structure of a Pot1 protein or gene.

4 Claims, 24 Drawing Sheets

OTHER PUBLICATIONS

Wolff et al., "Grafting Fibroblasts Genetically Modified to Produce L–Dopa in a Rat Model of Parkinson Disease", *Proc. Natl. Acad. Sci.*, Nov. 1989, vol. 86, pp. 9011–9014, NAS.

C.P. Hodgson, "The Vector Void in Gene Therapy", *Bio/Technology*, Mar. 1995, vol. 13, pp. 222–225, Nature.

Caplen et al., Liposome–Mediated CFTR Gene Transfer to the Nasal Epithelium of Patients with Cystic Fibrosis, *Nautre Medicine*, Jan. 1995, vol. 1, No. 1, pp. 39–46.

Zhu et al., "Systemic Gene Expression After Intravenous DNA Delivery into Adult Mice", *Science*, Jul. 1993, vol. 261, pp. 209–211, Am. Assoc. for the Advancement of Science.

K. L. Berkener, "Development of Adenovirus Vectors for the Expression of Heterologous Genes", *Bio Techniques*, 1988, vol. 6, No. 7, pp. 616–629, Journal of Laboratory Technology.

B. C. Trapnell,, "Adenoviral Vectors for Gene Transfer", *Advanced Drug Delivery Reviews*, Dec. 1993, vol. 12, Issue 3, 185–199, Elsevier Science Publishers.

K. Jones et al., The Sequence of *Homo Sapiens* PAC Clone RP5–907C10. Dec. 21, 1999.

International Search Report dated Apr. 15, 2003, issued for PCT application No. PCT/US02/11107.

ISOGA et al., "Nedo human cDNA sequencing project." Gene Sequence, Feb 22, 2000. NCB1 Database, National Center for Biotechnology Information, National Library of Medicine, NIH (Bethesda, MD, USA). Accession No. BAA91568.

* cited by examiner

FIGURE 7

```
                                         tatgagtgaa gttccatcca  13020
tgatgcaaaa agccatgctg tcaaccttaa aaagtatatc ggccattccc gatgatgtac  13080
cccctcctta ttctgagttt gctgatgata cgacagcgca agctggttct agtaaaagag  13140
atagcgctat atctgaagat cccgatcatc acaaaagtgt ttggtggtct ttgagatggc  13200
aatctcggct tgttggtcgt ggaaaatcta ctgctcttac tcctgaagaa accagagcaa  13260
tacaggagca ggcaaagaca ctgaaaaagg caggaatgga ctttatgcta ttctctttct  13320
ggttacctgc cctacttttg ctgagtatgt ttggtcttcg aagctatgct caaatgatcg  13380
ggggatattt atatcgctgc ataattggca tttaggtttg acgaacaacc atgcatgttt  13440
ttttctttct tttagtttta ttctttttg tagattatga gcaaactact gtcaaaactt  13500
aggtattatg acaatgaaat cgtatatatt atattcgatt ggatcaattt tttattatat  13560
tgaaagtaat tgcttatttt gtaagttaaa cttacatggg tttaaacgca tagagcaggt  13620
tggcgctttt aaaaccaaaa tagatcgttg caggtttgct gttctggatc gtgaatgcaa  13680
taccttagga aagtctttta ataagctatc gcttttttgca ttgcattctt tttctaaact  13740
gaacgttaga ttagctaaag taagcgtctt gagttttcga gatgaaccgc atacattaaa  13800
atttttaagt accaattggc atgaaccggt atgcgatctg cttattataa tactagtaaa  13860
tcttgatact cggcaaactc tttcaataat agcctagcag aaactgggat atgtctaaag  13920
ttttacaact gcgctcagct taaggactt acggcgatcc atttaatagc tagccatgaa  13980
cactcataac ctcaagattg aggagtgggt cattcttttg cttgataaag aaacaaattc  14040
attattggta aaataaaact gaataaccct tagttcatcc taggaatttg aagaagggga  14100
atgatcaagc ttgaacaagt aactctcacg cagtctattg aataatctga aggttcatca  14160
cttttcaaggg gttgtcttgg tttaaaaagc ttttaccaat tccatttagg tttctgagaa  14220
aggctaaaac tcatttgttg ttcttaaagg atatttggat cattcgttga tcaagcatgg  14280
gagaggacgt tattgacagt cttcagttga atgagttatt aaatgctgga gaatataaga  14340
ttggagtgag atatcaatgg atttatattt gttttgctaa caatgaaaaa ggaacttaca  14400
tttcagtcca ttagaagctc tcaagaatta caaaagaaga atactattgt caatttgttt  14460
ggaatagtaa aagatttac ccctagtcgc caagtctac atggaactaa gggtatgctt  14520
gcttatcatg gtggaaacta tactttttat ttttccagtc aagagctaat aatcatgttt  14580
ttagattggg taaccaccgt atatttgtgg gatccaacat gtgatacatc aagcatcgga  14640
ctacagatac acttgttcag caaacaggga aatgatttgc ctgtaatcaa gcaggtgggg  14700
caaccgcttt tgcttcatca aatcacatta agaagttata gagacaggac tcaaggtttg  14760
tctaaggatc aatttcgata tgcacttttgg ccagactttt cttctaattc caaagatact  14820
ctctgtcctc aaccaatgcc tcgtttaatg aaaacgggag acaaggaaga gcaattcgcc  14880
ttgttgttaa ataaaatttg ggatgagcaa actaataaac ataaaaatgg cgaattattg  14940
agtacctctt ctgctcgtca aaatcaaact ggattgagtt acccttctgt ctcttttct  15000
ctgctatcac aaataactcc acatcaacgt tgtagctttt acgctcaggt aattaaaact  15060
tggtacagtg ataaaaactt tactcttat gtcactgatt atacgaaaaa tgagctttt  15120
tttccaatgt ctccgtatac tagctcctcg agatggaggg gcccttttgg tcggttttct  15180
ataaggtgca ttttatggga tgagcacgac ttttactgcc gcaactacat taaagaaggt  15240
gactatgtgg ttatgaaaaa tgtgcgaacc aaaattgatc accttggtta tctggaatgt  15300
atacttcatg gggattcagc aaaatcgttat acatatgagta tagaaaaagt cgattcggaa  15360
gaacccgaac taaacgaaat taagtcacgt aaaaggcttt atgttcagaa ttgccaaaat  15420
ggtatagaag cagtaatcga gaaactcagt caaagccaac aatcggaaaa tccttttatc  15480
gcccatgaat taaagcaaac ttctgttaat gaaattacgg cccatgtcat aaatgaacct  15540
gctagtttaa aattgactac tatttctacc atacttcatg caccctttgca gaatcttctc  15600
aaaccgagga aacataggct acgcgttcag gtggtagatt tttggccaaa gagtttgacg  15660
cagtttgctg tgctatctca accaccatct tcgtatgttt ggatgtttgc cttgctcgta  15720
agggatgtat cgaatgtgac tttaccggtc atatttttg attctgacgc tgcggaactt  15780
attaacagct caaaaatcca accttgcaat ttagctgatc acccgcagat gactcttcag  15840
cttaaagaaa gattatttct gatttggggg aacttggaag aacgcattca gcatcacata  15900
tcgaagggtg aatcgccaac tctggctgct gaagatgtta aaaccaccatg gtttgatata  15960
tatgtcaaag aatacattcc tgtaattggg aacaccaaag accatcaatc tttgactttt  16020
cttcagaagc gctggcgagg atttggcacg aaaattgttt gactattgtg atacaaaact  16080
tacaataatg aaatgcttac ggaaaagaaa cataagaaaa acaatattta aatttaagga  16140
aagctctata ttgggagaat tttataaagc gagcgaattt gtactaagga aaaacacaga  16200
ggggaaacgt gaaatatcta attgcttaga ctttatataa catcaacttc gaaataatct  16260
tagaaattaa ttcaaaaat aataaggatt ggtttgatgt atggtggtta catctaagca  16320
ggcttttgct tagaagttgc aagtgttgag gcatcatcat cactttcatc gtcaacagcg  16380
aatagagctt gatgctcatc ggcactgcca tgaataatat gagggttggc tggagatgta  16440
ggacgctcat gatgcagatg caaactatca tttgagagag aggaagtcat ctcaaactca  16500
tctacatctt gagcaacttg ctcactcatt gcgaaacgac ggttattctc ggtaggacgc  16560
cacaagtaca aaatggtaag catcaagatc aaaacaagaa tatcagtgta tccgtaatta  16620
aggaaccaaa gaagtttcca gtattttaag taatagttca tttgaccgta gataccaatc  16680
aaaatggcat tggctgcgac aatcgaagca taagcgacaa tgccaaaaca tataacaatc  16740
caaagacgag tatacatctg agccttaaca gtttgcttac gaatacggag atcacgactt  16800
gtattattta aagccaatac aatccaaagg aacatagcga agagggtgat taaaaagaca  16860
ggagcggcaa acaaaatgac caaagactct ttattagatg ggctaatgaa caaagatgac  16920
aagaaaaagc atgaagaaac gaactgcaaa ccagcaagaa tttgacactt acgaagaaga  16980
```

FIGURE 8A gattgaggagtgggtcattctttttgcttgataaagaaacaaattcattattggtaaaataaaactgaataaccccttagttcatcctaggaatttgaagaagggg
aatgatcaagcttgaacaagtaactctcacgcagtctattgaataatctgaaggttcatcactttcaagggggttgtcttggtttaaaaagcttttaccaattcca
tttaggttctgagaaaggctaaaactcatttgttgttcttaaaggatatttggatcattcgttgatcaagcATGGGAGAGGACGTTATTGA
CAGTCTTCAGTTGAATGAGTTATTAAATGCTGGAGAATATAAGATTGGAGAACTTACATTT
CAGTCCATTAGAAGCTCTCAAGAATTACAAAAGAAGAATACTATTGTCAATTTGTTTGGAA
TAGTAAAAGATTTTACCCCTAGTCGCCAAAGTCTACATGGAACTAAGGATTGGGTAACCA
CCGTATATTTGTGGGATCCAACATGTGATACATCAAGCATCGGACTACAGATACACTTGTT
CAGCAAACAGGGAAATGATTTGCCTGTAATCAAGCAGGTGGGGCAACCGCTTTTGCTTCA
TCAAATCACATTAAGAAGTTATAGAGACAGGACTCAAGGTTTGTCTAAGGATCAATTTCGA
TATGCACTTTGGCCAGACTTTTCTTCTAATTCCAAAGATACTCTCTGTCCTCAACCAATGCC
TCGTTTAATGAAAACGGGAGACAAGGAAGAGCAATTCGCCTTGTTGTTAAATAAAATTTG
GGATGAGCAAACTAATAAACATAAAAATGGCGAATTATTGAGTACCTCTTCTGCTCGTCAA
AATCAAACTGGATTGAGTTACCCTTCTGTCTCTTTTTCTCTGCTATCACAAATAACTCCACA
TCAACGTTGTAGCTTTTACGCTCAGGTAATTAAAACTTGGTACAGTGATAAAAACTTTACT
CTTTATGTCACTGATTATACGGAAAATGAGCTTTTTTTTCCAATGTCTCCGTATACTAGCTC
CTCGAGATGGAGGGGCCCTTTTGGTCGGTTTTCTATAAGGTGCATTTTATGGGATGAGCAC
GACTTTTACTGCCGCAACTACATTAAAGAAGGTGACTATGTGGTTATGAAAAATGTGCGAA
CCAAAATTGATCACCTTGGTTATCTGGAATGTATACTTCATGGGGATTCAGCAAAACGTTA
TAATATGAGTATAGAAAAAGTCGATTCGGAAGAACCCGAACTAAACGAAATTAAGTCACG
TAAAAGGCTTTATGTTCAGAATTGCCAAAATGGTATAGAAGCAGTAATCGAGAAACTCAG
TCAAAGCCAACAATCGGAAAATCCTTTTATCGCCCATGAATTAAAGCAAACTTCTGTTAAT
GAAATTACGGCCCATGTCATAAATGAACCTGCTAGTTTAAAATTGACTACTATTTCTACCA
TACTTCATGCACCTTTGCAGAATCTTCTCAAACCGAGGAAACATAGGCTACGCGTTCAGGT
GGTAGATTTTTGGCCAAAGAGTTTGACGCAGTTTGCTGTGCTATCTCAACCACCATCTTCG
TATGTTTGGATGTTTGCCTTGCTCGTAAGGGATGTATCGAATGTGACTTTACCGGTCATATT
TTTTGATTCTGACGCTGCGGAACTTATTAACAGCTCAAAAATCCAACCTTGCAATTTAGCT
GATCACCCGCAGATGACTCTTCAGCTTAAAGAAAGATTATTTCTGATTTGGGGGAACTTGG
AAGAACGCATTCAGCATCACATATCGAAGGGTGAATCGCCAACTCTGGCTGCTGAAGATG
TTGAAACACCATGGTTTGATATATATGTCAAAGAATACATTCCTGTAATTGGGAACACCAA
AGACCATCAATCTTTGACTTTTCTTCAGAAGCGCTGGCGAGGATTTGGCACGAAAATTGTT
TGActattgtgatacaaaacttacaataatgaaatgcttacggaaaagaaacataagaaaaacaatatttaaatttaaggaaagctctatattgggagaat
tttataaagcgagcgaatttgtactaaggaaaaacacaga

FIGURE 8B

MGEDVIDSLQLNELLNAGEYKIGELTFQSIRSSQELQKKNTIVNLFGIV
KDFTPSRQSLHGTKDWVTTVYLWDPTCDTSSIGLQIHLFSKQGNDLPVI
KQVGQPLLLHQITLRSYRDRTQGLSKDQFRYALWPDFSSNSKDTLCPQP
MPRLMKTGDKEEQFALLLNKIWDEQTNKHKNGELLSTSSARQNQTGLSY
PSVSFSLLSQITPHQRCSFYAQVIKTWYSDKNFTLYVTDYTENELFFPM
SPYTSSSRWRGPFGRFSIRCILWDEHDFYCRNYIKEGDYVVMKNVRTKI
DHLGYLECILHGDSAKRYNMSIEKVDSEEPELNEIKSRKRLYVQNCQNG
IEAVIEKLSQSQQSENPFIAHELKQTSVNEITAHVINEPASLKLTTIST
ILHAPLQNLLKPRKHRLRVQVVDFWPKSLTQFAVLSQPPSSYVWMFALL
VRDVSNVTLPVIFFDSDAAELINSSKIQPCNLADHPQMTLQLKERLFLI
WGNLEERIQHHISKGESPTLAAEDVETPWFDIYVKEYIPVIGNTKDHQS
LTFLQKRWRGFGTKIV

FIGURE 8C

ATGGGAGAGGACGTTATTGACAGTCTTCAGTTGAATGAGTTATTAAATGCTGGAGAATATA
AGATTGGAGAACTTACATTTCAGTCCATTAGAAGCTCTCAAGAATTACAAAAGAAGAATA
CTATTGTCAATTTGTTTGGAATAGTAAAAGATTTTACCCCTAGTCGCCAAAGTCTACATGG
AACTAAGGgtatgcttgcttatcatggtggaaactatactttttattttccagtcaagagctaataatcatgtttttagATTGGGTAACCAC
CGTATATTTGTGGGATCCAACATGTGATACATCAAGCATCGGACTACAGATACACTTGTTC
AGCAAACAGGGAAATGATTTGCCTGTAATCAAGCAGGTGGGGCAACCGCTTTTGCTTCAT
CAAATCACATTAAGAAGTTATAGAGACAGGACTCAAGGTTTGTCTAAGGATCAATTTCGAT
ATGCACTTTGGCCAGACTTTTCTTCTAATTCCAAAGATACTCTCTGTCCTCAACCAATGCCT
CGTTTAATGAAAACGGGAGACAAGGAAGAGCAATTCGCCTTGTTGTTAAATAAAATTTGG
GATGAGCAAACTAATAAACATAAAAATGGCGAATTATTGAGTACCTCTTCTGCTCGTCAAA
ATCAAACTGGATTGAGTTACCCTTCTGTCTCTTTTTCTCTGCTATCACAAATAACTCCACAT
CAACGTTGTAGCTTTTACGCTCAGGTAATTAAAACTTGGTACAGTGATAAAAACTTTACTC
TTTATGTCACTGATTATACGGAAAATGAGCTTTTTTTTCCAATGTCTCCGTATACTAGCTCC
TCGAGATGGAGGGGCCCTTTTGGTCGGTTTTCTATAAGGTGCATTTTATGGGATGAGCACG
ACTTTTACTGCCGCAACTACATTAAAGAAGGTGACTATGTGGTTATGAAAAATGTGCGAAC
CAAAATTGATCACCTTGGTTATCTGGAATGTATACTTCATGGGGATTCAGCAAAACGTTAT
AATATGAGTATAGAAAAAGTCGATTCGGAAGAACCCGAACTAAACGAAATTAAGTCACGT
AAAAGGCTTTATGTTCAGAATTGCCAAAATGGTATAGAAGCAGTAATCGAGAAACTCAGT
CAAAGCCAACAATCGGAAAATCCTTTTATCGCCCATGAATTAAAGCAAACTTCTGTTAATG
AAATTACGGCCCATGTCATAAATGAACCTGCTAGTTTAAAATTGACTACTATTTCTACCAT
ACTTCATGCACCTTTGCAGAATCTTCTCAAACCGAGGAAACATAGGCTACGCGTTCAGGTG
GTAGATTTTTGGCCAAAGAGTTTGACGCAGTTTGCTGTGCTATCTCAACCACCATCTTCGT
ATGTTTGGATGTTTGCCTTGCTCGTAAGGGATGTATCGAATGTGACTTTACCGGTCATATTT
TTTGATTCTGACGCTGCGGAACTTATTAACAGCTCAAAAATCCAACCTTGCAATTTAGCTG
ATCACCCGCAGATGACTCTTCAGCTTAAAGAAAGATTATTTCTGATTTGGGGGAACTTGGA
AGAACGCATTCAGCATCACATATCGAAGGGTGAATCGCCAACTCTGGCTGCTGAAGATGT
TGAAACACCATGGTTTGATATATATGTCAAAGAATACATTCCTGTAATTGGGAACACCAAA
GACCATCAATCTTTGACTTTTCTTCAGAAGCGCTGGCGAGGATTTGGCACGAAAATTGTTT
GA

FIGURE 8D

MGEDVIDSLQLNELLNAGEYKIGELTFQSIRSSQELQKKNTIVNLFGIV
KDFTPSRQSLHGTKGMLAYHGGNYTFYFSSQELIIMFLDWVTTVYLWDP
TCDTSSIGLQIHLFSKQGNDLPVIKQVGQPLLLHQITLRSYRDRTQGLS
KDQFRYALWPDFSSNSKDTLCPQPMPRLMKTGDKEEQFALLLNKIWDEQ
TNKHKNGELLSTSSARQNQTGLSYPSVSFSLLSQITPHQRCSFYAQVIK
TWYSDKNFTLYVTDYTENELFFPMSPYTSSSRWRGPFGRFSIRCILWDE
HDFYCRNYIKEGDYVVMKNVRTKIDHLGYLECILHGDSAKRYNMSIEKV
DSEEPELNEIKSRKRLYVQNCQNGIEAVIEKLSQSQQSENPFIAHELKQ
TSVNEITAHVINEPASLKLTTISTILHAPLQNLLKPRKHRLRVQVVDFW
PKSLTQFAVLSQPPSSYVWMFALLVRDVSNVTLPVIFFDSDAAELINSS
KIQPCNLADHPQMTLQLKERLFLIWGNLEERIQHHISKGESPTLAAEDV
ETPWFDIYVKEYIPVIGNTKDHQSLTFLQKRWRGFGTKIV

FIGURE 9A

```
ATGTCTTTGGTTCCAGCAACAAATTATATATATACACCCCTGAATCAACTTAAGGGTGGTA
CAATTGTCAATGTCTATGGTGTTGTGAAGTTCTTTAAGCCCCCATATCTAAGCAAAGGAAC
TGATTATTGCTCAGTTGTAACTATTGTGGACCAGACAAATGTAAAACTAACTTGCCTGCTC
TTTAGTGGAAACTATGAAGCCCTTCCAATAATTTATAAAAATGGAGATATTGTTCGCTTTC
ACAGGCTGAAGATTCAAGTATATAAAAAGGAGACTCAGGGTATCACCAGCTCTGGCTTTG
CATCTTTGACGTTTGAGGGAACTTTGGGAGCCCCTATCATACCTCGCACTTCAAGCAAGTA
TTTTAACTTCACTACTGAGGACCACAAAATGGTAGAAGCCTTACGTGTTTGGGCATCTACT
CATATGTCACCGTCTTGGACATTACTAAAATTGTGTGATGTTCAGCCAATGCAGTATTTTG
ACCTGACTTGTCAGCTCTTGGGCAAAGCAGAAGTGGACGGAGCATCATTTCTTCTAAAGGT
ATGGGATGGCACCAGGACACCATTTCCATCTTGGAGAGTCTTAATACAAGACCTTGTTCTT
GAAGGTGATTTAAGTCACATCCATCGGCTACAAAATCTGACAATAGACATTTTAGTCTACG
ATAACCATGTTCATGTGGCAAGATCTCTGAAGGTTGGAAGCTTTCTTAGAATCTATAGCCT
TCATACCAAACTTCAATCAATGAATTCAGAGAATCAGACAATGTTAAGTTTAGAGTTTCAT
CTTCATGGAGGTACCAGTTACGGTCGGGGAATCAGGGTCTTGCCAGAAAGTAACTCTGAT
GTGGATCAACTGAAAAAGGATTTAGAATCTGCAAATTTGACAGCCAATCAGCATTCAGAT
GTTATCTGTCAATCAGAACCTGACGACAGCTTTCCAAGCTCTGGATCAGTATCATTATACG
AGGTAGAAAGATGTCAACAGCTATCTGCTACAATACTTACAGATCATCAGTATTTGGAGA
GGACACCACTATGTGCCATTTTGAAACAAAAAGCTCCTCAACAATACCGCATCCGAGCAA
AATTGAGGTCATATAAGCCCAGAAGACTATTTCAGTCTGTTAAACTTCATTGCCCTAAATG
TCATTTGCTGCAAGAAGTTCCACATGAGGGCGATTTGGATATAATTTTTCAGGATGGTGCA
ACTAAAACCCCAGTTGTCAAGTTACAAAATACATCATTATATGATTCAAAAATCTGGACCA
CTAAAAATCAAAAAGGACGAAAAGTAGCAGTTCATTTTGTGAAAAATAATGGTATTCTCC
CGCTTTCAAATGAATGTCTACTTTTGATAGAAGGAGGTACACTCAGTGAAATTTGCAAACT
CTCGAACAAGTTTAATAGTGTAATTCCTGTGAGATCTGGCCACGAAGACCTGGAACTTTTG
GACCTTTCAGCACCATTTCTTATACAAGGAACAATACATCACTATGGATGTAAACAGTGTT
CTAGTTTGAGATCCATACAAAATCTAAATTCCCTGGTTGATAAAACATCGTGGATTCCTTC
TTCTGTGGCAGAAGCACTGGGTATTGTACCCCTCCAATATGTGTTTGTTATGACCTTTACA
CTTGATGATGGAACAGGAGTACTAGAAGCCTATCTCATGGATTCTGACAAATTCTTCCAGA
TTCCAGCATCAGAAGTTCTGATGGATGATGACCTTCAGAAAAGTGTGGATATGATCATGGA
TATGTTTTGTCCTCCAGGAATAAAAATTGATGCATATCCGTGGTTGGAATGCTTCATCAAG
TCATACAATGTCACAAATGGAACAGATAATCAAATTTGCTATCAGATTTTTGACACCACAG
TTGCAGAAGATGTAATCTAA
```

FIGURE 9B

```
MSLVPATNYIYTPLNQLKGGTIVNVYGVVKFFKPPYLSKGTDYCSVVTI
VDQTNVKLTCLLFSGNYEALPIIYKNGDIVRFHRLKIQVYKKETQGITS
SGFASLTFEGTLGAPIIPRTSSKYFNFTTEDHKMVEALRVWASTHMSPS
WTLLKLCDVQPMQYFDLTCQLLGKAEVDGASFLLKVWDGTRTPFPSWRV
LIQDLVLEGDLSHIHRLQNLTIDILVYDNHVHVARSLKVGSFLRIYSLH
TKLQSMNSENQTMLSLEFHLHGGTSYGRGIRVLPESNSDVDQLKKDLES
ANLTANQHSDVICQSEPDDSFPSSGSVSLYEVERCQQLSATILTDHQYL
ERTPLCAILKQKAPQQYRIRAKLRSYKPRRLFQSVKLHCPKCHLLQEVP
HEGDLDIIFQDGATKTPVVKLQNTSLYDSKIWTTKNQKGRKVAVHFVKN
NGILPLSNECLLLIEGGTLSEICKLSNKFNSVIPVRSGHEDLELLDLSA
PFLIQGTIHHYGCKQCSSLRSIQNLNSLVDKTSWIPSSVAEALGIVPLQ
YVFVMTFTLDDGTGVLEAYLMDSDKFFQIPASEVLMDDDLQKSVDMIMD
MFCPPGIKIDAYPWLECFIKSYNVTNGTDNQICYQIFDTTVAEDVI
```

FIGURE 9C

ATGTCTTTGGTTCCAGCAACAAATTATATATATACACCCCTGAATCAACTTAAGGGTGGTA
CAATTGTCAATGTCTATGGTGTTGTGAAGTTCTTTAAGCCCCATATCTAAGCAAAGGAAC
TGATTATTGCTCAGTTGTAACTATTGTGGACCAGACAAATGTAAAACTAACTTGCCTGCTC
TTTAGTGGAAACTATGAAGCCCTTCCAATAATTTATAAAAATGGAGATATTGTTCGCTTTC
ACAGGCTGAAGATTCAAGTATATAAAAAGGAGACTCAGGGTATCACCAGCTCTGGCTTTG
CATCTTTGACGTTTGAGGGAACTTTGGGAGCCCCTATCATACCTCGCACTTCAAGCAAGTA
TTTTAACTTCACTACTGAGGACCACAAAATGGTAGAAGCCTTACGTGTTTGGGCATCTACT
CATATGTCACCGTCTTGGACATTACTAAAATTGTGTGATGTTCAGCCAATGCAGTATTTTG
ACCTGACTTGTCAGCTCTTGGGCAAAGCAGAAGTGGACGGAGCATCATTTCTTCTAAAGGT
ATGGGATGGCACCAGGACACCATTTCCATCTTGGAGAGTCTTAATACAAGACCTTGTTCTT
GAAGGTGATTTAAGTCACATCCATCGGCTACAAAATCTGACAATAGACATTTTAGTCTACG
ATAACCATGTTCATGTGGCAAGATCTCTGAAGGTTGGAAGCTTTCTTAGAATCTATAGCCT
TCATACCAAACTTCAATCAATGAATTCAGAGAATCAGACAATGTTAAGTTTAGAGTTTCAT
CTTCATGGAGGTACCAGTTACGGTCGGGGAATCAGGGTCTTGCCAGAAAGTAACTCTGAT
GTGGATCAACTGAAAAAGGATTTAGAATCTGCAAATTTGACAGCCAATCAGCATTCAGAT
GTTATCTGTCAATCAGAACCTGACGACAGCTTTCCAA<u>ATGGAGTCTCGCTTCGTCCTCCAG
GCTGGAGTTCAGTGGCACGGTCTCGGCTCATTGCAGCCTCCACCTCCTGAGTTCAAGCTTC
TCCTGCCTCAGCCTCCCAAGTAGCTGGGATTACAG</u>GCTCTGGATCAGTATCATTATACGAG
GTAGAAAGATGTCAACAGCTATCTGCTACAATACTTACAGATCATCAGTATTTGGAGAGG
ACACCACTATGTGCCATTTTGAAACAAAAAGCTCCTCAACAATACCGCATCCGAGCAAAA
TTGAGGTCATATAAGCCCAGAAGACTATTTCAGTCTGTTAAACTTCATTGCCCTAAATGTC
ATTTGCTGCAAGAAGTTCCACA

FIGURE 9D

```
MSLVPATNYIYTPLNQLKGGTIVNVYGVVKFFKPPYLSKGTDYCSVVTI
VDQTNVKLTCLLFSGNYEALPIIYKNGDIVRFHRLKIQVYKKETQGITS
SGFASLTFEGTLGAPIIPRTSSKYFNFTTEDHKMVEALRVWASTHMSPS
WTLLKLCDVQPMQYFDLTCQLLGKAEVDGASFLLKVWDGTRTPFPSWRV
LIQDLVLEGDLSHIHRLQNLTIDILVYDNHVHVARSLKVGSFLRIYSLH
TKLQSMNSENQTMLSLEFHLHGGTSYGRGIRVLPESNSDVDQLKKDLES
ANLTANQHSDVICQSEPDDSFPNGVSLRPPGWSSVARSRLIAASTS
```

FIGURE 9E

```
ATGTCTTTGGTTCCAGCAACAAATTATATATATACACCCCTGAATCAACTTAAGGGTGGTA
CAATTGTCAATGTCTATGGTGTTGTGAAGTTCTTTAAGCCCCCATATCTAAGCAAAGGAAC
TGATTATTGCTCAGTTGTAACTATTGTGGACCAGACAAATGTAAAACTAACTTGCCTGCTC
TTTAGTGGAAACTATGAAGCCCTTCCAATAATTTATAAAAATGGAGATATTGTTCGCTTTC
ACAGGCTGAAGATTCAAGTATATAAAAAGGAGACTCAGGGTATCACCAGCTCTGGCTTTG
CATCTTTGACGTTTGAGGGAACTTTGGGAGCCCCTATCATACCTCGCACTTCAAGCAAGTA
TTTTAACTTCACTACTGAGGACCACAAAATGGTAGAAGCCTTACGTGTTTGGGCATCTACT
CATATGTCACCGTCTTGGACATTACTAAAATTGTGTGATGTTCAGCCAATGCAGTATTTTG
ACCTGACTTGTCAGCTCTTGGGCAAAGCAGAAGTGGACGGAGCATCATTTCTTCTAAAGGT
ATGGGATGGCACCAGGACACCATTTCCATCTTGGAGAGTCTTAATACAAGACCTTGTTCTT
GAAGGTGATTTAAGTCACATCCATCGGCTACAAAATCTGACAATAGACATTTTAGTCTACG
ATAACCATGTTCATGTGGCAAGATCTCTGAAGGTTGGAAGCTTTCTTAGAATCTATAGCCT
TCATACCAAACTTCAATCAATGAATTCAGAGAATCAGACAATGTTAAGTTTAGAGTTTCAT
CTTCATGGAGGTACCAGTTACGGTCGGGGAATCAGGGTCTTGCCAGAAAGTAACTCTGAT
GTGGATCAACTGAAAAAGGATTTAGAATCTGCAAATTTGACAGCCAATCAGCATTCAGAT
GTTATCTGTCAATCAGAACCTGACGACAGCTTTCCAAGCTCTGGATCAGTATCATTATACG
AGGTAGAAAGATGTCAACAGCTATCTGCTACAATACTTACAGATCATCAGTATTTGGAGA
GGACACCACTATGTGCCATTTTGAAACAAAAAGCTCCTCAACAATACCGCATCCGAGCAA
AATTGAGGTCATATAAGCCCAGAAGACTATTTCAGTCTGTTAAACTTCATTGCCCTAAATG
TCATTTGCTGCAAGAAGTTCCACATGAGGGCGATTTGGATATAATTTTTCAGGATGGTGCA
ACTAAAACCCCAGATGTCAAGCTACAAAATACATCATTATATGATTCAAAAATCTGGACC
ACTAAAAATCAAAAAGGACGAAAAGTAGCAGTTCATTTTGTGAAAAATAATGGTATTCTC
CCGCTTTCAAATGAATGTCTACTTTTGATAGAAGGAGGTACACTCAGTGAAATTTGCAAAC
TCTCGAACAAGTTTAATAGTGTAATTCCTGTGAGATCTGGCCACGAAGACCTGGAACTTTT
GGACCTTTCAGCACCATTTCTTATACAAGGAACAATACATCACTATGGCACTGGGTATTGT
ACCCCTCCAATATGTGTTTGTTATGACCTTTACACTTGATGATGGAACAGGAGTACTAGAA
GCCTATCTCATGGATTCTGACAAATTCTTCCAGATTCCAGCATCAGAAGTTCTGATGGATG
ATGACCTTCAGAAAAGTGTGGATATGATCATGGATATGTTTTGTCCTCCAGGAATAAAAAT
TGATGCATATCCGTGGTTGGAATGCTTCATCAAGTCATACAATGTCACAAATGGAACAGAT
AATCAAATTTGCTATCAGATTTTTGACACCACAGTTGCAGAAGATGTAATCTAA
```

FIGURE 9F

```
MSLVPATNYIYTPLNQLKGGTIVNVYGVVKFFKPPYLSKGTDYCSVVTI
VDQTNVKLTCLLFSGNYEALPIIYKNGDIVRFHRLKIQVYKKETQGITS
SGFASLTFEGTLGAPIIPRTSSKYFNFTTEDHKMVEALRVWASTHMSPS
WTLLKLCDVQPMQYFDLTCQLLGKAEVDGASFLLKVWDGTRTPFPSWRV
LIQDLVLEGDLSHIHRLQNLTIDILVYDNHVHVARSLKVGSFLRIYSLH
TKLQSMNSENQTMLSLEFHLHGGTSYGRGIRVLPESNSDVDQLKKDLES
ANLTANQHSDVICQSEPDDSFPSSGSVSLYEVERCQQLSATILTDHQYL
ERTPLCAILKQKAPQQYRIRAKLRSYKPRRLFQSVKLHCPKCHLLQEVP
HEGDLDIIFQDGATKTPDVKLQNTSLYDSKIWTTKNQKGRKVAVHFVKN
NGILPLSNECLLLIEGGTLSEICKLSNKFNSVIPVRSGHEDLELLDLSA
PFLIQGTIHHYGTGYCTPPICVCYDLYT
```

FIGURE 10A gatcttttttctgggctaattcatatgactcaaattcattatagttgcataataataatgttatgctttttcattttcatttaatagatgttgagatcgttaccagtttt
ttgctcttacaaataatacttttaataaacatccttgaatatatgtacttccatgttttacttctccacaataaactaaaagtgaggtcgatgtatctaaggttatg
cacattttttaatagatgctgccagattatttaccaaaggtcatagaaattatatccaaatagcagtgtaggagaatatactttactcacaccttcacagtatt
ggaagttaacactatatgtaattttttgacagttaagcaggtgaaaggtgttttcttacttaattttcctggctacttggaaacttgaaaatcttactatatatttaca
aacgtttttaattccctcttcctcagattttctgctcttactctttatctgattttctgttgaattatattttttgtcagtttgtgggcaaccatgtatgttttacacattttct
tatttgactactttttatggtttctgccattatttccatctcatgttgtaatggccaatattaattactaaattagatttattgaaattataccatgccagcttgagatgt
ccattcaagtcctcttgacttggattttttataccacttattagcaatattgaggatatgtttgtgtatgatgctttataaaataaattataaaaacataatgtactgtt
atgtataatagaatgtaagctaaagtgattacaaaatacacatttttaaagtcttaagttcttcttttttagaaagcattttgtaaccttagtgctatgactactactt
ttgctttcttgttagagtaaaatcctattttttgatgttcatttggtcattctattaaatttcataagttactattttatccatctccgcttttatttcctctacactgtatttt
ttcaacatgataaaaaactttcatacatggtagaattaaaacagttgtacaatgaatactcaaataactaccagctagactctccaataactatttttactttgtgt
gctctgtcacgtgtatttatttctacatatctctttttttttttttttttctttttgagatggagtctcgcttcgtcctccaggctggagttcagtggcacggtctcggct
cattgcagcctccacctcctgagttcaagcttctcctgcctcagcctcccaagtagctgggattacaggtgccaccaccacgcccagctaattttttgtatt
tttagtagagacacagtttcaccatgttggccaggctggtctcgaactcctgaccttagataatctgcccgcctcggcctcctaaagtgctgggattacag
gtgcaagccaccgtgcctggcctatgtgcctcttcattcattaatttatatttttttatacatttcaaagtaagttgcagacataagtacatttttctaaacactgtgg
tatgaacataattagctagagtttagtagttatttagagttttttttatttttgaggtaaaattagcagtgaaatggacaactttccatttttatgaaccactccatgag
ttttgactaatacataaacgtgtaacccaaatccctctagatttgctgttctagaactttgaaaaaattgaatcatatgtactctttttgtatatactatatgttttg
agagttaatcacacattgttgcatatatcattagtttgtttcctttttaatgcctagtcacatgatatgcggtagacatttttttcttagataggaatttctagtttgttatg
acatcatttgtttccttttcctattagatggcttcaatgtctttgtcaaaaatcaagcgagtataaatgtgggcttatgtctaggcttcccattcaatgcttactag
tatagtgtgaagtatgcatttttcctcacactaaattttcagttattgcagcaccatttgcattctccttgcattgctttgctgctttagtaaaaaatcaaaatacaat
gtaaatgtgggtttatttccaggctctctatttaatttaattcagttgatctattttcaatcctgatgccagtaccgtgttgtcttaaattactgtaagtttatagtaa
gtcttgaagtcatgtacatggttctccaacttgttattttttaaaatgttattttaatattctagattttctgcacttccacataagtgatagcatctgctttgcaatct
ctacaataaagcctctgctatttgtttgtttgttgttgttttgaggcagagtctcattctgttgcccaggctggagtgcaatggcacaatctcagctcactgca
gcctccacctcctgggttcaagtgattctcatgcctcagcctgctgagtagctgggattacaggcatctgcaccacacttggctaattttttgtatttgtagta
gagatgggggtttcaccattttggccaggctggtctctaactcctgatctcaagtgatctgcccacctcagtcctccgaagtgttgggattataggcgtgag
ccactgtgcccaccccagcctctgctattttcgaaggattatgctgaatttacagattaatttggagagaattgatatcttaacaatattgagccttctaaatca
tgaatgtggcatatctcaccattttatttatattttcttcagttctctcagcaacgctccattgttttcagttctacaatgaagttgtaatggacttaattttttttgcctt
ttccttttatagGCTCTGGATCAGTATCATTATACGAGGTAGAAAGATGTCAACAGCTATCTGCTAC
AAgtaagactatgtatcattttttgagatggggcacagtaatgagcataataaagtctgcctctacacttaccagctaatccatttctttctaatagtagaacac
atatcctttaaagctaaaatatgtccatatttaacttctttcttctaccgtgtctgttggcataaaatggaacccataaagataacgtgtctttacattgcatatttt
aagtcatctatctctaacagacttaatgtttaaaacagatatgttttaaacattaaatacatgatgtatttgaagtcatgtatctctgttagagttacatgacttaa
aatgtgcaatgtaaagacacacatatctttaaactattacatgaagagtttatcctgtcacatgatgcatttaacagtgtaccataaaggagctccttgcaatatgc
ctcaaaattttaatttaatgttagtaatgatagtgtgtctatcaagtaccctccttctgctacatcagctaagattaaaaaaaaaattttcagaaaaatatttttaac
cacaaatttattaaatgtgctattgtaaaaattttaatttctcaaattggagaaggaagataacaaatgtgaatggaagaaggattgatgaaatctttaatgtt
gtgttgtaattggaggtaccattatgtactcatgtttctaggtaaatacagaagtcgatgtagctgtgtgtatgtatgatacgcatatattcacacgtgtacac
atttgtttatattataggggtgtgtgtgtgtgtgtgtgtgtcagtatgaatgtgtgttcatatgtaccctatctctctctccatgaaaaagcatagaggcagcag
cactccagttgccataagcacacctggtgctcagatcttggtttataaataatattctctctaaaggaatcagagctccttggtgaaacagcagatttctga
actagaacaagggaattacaagattagtatggagtaaccttgtactagaaagtaaggggttctcagttaatgatgaaactcgtcaaatggcttaggata
gaacatgtctaggaacatttgagcatcaaaacaaataatactaattgagtaaagcaggaatgcatgagcccatgttgatgatgataaaggaaaaataaaa
tatatggggttaagtggaaatatcttcttaaagtaaaataacaaatataaaagggatantgaaattagaaaaaaaaagctaccattttgtaaccatgatag
tcattgttgagttagttgtgaatctgtggattctaaactatcaggatatttgatgaaaaataagatatttacattttctctagtatattcttgttaaatacaagggg
aaacagtaagttttttagtagagaagtgattggacactacctttaccagctgaataaagtttaggtctacagtaatagaaacactcactttgtatgccccttgat
gtgatgcactgagaagcatacagtatcacttacgcattattcctgccaaaaatgcataagctaaatctgagcctgaggaataaccagacaacacccaaat
tggtgtttattctacagaataaatggctgtactcttcaaatatatcagtgttgtgaaagataaagaaaagccgaggacttatttacattaaagaagtctaaag
agacatgagaattaaatgtgatacatggtccagaattggatcttagacttgaaaataaaatgaatgctaagaagaacattttgaggacaattgtagaaattt
gagtaatgtttgttaattaattcgattatagtaataaatcagttaaatgttctaatgttgaaaattgcctgtaattatgtcaataaaatgtcttctttttgaaatacata
ctggaggatttagaggaaaggaggcataatgtctggtagttattctcaaatgattcaataatatttatgtggtgagagacagataaagacaggcacagtga
caatgataaatgtgcaaaaatgttaacaattggtgaatcttggtgaatattatacagaaggtctttgtattgttttgcaattttccttaagtttgaaagcattttaa
aatgaaaagttaaaaactttaggttaaaatatgagtttgaagcaattgctcttatcactgtgtagcaatgtacactaaattgatcaggtctgccaatggcctttt
ttttttttttttttttttgaggcggagtctcgctgtcgcccaggctggagtgcagtggcactatcttggctcactgcaagctctgccttccgggttcacgccatt
ctcctgcctcagcctcccgagtagctgggactacaggtgcccgccaccacaccggctaattttttgtattttagtagagacggggtttcaccgtgttagc
caggatggtctcgctctcttgacctcgtgatctacccgcctcggcctcccaaagtgctgggattacaggcgtgagccaccgcgcccggtgccaatggc

FIGURE 10B cttttttaaaagcatcaccagctgggtgcagtggctcacgcccgtaatcccagcactttgggaggccgaggcgggcagatcacctgaggacgggagtt
cgaagccagcctgaccaacatggagaaaccccgtttctactagaagtacaaaaaattagctgggcgtggtggtgcatgcctgtaatcccagctacttagg
aggctgaggcaggagaatcgcttgaacctgggaggtagaggttgtggtgagcagagatcgcaccattgcactccagcctgggcaacaagagggaa
actccgtctccgaaaaaaaaaaaaaaaaaaccacaatcgccaccacaacaaaatgttccactgtaataaatgttccactctgatgtaataaatgttccactct
gataaaggcaagtgagaaataataaatgatgaatatatttgggcagactcatttgtcacagaagtatcttaaatataaactttattaactgaaatatttgaaaa
gaggtgtaattacttgaaatatctaattaagtgatacagagagccttgttggtaaacttctgtccttcttggccatttgctccttgaaggaaaactaattcaaca
agaatttcattggattaaagctcagtactgaaaggaattgtcttcgccattgaggttaataagatttgtacatcatttccctttctaaaacacatgaaagtgtta
agctagaatgtatagcaagctgttgccttaagctaagggtcaccagcaatttatactttttcccagtaaaaactgatcactacaatcccaggccatctttcc
acaagtagctgaggagacctattgtacctatttcccaggcaattgctcctaatgctttttgtctgagttttttttccagtttgactcaacttcctcttatttttcctctc
cctcctcctccactccctccttccaactccccaaacttcctcttctccactactacaccactcctgtgacagttagatcacccttaatgtcccttcctattcttaa
tctgattttataatgatggttctgtaaaaagtaactgatttgaaacatccaagagcctgcaaataatatttgcaaataatatttacaagtgtgttttgttacattct
tttgtggcagacaccagttagaacttaaacggttgcctagcgtaatatttcttagctaaataaaaccttgctttttgaatgcttactaggcagttaagttacttat
ttcttcccccaaattatccagcgtttatttagtacacatttgttgagtacctactgtgcctggcactatgctagtgggccttgggtatacatcagggaataaag
acataaccttcctttcatggagtgacacttaatagagcttaaattaattagatttttatagtatatatttggttcaggaggatgcatgtcataaatatgattcttgtt
attctgattgaatataaaaattctttacagTACTTACAGATCATCAGTATTTGGAGAGGACACCACTATGTGCCA
TTTTGAAACAAAAAGCTCCTCAACAATACCGCATCCGAGCAAAATTGAGGTCATATAAGCC
CAGAAGACTATTTCAGTCTGTTAAACTTCATTGCCCTAAATGTCATTTGCTgtgagtattttccataataa
aacaaacgtttcatattatttgtgtgtatatgtacacatatgtataatttgtgtcttaggaataagtaaattgttaatatatatattatattttgcaagaatggtaaa
tttttaggtaaagtgctaaattcttagagaataaattattctgatagtaataaaagtgggtgctattttcagatctaaaattcagcttagtcactctgataaagg
caaatgagaaataataaatgatgaatatatttgggcagactcatttgtcacagaagtatcttctgaaatataaaccttattaactgaaattttttgaaaggagtt
gtaattacttgaaatatctaattaagtgataaagagagccttgttggtaaacttctgtcctgcttaataactagaatataataaatataattaaattttctttagta
attgagaatttctcagtgccttactctgaacatcagtgattatataaatatgtaataaatgtatataactgttttgtaatccttttactacataatcggctcaagac
atattctgaaaatcattttttaaaagctcctcatctttttgcaatttgcctactttttcctctgaatatctaaaatgatgtttttggaaaatgtagataattgatggttatat
gcatttggatgccctaaattgagtcttcactaaaatgtgctacaatgtgtaaatatctatgtacatcgccatgtatttgtgtgcttataaattgtgagtatctgtgt
tcattaatatacatatattttccaatccaaaatttgggtttgtttgaagaaattttttattttaaaatctctttaaataaaatgtgagggaactgttttacccatttga
gcttgaaatggtggttgggattaaaatgtatatataaggatttagataattcttcaaatattatcaaactttggtttattgaattttgtaaaatcatacagctttgta
aaataaaaccactctccgcgatcatttttaaacaaataaggatattatctcagaaattaacgaaactgtctaaagttacacagttaactggcaacagaac
cagaagaaagccatacacctttttgattccaaatgatgccattctgctacatggtacctaaccatatgacttcttaaaattattaattattaaacagaattggaa
atattattagtttagaagtgcccttctccctaagtgtggtaagtgatatttaactggagtgaagacggggccactgcatttttttctcctactgggaaatttag
cattctttacagaggagaaaaaaattgatgctagaaataattatgagtaactttgtatcacaaaaccaggcatagaaatcactggtagttaatgtaaatatga
tttggatatacttacccacaaaatatcaaataattatctattgaaaaaaaagttatttgttctgcaaagtgaattatctccataattttacataatttaagaaaaagta
actgactcatctacatgtaagaatgatacttttttaattttgataacttgttaaatgaaatcttcacgcttacaccaaaatcgatttctatcatttcattgccaataat
tttagGCAAGAAGTTCCACATGAGGGCGATTTGGATATAATTTTTCAGGATGGTGCAACTAAA
ACCCCAGaTGTCAAGcTACAAAATACATCATTATATGATTCAAAAATCTGGACCACTAAAAA
TCAAAAAGGACGAAAAGTAGCAGTTCATTTTGTGAAAAATAATGGTATTCTCCCGCTTTCA
AATGAATGTCTACTTTTGATAGAAGtaagatatttaagtcactgttttgttagaatactccttttgcatattttttcctaattaattattgtt
taatacattttacagacaacctagtacatataaagtaaaaatagtatttaaatttaacaaaattgaatatatatgttaactaggttcaaatatatataagcacacg
ttcataaatttatcttaattacatttgaaattgtacttcagactcaagtgttaacatttaactatattgttggattgcatttattttgtcaatgctaagctgattgtcta
gttaagtaataataaaagaggctgattgcttatgtaccattgctgttttcttggcctctggatgtcactgttgtttcatagaaataggtgaaagtcatctattgt
atcaaaatcaaagaagagaccattgaaacaagtaaagataacttgacaagttttaaatgaaatttatcatgtttggtttttcattttcttttcattttcatctaattttt
atctcatttatctaaaatatgtactgtgaattttttttcatggcaaatttagagtttttcttaaggcttctcttcccttgtaacctttttcattgttttctttaaggcttttcctt
cccttgaaaccttttcattgttttcttaaggcttttccttcccttgaaaccttttcattgttttctgaaggcttttcttccttgaaaccttttgtaatagaagaaaat
accttcttttaatttgccttagagtaatatttaactttattttttaataaatgagggaattctatgtaaattatagactttgggtgattatgtgtcagtataggttcattttt
aacaaatgtaccacgctggtagaggatgttgatactggaggaggctagcatgtatggtagaagggatacggaaaatctctgtaccttcctcttaattttg
ctgtgaacctaaaactgctccttaaaaaaaaaaaaaaatgaagtcttaaaaagaaaacatagaatgtacaacactgagagtaaaccctaatatagactgga
ctttgagtgataatggtttgttagtaatgtaaagtgtggacttttgagtgataatggtttgttactaatgtaaactgtggactttgagtgataatggttttttaaaat
aggtttcttgattgactaaatttaccactctggtgcaagatgttgataatggggaagaggctaggggacatagggaaactttgtaccttttgcttaatttttgca
gtgaacctaaaactgcttttttaaaaaaggcttatttaaaaaaataatgagaatgtatgtaaaagcactttgaaatgtaaaaggaatataagaaatgtgagcta
ttttatttttatgtttctaagtattataacctggaccaagggctaggatcttactgcagtatggcactgctctggttaggaagtaacaaaatcaaaaactgacct
ggacttagagatgaaccaaagaaaacgataaaatacaaagtcattcttagacttttaaggacctgcagcagtattcactgatattcatgccaagttaatgca

FIGURE 10C gttgacactatttattgtgaccatagtttacattagggttcactcattctgctttacagttctttatgttttgacaaatgcagaataccatgtacccaccattaga
gtctcatataaaacagtatcacttaatttctgtaaaagctctaagatctgtgtccagatttttttttgcatgcagatgtccagttttccagtaccatttcttaaaaag
actgttccttctccattgaattgcctttgcttctttgtcaaaccagtttgtgtgaatttgcttctgtgttctctattctgttttaatctgtctgttattttcctaatatcaca
ccatccttatttctaaagctatatagtaattcttgaaattgtgtagtgtttgtcctgcaactttcttcttttttcttgagtattgtgttggctattgtaaatcttttgcatttc
catgtaaactttataatcagtttgtcaatatccaaaaataacttgctgggattttattaagattgccagctgggcgcagtggctcactctggtaatcttagcac
tttgggaggccgaggcaggcagatcacctgaggtcgggagttcgagaccagcctgaccaacatgaagaaacctgtctctactaaaaatacaaaatta
gccaggcatcatggtgcatacctgtaatcccaactactcgggaggctgaggcagtagaatggctgaacccgggaggcggaggttgcggtgagccg
agatcgcgccattgcactccagcctgggtaacaagagcgaaacttcatctcaaaaaaaaaaaagattgccataatctataagtcacggtggagacaga
gaactaacaacttgatgttattgacgatgaacatggactatcttctatgtagatcttcttagatcccttttaactagggttttatagtttactcagataaaccttat
aaatccaacaaaatatagatcacattttgttagctttatatctaagtattttcttttttggtgctaattatttaatgttaaattcaaacttttgattatttattgcttatgtat
agggaagcaattgatttttttttttaattaaccttgtatcctctaccgttgctataattgcttgttatttcaggaatttttttgttgtgatttcctgtaaacaaagacagc
ttatttcttccttcctaatatgtataccttttgtttcctttcttactgcattagataggcttccagtacaatattgaataggagcaatgagagggaatgttcttgct
tttatcccagtcttaggtggaaagtgtcaccattaaatgtaatttagctgtggctattttatcgatgttctttatcaagttgaagaagttccccaatattcctagtt
tgctgagaatttttattattaatgatgttggattttatcaaatgcttttctattgcatctattaatatgatcatacaattttctttcttttagcctattaatgtgataaatta
cattaattgattttgaggtgtttaaccagccttgcctacctaaaataaaatctcatttggtcatggtgaataattatttttcttttttgattcaattttttaaatactttctga
gtattttttatgtgttttcttaagagaagttgatcaataggtcttcattcttgtaatgtatttggttatgtattagaatattgctggcctcataagagttaggaaaca
ttccctctacttccattttctggaatacatagtagagaattagtgtcattcagtgtttgggtagacttagctattgaaacaatctgagcctggtgacttttttcaa
gattattattattgatttaatttctctatagacatagacctattcagattatctgtttctccttgtgtgagttttgatagattatgcctttcaagaaatggaaccatttt
atctaaggtgtcaaacttgtgggttcgaattgtttataatatttatttattattaacactatattttaaactgcataacatttaacttcctctgaaacattttgtattgttt
ccaattgaattgaatccaatttgtatggaactctaatgtcactgaatcattttatcataatatttattattaatacctataatttactgaatagactatgtgtcaggc
actgtactagtttagtattttatctttaactctcataacagttcttctgtaagctggatatatccccttttgtaaacagaagaggaaactgagaccaagagaaaat
ggtgaagtactcaaggttaaagacttaataaatgtcagaaaaaaattcaaacttaggcctttctgtctccatagtccatgttaaatatttctactgattgcaaat
aaattgctctcagttaggatgtctccagatacaaaccttgagaaatgtagtatgcacatatatacatgtaaatgtctttctttgttcttattcatttgtttagcacat
gtttattgaatgcctactatgtgccagacactgatttaggcattagtggcaatgtagcaaacacaacaaagttcttcctttcatggactttacattaagaggaa
atcactaaaatattgatagtaatagtcactcatggctctaagtgctttacaaatattaactcatttaatctttataatgatcttacagagtaacattattctcagtttt
gcaaatggggaaactgttataccagagtttaagtaacttgaccaaggttgtccagcttatgtgccagagccaaactcgtgtgactggccagtgtgaatga
ctagatgagctctcaccagattctttgaaatagtgttttttggggaggaactcatagagaaaagagttagtgaatggtcacctattgcagttttgaacagtag
gcaggagtctcttcagcagggctaggtatcagtctccaaaagatagactaacttttgggctgtgaaacttttaagtagcatgcttagggaatattgttttgag
tttttaagcatgcataatgagagtttctatctagctgcaatatgatatagcagaactctggcttccagtaacaaagagcttgggggaaggaggatgggaac
agggcaagttaaaatgccacagagctcaccgttcttgccaaaattcagcccttttttctggagcaaacactccttggattgttgaaggcctctggtaatttcc
agaattctaaaaaaggttttacagttttttgccaatatttcttactgctgttatagtcaagtgtgtctttggatgtcctcactctgctataccagaagtgcttctcctttt
ataattgaatgttgacattacaaattctacccaaattttaggaaatacacagaggtattttttaaatcctttcatttttgcctggagagaggaagcattattagct
aagtaaaaaggacactgccttctaataatggatgccattggacaatactctcagccagcctggtcattgaatgcttactctgtcatagaattaactgtgat
aattttcccaggaaaaatgaacaaatttatatgtgaattcatattacatgaactactcatatctatatttaaatgaaatattgacctgaaaattgagatttaaact
ctaaattttgcccagatattaattagtatatagcaaattagtgagaatctgatcataacttagcttttaatttatattccctcttttggttatttgaaccaaagtgttcc
tgaaataaagagcaatttgtttaaatttaagaagttggttaaaatttcacaagcttttatattttaccaaagtctcagcattttttgtgcattgatttttttaatcaatgt
ataggattgtacatttacaaattaatatttttttacatacattcattgtcttttctgtcaattcctttagtcttttattatacctcacacgttatttaataggactgtacttg
tctacatttatttgcactacttgaaggatttatttattctcttaacagGAGGTACACTCAGTGAAATTTGCAAACTCTCGAA
CAAGTTTAATAGTGTAATTCCTGTGAGATCTGGCCACGAAGACCTGGAACTTTTGGACCTTT
CAGCACCATTTCTTATACAAGGAACAATACATCACTATGGtattttgttttgttttgttttgttttgtttattatactt
ttaagttctggggtcatgtgctgaacatggaggtttgttacgtaggtatacacgtgctattgtggtttgctgcacccatcaacccgtcacctgcattaggcat
ttctcctaatgctgtccttccctagcctcccaccccctgacaggccctggtgtgtgatgttccctccctgtctccatgtgttctcattgttcaactcccactt
atgagtgagaacatgcagtgtttggttttctgttctggtgttagtttgctgagaatgatggtttccggctttatccatatgcctggcaaggacatgaactcatc
cttttttttggctgcatagtattccatggtgcgtatgtgccacattttcttaatccagtctatcactgatggacatttggtatagttccaggtctttgctattgtgaat
agtgctgcaataaacgtacatgtgcatgtgtctttatagcagaatgattttataatcctttgggtatatacccagtaatgggattgctggatcaaatggtatttct
agttctagatccttgaggagttgccataccgtgttccacaaagattgaactaatttacactcccaccaacagtgtaaaagcattcctgtttctccacattgtct
caagcatctgttgtttcctgacttttttaatgatcgccattctaagtggcgtgagatggtatctcattgtggttttgatttgcatttctctaatgatcagtgacattga
gctttctttcatatgtttgttggctgtgtaaatgtctccttttaagaactgtctgttcatatccttcacccacttttttgatggggttgttttttttctttttaaatttaagttctt
tgtagagtctagatatttagcccttttgtcagatggattgcaaaaattttcctcccattctgtaggttgcctgtttactctgatgatagtttctttgccgtgcagaag
ctcttttagtttaattaggtcccatttgtcaatttttggctttttattgcctttgcttttggtgttttagacatgaagtcttttgcccatgcctatgtcctgaatggtattgcc
caggtttccttctaggattttatggtttaggtcttacatttaagtcttttaatccatcttgagttgattttttgtataaggtgtaagggggatccagtttcagttttctgc

FIGURE 10D atatggctagccagtttttcccaacatttattaaatagggaatcctttccccattgcttgttttgtcaggtttgtcaaagatcagatggttgcagatgtgtggtg
gtgttttcaactgagaaaactttttggaattaaaaactgttgaagagtaattttattagtttatttcattggttactatatgttcagcatgaacttacagtgtatcaa
cttatatgtactaggtttttctggcatatatctgttcttttgataagcatatatagtgagagtacacgcaatgtgtgaggcataaggctgctgtcttttgattcctc
agccagaggctggtactcacttgttttctttaacagtgaggatttagattccagttacagagaaaaattcagagctgcaaacctagtaaaaattaagtgattc
aatttcagaatttctgagccactaaattacaaatttgctgccactgaaaattggaatataaaagaattcattaggagctataaacagatttctacatttagaag
gaggggggtagggataaaatctcctctactgcttgatgaaacaatcaccctggacacattctgatttgagaaaccttggattataacatatgttttatcatccta
ttcctctttctttccgacttctacatttgtagcaattagtagtcattgtcataatgtgtaaatcctgattgaaaaattatatactggttgaaaaatattatacggtaa
gcatgatacctccctaattgtgtggtaaagtcactgttaggcattgccctctgtccttccaacatatcataaaattttagccataaagcgaaagtgtatgcca
ctgacttaaatctctgtgttatagctgttttttactgatatactcagtgtctaattctccctctcattagactcatgatctgagagtccatcttttttgaaaataaaatg
atttttaattaagccaattaattaaaaaattaaaactcataaaattcagtttttcttgtataataagtcactgagctttctcttttgcatgctcatcctcgctcacttg
cttttgttctttccccttttctctctatttttgccttgccagtactgggcaccgtgacgcgtctaaaccaggaaaggaaatattcatattcatttttaaactctgaaata
ctactacttcttttactagaagtctcaaaaaaattaccttaaggaccccatttttttttttttttttgagatgaagtcttgctctattgcccagataggagtgcagtg
gcatgatctcagctcactgcaacctctgcctcccccggttcaagcgattctcctgtctcaacccccccgccgagtagctgggactacaggcatgcaccac
taacacccggctgattgtttcgtattgttattagaaacgaggtttcaccatgttggccaggctggttttgacctcctgaccttaggtgatctgcccacctcgg
cctcccaaagtgctgggattacaggtgtgagccactgtgcccaaccaaggctgttgacttttttactggttgcttcaaaactaaggcaaatgctgttcacact
ccagatttttaagacattttttacattttttattacttgagtttcatcatcaaaagccagtatatctttttaattgatticttcttttattttttgggttatgaaataattttaactt
atagaaaaattaaaaaagtaacatcacaacaattacgtatccaccattttagatttaacaaatcgtaacgttttgacattatttcagacttttttttttttttttttttg
gagacagtgtcattctgatacccaggctgaagtggcatgatttcagctcattgtagccttgacatcctgggctcaagcaatcctactatctcagcctccca
actagctgggactacaggtgcacaccaccacacctggctaattttttgtagggatggggttttgccatgttgcccaggctgttcttgaactctggagttcaa
gcaatctgcctaccttggcctccaaacttttttttttttttttttttttttatttttaagaaattaaatgttacagagaagtagtataatgccatatcaatccttctctaac
tcttttttctcagaggtagctacttttccaaacttggattaaatccttctcatcaatgttttatgccttcattatatgtgtgaactcttaagcagtatggcatattttc
attttttaaatttatataaactgtttcgtactatgccaagccttttgcagcttgctttttttgattcattaaaattttcaagatttaccactattgacgcatgtagattta
gattatttaacatctttggagtatgttatgaaatatcagaatttattagcctatttttcctattaatggatatgtgttattttttgtttcatttacagaccataatgaagtc
acgttatatgtttttcttgtctattccccttgtcataaaatgagttcagtgggtcataaacagttttttttttaaattatatgatgtggttgtagtaaaaaatggaatgag
agggaatggataatagagaacatttttacacagtaagggtcagtgttgttccttaaactttcatttcaattgtatgtgtatgtatgtattactaagatatgatatta
aatgaatttcttactgtgagtccttaacaaaaatgtttgaaagttactccttaaggtgtttacctgaaattagaattactggattataaggtgtatataagttttgct
ttatgggaagaaataccaaaattgttcttcccatggttttaacaatatatggtcccatcagtaatgtataaaattttagttttctaccaagttcactccaacacttgg
tattagtctatttctgtctgatacttggcattaattttgtaattttgtcaggccagcgagcatcagatggtatccataatgttttatttgtatttcctagatgtctagt
gtgtttaagcagccccccgtgtttatcagctacataggtttcctactctatgaattccatgttcacatctttgcctgtttttctatgtggttactgatttctttgttggt
tcatgtgtgagcgcacatacatgtaattgattgtaaggtttcttttccgtgttagagatactaatctttgtcagttttcatccatacttctagtgtattccatgccttttt
aactttatggttcttgtgttttataggttttttttaaaattttttgtttggtaaattgctttataggttactctcatcccctttgctttcaagttttctggcattctaatttgtatgtc
actcataaaataaaagcttatggctaaattttagttttaatagtggagtttaaatatgttcttaagttattgatatatttagtttatgtttctaattttttctgtttcccctttt
cactgctttggaagtaagtagttctgtatttaatttttgacttaatatccttaattttttaatttttatactaactttaataatgtctaatgctaatcaatatcgtagtcttttt
cttaggcaataatattcttttgttaaattgacatcttttattagaaaagaaacacctatatatttaataaatagaagggtataagatgtaatgtggttaccctcttg
ttttcctcaaagtgcaaatgaaaacaaattgcatggaccttcgaacttttattttttattcaagtatatcttttcaagtatatttcttatcaacatctcataaacatta
tgatgatgcataataaaaaataaaattactcatagttaaaatatgttggtattcaagtaaagcaaaataactgtactacacaatgcacaactttagtgtattgtgt
agtcttagatttatatacatttcaaaagttaactatggaattaggcatcataaactacaaacctctggatatgtgcttactaaaaatattaattatctagaatcttg
catgttgtgactgtttagtaatttttctctattggccatatttattaacactttgaatttattaagatattacttacagaggccaggtatggtggctcacacctgtaa
tcccagtactttgggaggccaaggcaggcagatggcttgagctcaggagttgagaccagcctgggcattgtggcaagaccctgtctctataaaattaca
aaaatcacccaggcatggtggtgtgcaactgtggttctagctacttggaaggctgaggtggaggctcacttgagcccaggaggcagaggtgacagt
gcctgggtgacagagtgagaccttgtcttaaaaaatatatatatatagatatagatatagatatagatatagatcatagaatcagagaattcttagagatgat
cattttcttcaactttcattttaacaaataaggaaattgagagcaaaattaattaatgatttggacctggaaccgagcaccctgttctcaatttagagttgtttat
tctgaatcttatactgtcttttattgcccttatgtaataagcttactctttcataattctcttgtgaaacaaacaagcacattacaatatagggatgcagtattc
ttctgtttaataatttatattttaaaactacacatgtttgagcagtaaaaagttataacaaacaagctaaattattttttaaatatttatggttctttcttttataaattca
gATGTAAACAGTGTTCTAGTTTGAGATCCATACAAAATCTAAATTCCCTGGTTGATAAAACA
TCGTGGATTCCTTCTTCTGTGGCAGAAGgttagctaaatttccatgccctgcaatttttaactgtttgtttacaaggttatttccaccta
cttatatttcagtatacctgaaagtatacctgttccttctttgtatacttattccttcctctgtaagataaacagactttgtaaatttaaagatatctgccaagccttc
ctttagtctgtatttcttcaagcaggcaccgtcacatactttccccctatgccttactatttgtttttcctcctcagtaagcattccactttaccagtgcttttctcag

FIGURE 10E aatttggcattcagagctggacattgtgctgcagatgttgtttggccaattcagaatagagtgaaattattatttacctgaaactggacactcagcttctacta
gcctgaaatgtcattgtatagctatttatttgtacacttggttttgttttctttcctttttgatacagccatctcatgttttatttgtggtccagtgaaatcctagggtc
ctgtcacatgaacttcttgaacttggtcttctcattctattcttaatgtaattttttttttctgtcacatgaacttcttgaacttggtctcttcgttctattcttaatgtaata
tctttgttttatggttcctgggagtaggtgctaagttcatctttcttagttttagttcacagtttttaacctattgagaccttttgaagcctaaaattcagttcccctgt
attaatgtctgttgtatgccctagttcatgtctgtatgtcctaatttattcttacttttccctgttaattagttatactgtttaaatatgggttccacagataaaagctaa
taaaacattctataaattgagtatcttccatttccaaacaagaagatatttatcttaacctgtgaattttcatttttacccagtatgtctaatttcttatttcttccttatct
taccaaattattaaatctcagattctgacattcttgtccattcaaccagatgatatccctttttctttttttaaagttataaattattcccctagcttataatagaaag
gagagaggcatgctaaaacggtatttaactgcatgctatttttagaatatatctgtattttaatttatctttcataaaactaacatgcaatgagttacatttcatga
atcactttttgtggtttctatggaggctatcaactgtttttttttatttatttatttttatttatttgagacagagccttactctgtcgcccaggctggagtgcagtggt
gcaatctcgactcactgcaacctctgcctcccaggttcaagcaattctcatgcctcagcctccagaggagctggaattacaggtgtatgttaccaagcct
agctattttttttggtattttagtagagacagggttttcatcatgttggccaggctggtcttgaactcctcaagatccgcccaggtgatctgcccacctcagcc
tcccaaagtgctgagaatacaggtgtgagggtgtcaacttattttaaatacgttaatatttaatcaaaaagattaaattgcttatcataagatattctccctatgt
aggtatagtgaaatattccaaaatgaatctgctaaatgagcttaattataggttgagtatctgtggagttaaaaacacaaactgtcctctgctctgccaccac
agcaatcagcgcagaagacttatgtgaccaaatgcataggggttttcacccacacaccaagcaggcaatccctcagcagacgccagctgggtgtcct
ccagttcaattctgacactatctacctggagataatgccaagttttttctttgtatcttgagttatttagtaaataaaatttacaggtctatactatcataaaacaat
tttaactttaccttgataataaggaatagcagactcatatggtttgatcttttttttccttcactagCACTGGGTATTGTACCCCTCCAATA
TGTGTTTGTTATGACCTTTACACTTGATGATGGAACAGGAGTACTAGAAGCCTATCTCATGG
ATTCTgtaagtatcagaggtaataaagatattttttaattaaaaaataatatttaaaaaattgaatacatttattcatacctgctttgttcctaaaaggacttaa
ggcaccttaaaaatataagtaaaatatgagcacatataatcttgaatcatctgtgtatgtatctcttttttttatttgacactaaatcttaacatttgaatagtgaaaa
attaaggaacagggatttaaagagtcattccctataccatggccaaaatgcagagatacggccacactatggaagcattatttgtagtcaacattttatcgt
actttttgtttgtttgtttgtttgtttgtttgtttttgagatggagtcttgctctgttgcccaggctggagtgcagtggcacgatctcagctcactgcaacctccgc
ctcccgggttcaagcagttctctgcctcagcctcccaagtagctgggattgcaggtatgcaccaccacgcccagctaattttgtattttgtagagacag
ggtttcaccatcttggccaggctggtcttgaactcctgacctcatgatccacccacccttggcctcccaaagtgctgagattacaggcgtgagccaccgt
gcccagccttgatcatacttttaaacctccacatttcatattagaggaatgaagttactttaacagggaagatagatattattgtataaagttttgaggcagtc
tacaaaaccttcctcatttctgacactaattgcaattggaagtcctcaaggccactcttagatttgataattcacaagactcctagaactcactgaaaactgtt
atactgacagttacagattattacagctaaaggatgtacattaaaatcagataatgaaagagatgtataggacagagtccaggaaagttccagacatgga
acttatagttgtcctctccccatagagttgtggactgttactttccctgcaacagtgtgtagcagtatacataatatattgccagatagggaagctctgctaaa
agatttagtgggactctatcacgtaggtatggttgactgcccatatggctgatcatagtcttcagccctcttgagatcaagctgataccacatgctccaa
actttccaccctacatcatattgttaaactattcatagtgacccaggggcttccaggcaaaaatacttctatcaagtgtgacatagaaagggcttagagattac
gttccacaagctaaggtcaaagcccagacctctcttagggtaaagttaaaatgtttactacatggattggaaaagatctgagttatagttgagaggagaat
ttttctcccacctacacaattcatttaacctttcattaaatatttaatgagcacctgctatgtactaggtactatcctatgtgatggagacacagcggtgaacaa
agtaaacaaaattccttccttcttgaaacttataacatagtagggaagagaaaaattaaataactatataatacatatactgtatgttatattcatttaagcttag
cacaagatttttttttctatgcacaaagagaatagtcagcctcattgtttttaaatcattattaccatcatcattattaaatcagagcaatttacttgattacgtgtat
ctcaaagctattttaagattaaagagtaaataagattttggagttgagaccagcattctagtttatgaattctacaatcttgatagagggaaactgtctagatta
tctttaattggacaatattgaaatatgtgttaataataacattaaaaaaggattaatatatttttccttttttttttctctcatgaaacatttttaagGACAAATTC
TTCCAGATTCCAGCATCAGAAGTTCTGATGGATGATGACCTTCAGAAAAGTGTGGATATGA
TCATGGATATGTTTTGTCCTCCAGGAATAAAAATTGgtaggcaagaatatttttaacaatcccacacttctttacttgag
atagcactaacatatatgtactctgtggactttttagaagtctgaaagctttgcttccaaatgatttactaagtagtgagtgattactctatgatcaacctttgatg
aagagagtggcagggataaaatagttatgaatcataattcctgcagtcaaaagatttttaaaatattttaaatataggaaaggggatagttttgatcacaa
gcacatttgacattgtcatgctacaagcattttagttgaaattagaccaaaagtgatgaattgttggcagtaaacattttctgtaacaaactccaattatccaat
ttaattcatggattaattttttatttattgttaactagtttcagatttttacaagcttttgttttaccaatttttttgtgagctttgttttctgcataaacatttgattaataaac
cagatcttcctcatttcaaattgtactgcttatacctgctgccactgaattttccttctgtgactatatttgtacttatgttgaaacttgcagatctaagtcatattaa
gacaattttgatttttctaacaatttttttatcgtaggaaattttaccagctgcagatttagcagctggttttaattttatatactattttttaatcaggcttactctccct
ggtcaatctttgcatcttataatagttacataatgatagggaatttgtgttgatctctaaccaagtttaacttgaataccttttatttgttgtcagtttttaatttgtgttaa
ctgtttggattctttttggatagatttctagaagtaagtctttatatccaaaagcatgggcctggtagacccattgtaaccactatttttagattttttaaaatatatac
caaccatttttgaaacccaagatgtactcactgttacctgcttgtggcaaaaaattcaaattagtcacaattgctccaaaacaataacatgaatctagtatgtat
tttgaagagagaataatgttaaatttggaagggacgtttacttactttttcaagccaaaataaatgttaattttttctagctcagtggtaagcttaggtacctatttc

FIGURE 10F agagttatttatttttgttttaatggttaaatcgcttttttttgtttttgtttttgtagATGCATATCCGTGGTTGGAATGCTTCATCAAG
TCATACAATGTCACAAATGGAACAGATAATCAAATTTGCTATCAGATTTTTGACACCACAGT
TGCAGAAGATGTAATCTAAtattgccatccaatttagcatacataaaatgttgccactcaccttccctgtttgagcttctttcctgacctga
gttttgtatcagcaatgttgatgatgttagcatgggtatgggattagaaaatgtccttaccttaaatctcttggcttttactgggtgcaaggtaaataatggcta
tggatttgttttgctttctgttttgcttttgtacaaagagacctgcttaaacaagtactgctgagataagtgtctgatcaagctacagtgtactttaagtagaaat
ggcaaagttgctttgttggggtgctgatactgatgattttaggataaattcatttctttaaacttgtaatacatggttttattgcttgtttctctccaggatagtaga
gatttctctatttcacctcaacctaataaaagtggtcagatttataatgttaatgacttaatattatcctttctaatagtctcatgtaaaatatgccgctattacaac
ttacaactaattgaatgagatgttaacttagtaaaatagtttgattttacctgacagtgtttgtcaaatttaaaatcatgaatattcaattttatacaaacatttatat
atatatatatagatttgtgtatgttatttgccaaagacagatataaattacctggtttaatattagtgaagaataaataagtgcacacatttcaactgtttcatttat
ttgccctaagttgagctgaaaaatgatatgaggcaaagaatcgaaataggtgtggcaatgcagcagatgtttagggctgtctacatcccaggtactgtgc
taagcactaaacatgtatttgatcctcacagcaacctatttttccgataagaaatctgaggcttgattgataagctgacttgactaagttcacacagtttgtaa
aagctagagtctgtgccttaattcacataatctctattcagagcctgtactgttaaccactcaaggattctggaacagaagctaacagttttctgcaacgagt
ctttgacttaaacatctgaaataacattggaaatagattataagaggagtcagtgtgttttctatagtttcaaaatactttaacatcttattgtcaaaaagattg
gataactgactttctttgctcataataactctaaattctagttcctgagtacattaacacatcttctttacctaactaccaatgtccccatcatcgacttatcagc
ttgtttgagacaatgagaaagactgatttattttcaagaatatagactcttggttcaaaacatttcaggaaaaatattttaaaaccctacagttgaacaggtg
tgtttccgtgttgatgatgtgctcaggatacaaaggtgaaataaacattttttctgccttcaggaagccctcaatctagaagagtagaggtccaaaggtgcc
atatgttcacactgtgagcctgcaagatctccacgttaacaaaggaaaactcttcctatgaatcttcatgatgatagg

*FIGURE 10G*

Alternative forms of hPot1 partial genomic DNA lacking N-terminus

| 5 | 6 | 7 | 8 | 9 | 10 | 11 | 12 | 13+3'UTR |
|---|---|---|---|---|----|----|----|----------|
|(119)|(56)|(156)|(205)|(135)|(88)|(91)|(105)|(112+702)| splice variant #1: 72kDa protein lacking exon 5 splice variant #3: 38kDa protein containing exon 5 splice variant #4: 58kDa protein lacking exons 5 and 10

PROTECTION-OF-TELOMERE-1 (POT-1) PROTEINS

BACKGROUND OF THE INVENTION

Telomeres are the protein-DNA complexes that protect the ends of linear eukaryotic chromosomes from degradation, prevent end-to-end fusions and partake in chromosome localization and segregation (Cooper, *Curr Opin Genet Dev* 10: 169–77, 2000; McEachern et al., *Annu Rev Genet* 34: 331–358, 2000; Price, *Curr Opin Genet Dev* 9: 218–24, 1999). Telomere length, 15–20 kb in human embryonic or germ line cells, is maintained in part by the enzyme telomerase. In the absence of telomerase activity, about 50–200 bases of DNA are not replicated with each round of cell division, resulting in the eventual diminution in telomere size to typically 5–7 kb. At that length, cells enter a state of arrested growth called replicative senescence. The maintenance of telomere length thus is believed to play a key role in the ability of cells to avoid replicative senescence and to propagate indefinitely, as is the case with stem cells. Likewise, aberrant maintenance of telomere length is believed to underlie indefinite cellular proliferation characteristic of cancer cells (Bodnar et al., *Science* 279: 349–352, 1998; Bryan et al., 1997; McEachern et al., 2000).

Telomeres consist of repeating units of GC-rich DNA and terminate in a single stranded extension of the 3' strand. *Oxytricha nova* telomeres, for example, consist of tandem repeats of (TTTTGGGG) and end with a 16 nucleotide overhang of the G-rich strand. By contrast, human telomeres have a repeating sequence (TTAGGG)n and end with a 50–100 nucleotide overhang of the G-rich strand. McEachern et al., 2000.

A number of proteins have been identified that specifically interact with the double-stranded portion of the telomere or the single-stranded 3' extension at its very end. Among the most well characterized are the telomere end-binding proteins from hypotrichous ciliated protozoa (Gottschling et al., *Cell* 47: 195–205, 1986; Price et al., *Genes Dev* 1: 783–93, 1987). The α and β subunit of the *O. nova* Telomere End-Binding Protein (TEBP) bind specifically to the 16 nucleotide single-stranded extension at the ends of macronuclear chromosomes (Gray et al., *Cell* 67: 807–14, 1991) and form a ternary complex whose structure has been determined using X-ray crystallography (Horvath et al., *Cell* 95: 963–974, 1998). Although both protein subunits directly interact with DNA in the ternary complex, only α binds telomeric DNA by itself (Fang et al., *Genes Dev* 7: 870–82, 1993). The DNA binding domain in the a subunit has been mapped to the N-terminal two-thirds of the polypeptide (Fang et al., 1993) and is comprised of two "OB folds" (Horvath et al., 1998). In vitro reconstituted α-DNA complexes are substrates for telomerase, whereas α-β-DNA complexes are not; an observation which may indicate a function in the regulation of telomere length (Froelich-Ammon et al., *Genes Dev* 12: 1504–14, 1998).

The protrusion of the G-rich strand as a single-stranded overhang is conserved between ciliates (Klobutcher et al., *Proc Natl Acad Sci USA* 78: 3015–19, 1981), yeast (Wellinger et al., *Cell* 72: 51–60, 1993) and mammalian cells (Makarov et al., *Cell* 88: 657–66, 1997; McElligott et al., *Embo J* 16: 3705–14, 1997; Wright et al., *Genes Dev* 11: 2801–09, 1997), suggesting the existence of similar functional mechanisms in telomere maintenance. However, proteins sharing sequence homology with ciliate TEBPs were not identified in the complete *S. cerevisiae* genome or among the proteins that bind single-stranded telomeric DNA in vitro. Similarly, the *S. cerevisiae* single-stranded telomeric DNA-binding protein cdc13p has not been proposed to be homologous to the ciliate TEBPs, nor have cdc13p homologues been identified in distantly related species. (Ishikawa et al., *Mol Cell Biol* 13: 4301–10, 1993; Lin et al., *Proc Natl Acad Sci USA* 93: 13760–65, 1996; McKay et al., *Nucleic Acids Res* 20: 6461–64, 1992; Nugent et al., *Science* 274: 249–52, 1996; Virta-Pearlman et al., *Genes Dev* 10: 3094–104, 1996).

The apparent absence of specific end-capping proteins in some eukaryotes has been explained by the adoption of a telomere structure distinct from that found in the macronuclei of hypotrichous ciliates. This telomere structure, found at the ends of mammalian and *O. fallax* chromosomes, is a large duplex loop, or "t loop," created by the sequestration of the single-strand overhang within the double-stranded portion of the telomeric tract (Griffith et al., *Cell* 97: 503–14, 1999; Murti et al., *Proc Natl Acad Sci USA* 96: 14436–39, 1999). In mammals, this architecture is believed to be maintained by a number of proteins, including the TTAGGG-binding factors, TRF1 and TRF2. TRF2 is believed to catalyze the sequestration of the single-stranded DNA into the duplex region of the DNA. Consistent with this notion is the observation that TRF2 can cause telomeric DNA to form t loops in vitro (Griffith et al., 1999). Other proteins have been implicated in telomere architecture and regulation, including TIN2, which was identified by its ability to interact with TRF1 (Kim et al., 1999).

The ability to manipulate telomere structure and metabolism depends on the identification of those components required for the regulation of telomere structure. Evidence has accumulated that telomerase activity itself is not determinative of telomere elongation or replication. For example, some cancer cell lines maintain telomeres in the absence of telomerase activity (Bryan et al., 1997). There is thus a pressing need in the art to identify the functional components that regulate telomere metabolism, to identify compounds that can be used to control the entry, avoidance, or exit of a cell from a state of replicative senescence. Such compounds may be useful alternatively in allowing the indefinite propagation of useful cell lines or in halting the growth of cancer cells in vivo for therapeutic purposes.

SUMMARY OF THE INVENTION

The present invention addresses this need by providing a protein that caps the very ends of human chromosomes, and a related protein that caps the ends of chromosomes in fission yeast (*Schizosaccharomyces pombe*). The protein of the invention is termed "Protection of Telomere-1," or "Pot1p," or "Pot1 protein." Specific embodiments of these proteins are those isolated from humans and fission yeast, hpot1p and SpPot1p, respectively. Polynucleotides encoding a Pot1 protein are also provided.

The inventors have found that Pot1p binds single-stranded telomeric DNA, which is a unforeseen finding, given the apparent absence of end-capping proteins in some eukaryotes. Pot1p both stabilizes chromosome ends and regulates telomerase activity. Accordingly, compounds that stabilize or disrupt the Pot1p-DNA interaction will be useful in regulating the telomere length of a target cell or cell population. The invention thus provides a means of altering cellular life-span, for the purpose of either prolonging the life-span of useful cell populations or making cancer cells enter replicative quiescence. Useful compounds with these properties can be identified through screening methods made possible by the discovery that a Pot1 protein binds single-stranded telomeric DNA. The identification of a Pot1 protein and its encoding DNA also provides a means of developing tools to diagnose illnesses such as cancer that may involve altered expression or structure of a Pot1 protein or gene. Such tools include polynucleotide hybridization probes and antibodies specific for a Pot1 protein.

Accordingly, the invention provides isolated Pot1 proteins having the sequence set forth in SEQ ID NO:13, SEQ ID NO:15, SEQ ID NO:17, SEQ ID NO:9, or SEQ ID NO: 11. Variants of these proteins are capable of binding single-stranded telomeric DNA and have at least 85% sequence identity with, or differ by no more than about 20 single amino acid substitutions, deletions or insertions from, a sequence set forth in SEQ ID NO:13, SEQ ID NO:15, SEQ ID NO:17, SEQ ID NO:9, or SEQ ID NO:11. The invention also provides an isolated, naturally occurring, variant of a protein having the sequence set forth in SEQ ID NO: 13 or in SEQ ID NO:9, which may be a splicing variant. Fragments of the Pot1 proteins of the invention are capable of binding single-stranded telomeric DNA, and comprise the polypeptide having the sequence set forth in SEQ ID NO:5 or SEQ ID NO:6.

The invention further provides an isolated non-genomic polynucleotide encoding one of the aforementioned proteins. A vector comprising such a polynucleotide and a host cell comprising the vector also are provided. The polynucleotide may be included in a pharmaceutical composition, along a pharmacologically acceptable excipient, diluent, or carrier. A method of detecting or measuring the presence of a POT1 polynucleotide comprises contacting the a POT1 polynucleotide, or its complement, with a biological sample from an individual.

An antibody, or a fragment or variant thereof, is provided, which is capable of binding a Pot1 protein. A method of raising the antibody comprises isolating the antibody from an animal or isolating an antibody-producing cell from an animal, following administration of a Pot1 protein, or an antigenic fragment thereof, to the animal. An antibody of the invention may be useful in detecting or measuring the presence of a Pot1 polypeptide in an individual, by contacting the antibody with a biological sample from an individual.

The invention provides a method of increasing the life-span of a cell, by inserting a vector comprising a POT1 polynucleotide into the cell, where the POT1 polynucleotide is operably linked to a promoter that allows the polynucleotide to be transcribed. The vector comprising a POT1 polynucleotide may be administered to an individual in a pharmaceutical composition, comprising the polynucleotide and a pharmacologically acceptable excipient, diluent, or carrier. In one embodiment, the carrier is capable of preferentially delivering the polynucleotide to a specific cell population. In another embodiment, the vector comprising the POT1 polynucleotide is inserted into the cell in vitro, which then may be subsequently administered to an individual. The target cell may express a second polynucleotide that encodes an exogenous protein, such as a therapeutically useful protein.

A method of identifying a compound that interferes with the binding of a Pot1 polypeptide to single-stranded telomeric DNA comprises determining whether the candidate compound decreases the binding of the Pot1 polypeptide to a single-stranded telomeric DNA molecule in a mixture of the single-stranded telomeric DNA molecule, the polypeptide, and the candidate compound. The compound identified by this method may be formulated in a pharmaceutical composition.

A method of decreasing the life-span of a cell comprises reducing the level of Pot1p activity in a cell. The cell may be an immortal cell line, such as a cancer cell. In one embodiment, the method comprises delivering one of the compounds that interferes with the binding of a Pot1 polypeptide to single-stranded telomeric DNA.

Figure 3:
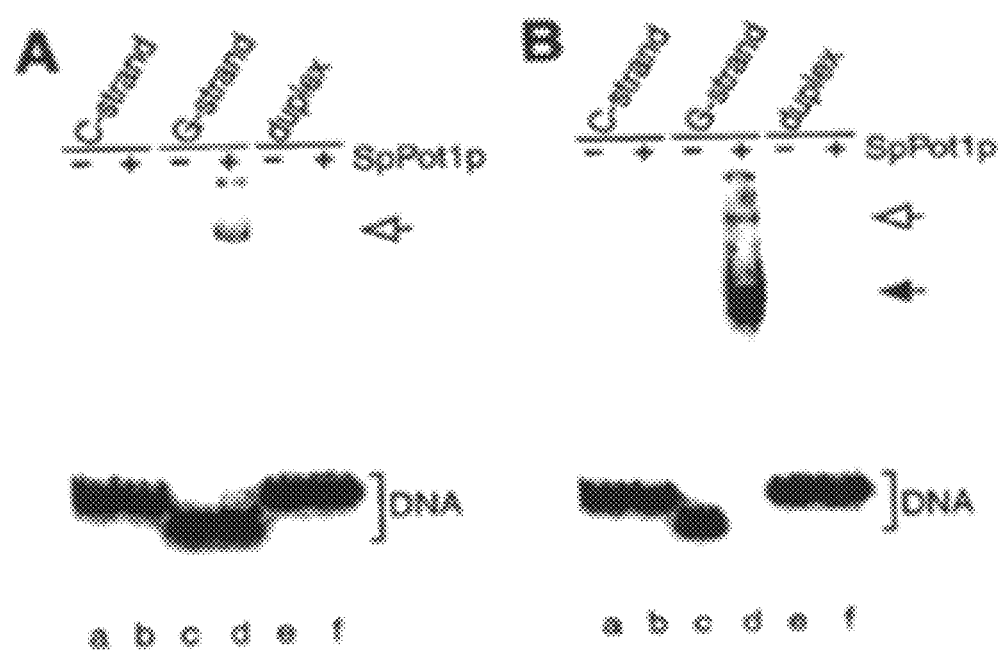
FIG. 3A: DNA-binding specificity of *S. pombe* Pot1p, using conditions described in the Examples. SpPot1p was incubated with the indicated DNA substrates. Complexes were analyzed by nondenaturing gel electrophoresis. The SpPot1p-DNA complex is indicated by an open arrow.
FIG. 3B: Same as FIG. 3A except that the added protein contained truncated Pot1p as well as full length protein. Truncated Pot1p-DNA complex is indicated by a closed arrow.

(TTAGGG)$_5$. Binding conditions and analysis were as described in FIG. 3.

Figure 5:
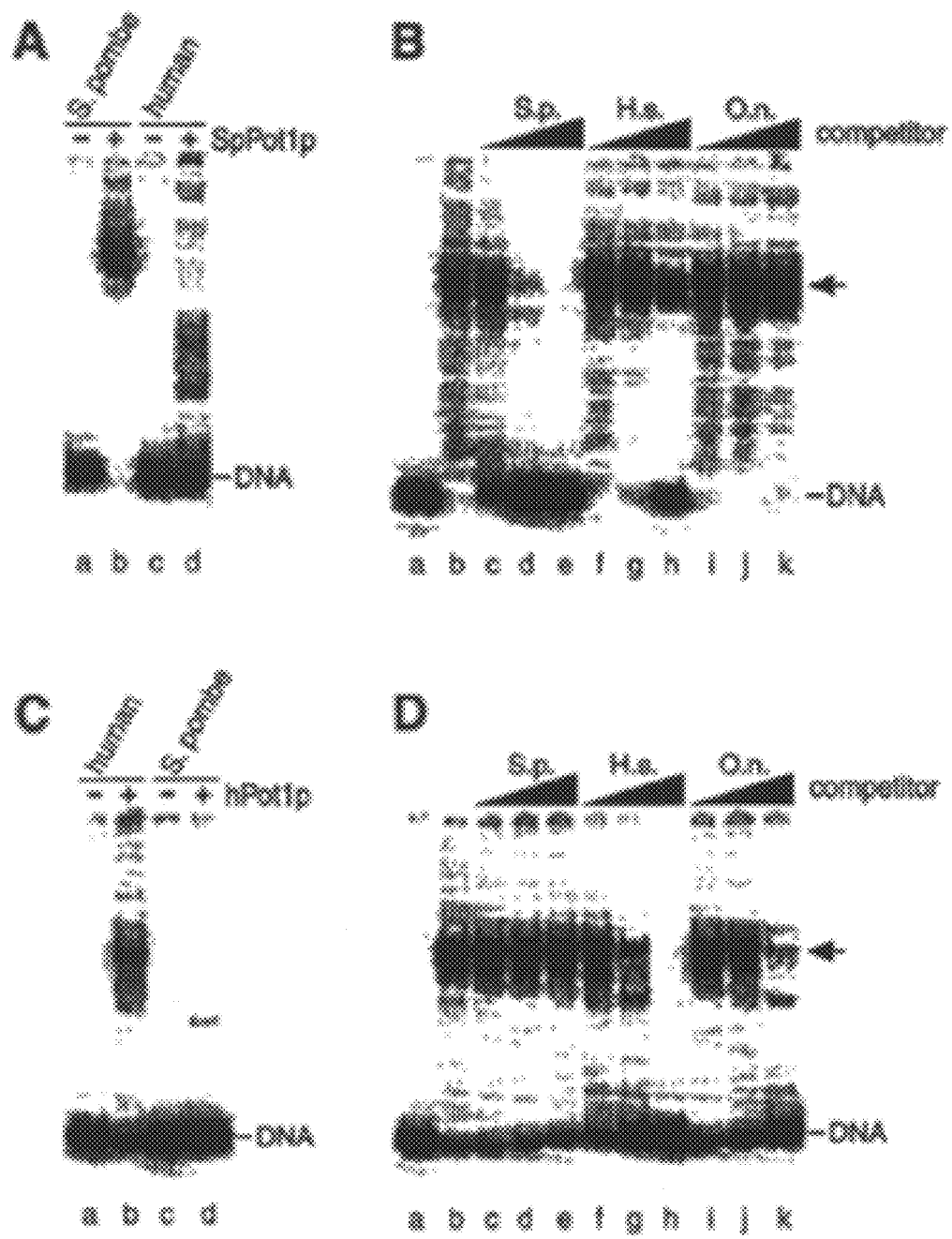

FIG. 5A: Substrate specificity of S. *pombe* and human Pot1p. Binding of SpPot1p to S. *pombe* and human G-strand DNAs.

FIG. 5B: Binding of SpPot1p (50 ng) to radiolabeled S. *pombe* G-strand (1.5 fmol, or 1 ng) in the presence of 10-, 100-, and 1000-fold excess of unlabeled competitor S. *pombe*, human or O. *nova* G-strand DNAs.

FIG. 5C: Binding of hPot1p to S. *pombe* and human G-strand DNAs.

FIG. 5D: Binding of hPot1p to human G-strand DNAs under same conditions as in FIG. 5B.

Figure 6:
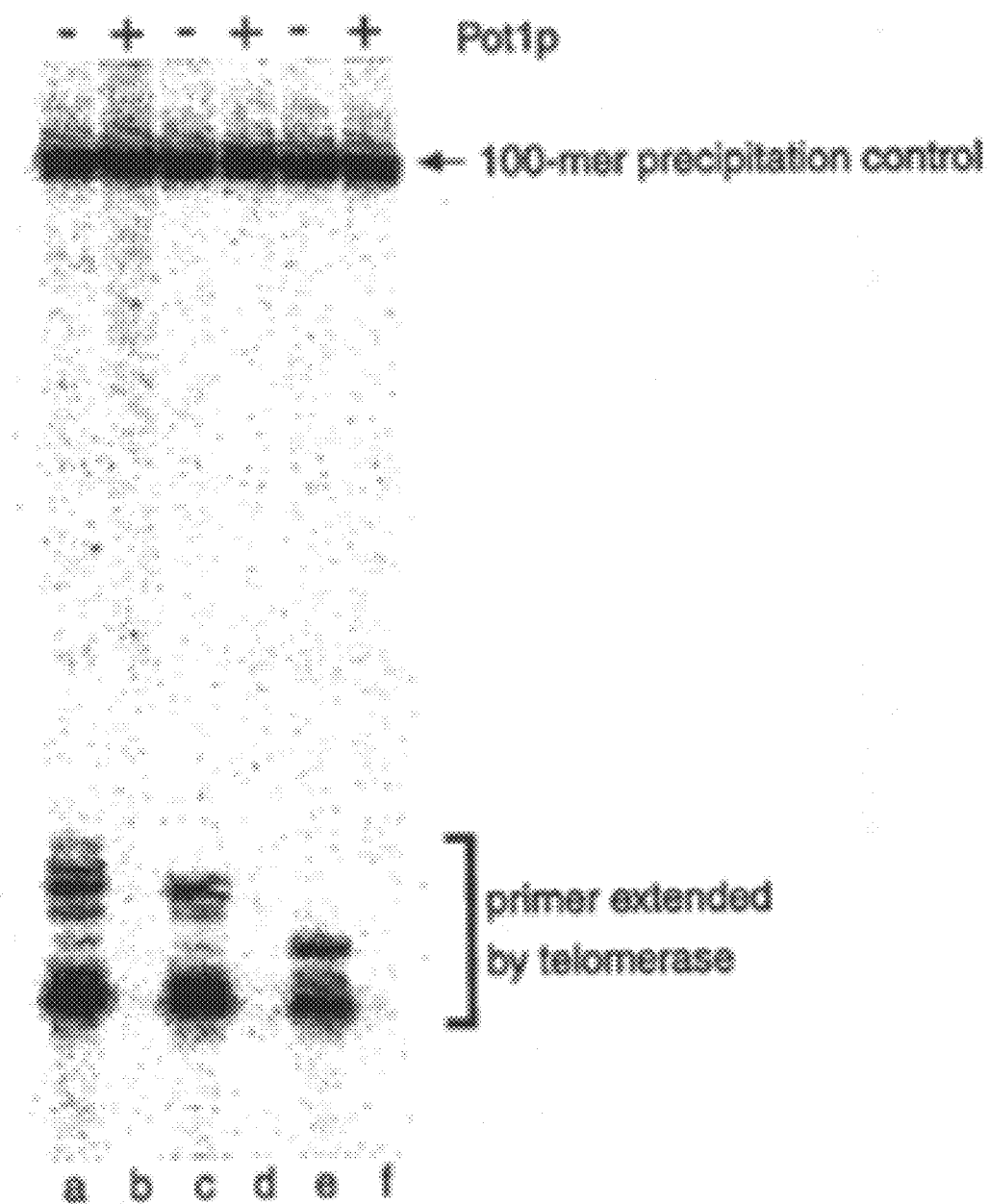

FIG. 6: Inhibition of telomerase activity by Pot1p. Telomerase activity is assayed with telomeric primer PBoli82 (SEQ ID NO: 22) (TGTGGTGTGTGGGTGTGC) as described in Haering et al., Proc. Nat'l Acad. Sci. USA 97: 6367–72, 2000. Unlabeled nucleotides are added to a concentration of 100 µM as follows: lanes a and b, dATP, dCTP and dTTP; lanes c and d, ddATP, dCTP and dTTP; lanes e and f, dATP, dCTP and ddTTP. For lanes b, d, and f the oligonucleotide was preincubated with a SpPot1p preparation containing full length protein and the N-terminal 22 kDa fragment (100 ng/µl). The Pot1 protein inhibits primer extension by telomerase.

FIG. 7: S. *pombe* POT1 genomic DNA. The sequence shown (SEQ ID NO:7) is published by the Sanger Centre as part of cosmid c26H5, having accession number SPAC26H5. The sequence contains an upstream promoter sequence, a coding sequence, which includes two introns, 1 and 2, and a downstream terminator sequence.

FIG. 8A: A S. *pombe* POT1 cDNA sequence (SEQ ID NO:8), in which both introns 1 and 2 have been spliced out.

FIG. 8B: A SpPot1 protein (SEQ ID NO:9) encoded by the DNA sequence of SEQ ID NO:8.

FIG. 8C: A splicing variant of the S. *pombe* POT1 cDNA sequence of SEQ ID NO:8, in which intron 2 has not been spliced out (SEQ ID NO:10).

FIG. 8D: The SpPot1 polypeptide (SEQ ID NO: 11) encoded by the splicing variant of SEQ ID NO:10.

FIG. 9A: A full-length hPOT1 cDNA (SEQ ID NO:12).

FIG. 9B: The hPot1p splicing variant (SEQ ID NO:13) encoded by the polynucleotide of SEQ ID NO:12.

FIG. 9C: Another splicing variant of hPOT1 cDNA (SEQ ID NO:14), having an inserted exon indicated by the underlined residues.

FIG. 9D: The hPot1p splicing variant (SEQ ID NO:15) encoded by the polynucleotide of SEQ ID NO:14. The alternatively spliced exon gives rise to a protein that is about 50% shorter than full-length hPOT1p and has an alternative C-terminus.

FIG. 9E: A splicing variant of hPOT1 cDNA (SEQ ID NO:16). An exon is skipped, giving raise to a hPot1p with an alternate C-terminus.

FIG. 9F: The hpot1p splicing variant (SEQ ID NO:17) encoded by SEQ ID NO: 16.

FIGS. 10A–F: A partial genomic clone of hPOT1 (AC004925; SEQ ID NO:18). Exons are in capital letters.

FIG. 10G: A scale diagram of SEQ ID NO:18, showing the relative position of exons. Exons are numbered arbitrarily, because the clone does not extend to the 5' end of the gene. The exons present in the splicing variants of FIG. 9 are indicated. "Spice variant #1" corresponds to SEQ DI NO:13, "Splice variant #3" corresponds to SEQ ID NO:15, and "Splice variant #3" is SEQ ID NO:17.

DETAILED DESCRIPTION OF THE PREFERRED EMBODIMENTS

The inventors provide a method to control the life-span of a cell. The life-span of a cell depends in part on the ability of a cell to replicate its telomeres with each round of cell division. A Pot1 protein stabilizes chromosomes by binding the single-strand G-rich 3' extension in the telomere, thereby avoiding loss of telomeric DNA and concomitant chromosome fusion or degradation. In the presence of a telomere replication mechanism, such as telomerase or telomeric recombination, Pot1p allows cells to undergo repeated division without reduction in the length of the telomere and attainment of replicative senescence. The isolation of a Pot1 protein and its encoding polynucleotide allows a method of screening for compounds that affect the interaction between Pot1p and telomeric DNA. These compounds will be useful in prolonging or reducing the life span of a cell or population of cells.

Figure 1:
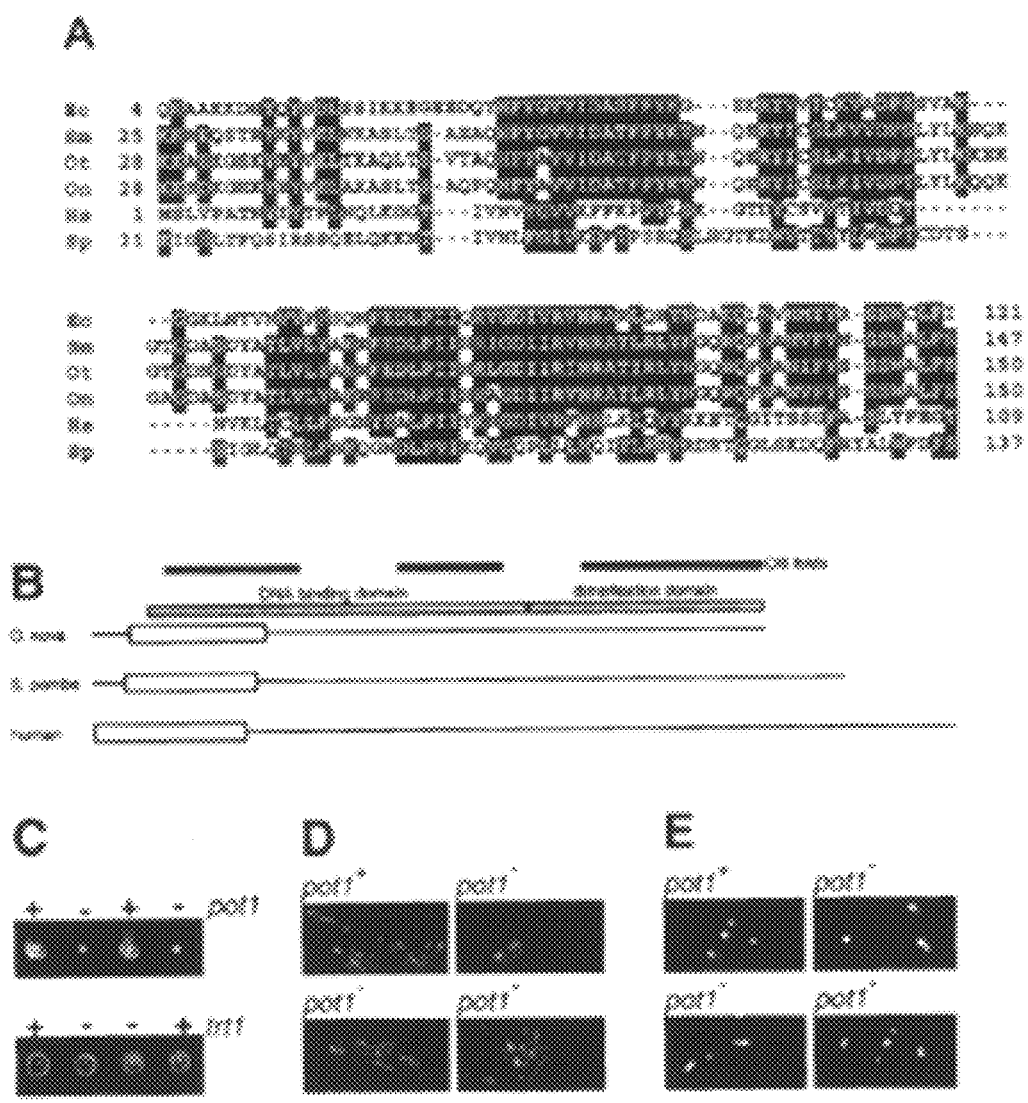
FIG. 1A: Multiple sequence alignments of the N-terminal regions of yeast and human Pot1p and the α subunits of ciliate TEBPs (Ec, *Euplotes crassus* [SEQ ID NO:1]; Sm, *Stylonychia mytilis* [SEQ ID NO:2]; Ot, *Oxytricha trifallax* [SEQ ID NO:3]; On, *Oxytricha nova* [SEQ ID NO:4]; Hs, *Homo sapiens* [SEQ ID NO:5]; Sp, *Schizosaccharomyces pombe* [SEQ ID NO:6]). The numbers of the first and last amino acid shown are depicted at the beginning and end of each sequence. Sequences were aligned in ClustalW using the Blosum35 score table followed by manual adjustment. Shaded amino acids are conserved in 4 or more sequences.
FIG. 1B: Domain structure of the *O. nova* TEBP and yeast and human Pot1p. Position of OB folds (Horvath et al., *Cell* 95: 963–74, 1998) and functional domains (Fang et al., *Genes Dev* 7: 870–82, 1993) are depicted for the *O. nova* TEBP. The position of the regions aligned in FIG. 1A are indicated by open boxes.
FIG. 1C: Morphological phenotype associated with deletion of pot1$^+$. Colony morphology of pot1$^+$, pot1$^-$, trt$^+$ and trt1$^-$ following tetrad dissection and germination.
FIG. 1D: Phase contrast micrographs of pot1$^+$ and pot1$^-$ cells 5 to 10 generations after germination.
FIG. 1E: Cells as in FIG. 1D but stained with DAPI to reveal chromosome segregation defect in pot1$^-$.

The existence of end-capping proteins in humans and S. *pombe* was unforeseen, given the previous inability to find such proteins. The inventors found that S. *pombe* open reading frame SPAC26H5.06 contains a region of modest sequence similarity to the α subunits of TEBP from *Oxytricha nova* and other ciliates (FIG. 1A). Conservation is most apparent over a 95 amino acid stretch near the N-termini of the proteins where the S. *pombe* and O. *nova* sequences share 19% identity and 40% similarity. This region coincides with the most highly conserved domain within the ciliate sequences (42% amino acid identity [61% similarity] between O. *nova* and E. *crassus*). Sequence alignments of hPot1p with the S. *pombe* protein reveals the highest conservation near the N-terminus where the S. *pombe* and human proteins share 48% similarity (26% identity) (FIG. 1A). Over the same region, the similarity of the human sequence with the O. *nova* protein is 39% (23% identity). Such levels of similarity and identity are often found between functionally unrelated proteins, so they are insufficient to indicate homology; therefore, tests of function were performed. No obvious sequence similarity by primary sequence alignment is noted between hPot1p or SpPot1p and cdc13p, the single-stranded telomeric DNA-binding protein of S. *cerevisiae*.

Pot1 Proteins Prevent Chromosomal Instability.

The inventors demonstrate by gene knock-out a role of the S. *pombe* gene, pot1$^+$, in telomere maintenance. A heterozygous diploid pot1$^+$/pot1$^-$ S. *pombe* was constructed by the method described in Baumann and Cech, *Mol Biol Cell* 11: 3265–75, 2000. Tetrad dissections revealed that the pot1$^-$ daughters formed only very small colonies compared to their pot1$^+$ sisters (FIG. 1C). This immediate phenotype is in stark contrast to the observations made with strains lacking the catalytic subunit of telomerase (trt1$^-$), which form wild-type sized colonies upon sporulation (FIG. 1C) and only begin to show a growth defect on the third re-streak, when telomeres have shortened considerably (Nakamura et al., *Science* 282: 493–96, 1998). For approximately 10 generations after sporulation, pot1$^-$ colonies contained a large number of elongated cells, most of which failed to undergo further divisions (FIG. 1D). DAPI staining revealed a high incidence of chromosome missegregation, often leading to daughter cells without any chromosomal DNA (FIG. 1E).

Figure 2:
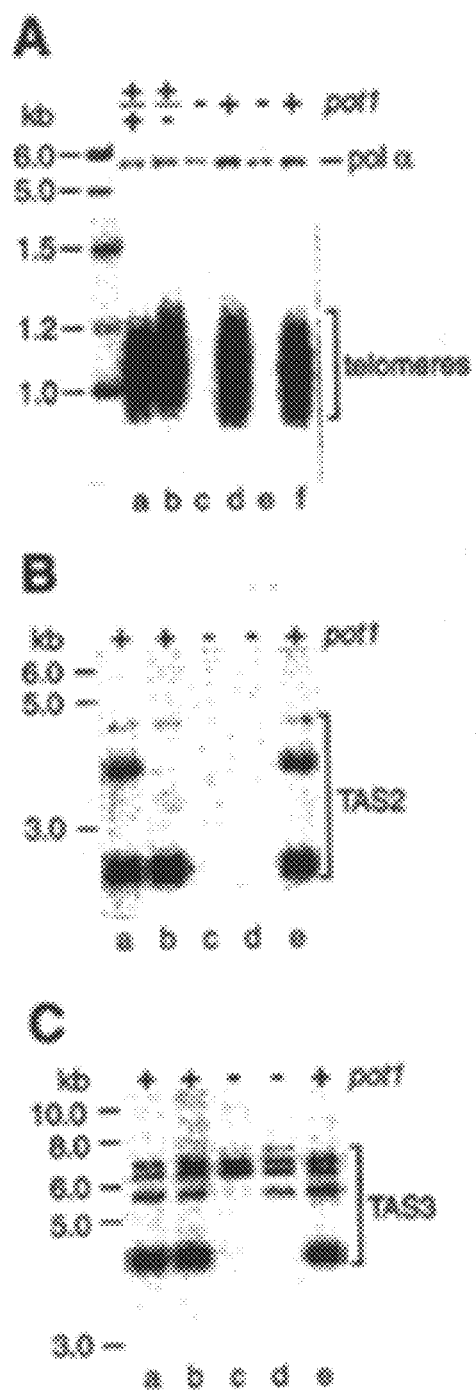
FIG. 2A: Telomere phenotype in pot1$^-$ strains. Genomic DNA from the indicated diploid and haploid strains was digested with Eco RI, which cleaves *S. pombe* DNA about 1.0–1.2 kb from the chromosome ends, and then fractionated by 1.1% agarose gel electrophoresis, transferred to a nylon membrane and hybridized to a telomeric probe. A probe against the single-copy polα gene was used as a loading control.
FIG. 2B: Genomic DNA was digested with NsiI, fractionated by 0.8% agarose gel electrophoresis, transferred to a nylon membrane and hybridized to a probe against Telomere Associated Sequences internal to the telomere itself (TAS2 sequences).
FIG. 2C: The blot shown in FIG. 2B was stripped and hybridized to a probe against Telomere Associated Sequences that are internal to TAS2 (TAS3 sequences).

By deleting the S. *pombe* pot1$^+$ gene, the inventors have shown that a Pot1 protein plays a pivotal role in preventing instability of chromosome ends in vivo. Biochemical and structural data have suggested a role for the Euplotes and Oxytricha TEBPs in protecting the very ends of chromosomes; however, because these organisms are not amenable to genetic studies, proof of such a capping function in vivo has been lacking. This proof is now provided by deletion of the pot1⁺ gene, which leads to immediate chromosome instability (FIG. 2). Telomeres could not be detected by Southern blotting of genomic DNA from pot1⁻ strains (FIG. 2A). Using three DNA probes that recognize distinct subregions of the telomere associated sequence (TAS), hybridization signals were only observed with the telomere distal TAS3 probe (FIG. 2C), but not with TAS1 or TAS2 (FIG. 2B and data not shown). These results indicate that around 5 kb of terminal sequence had been lost within ~30 generations after loss of pot1⁺.

In contrast to the immediate chromosome instability caused by an absence of functional SpPot1p, the absence of functional telomerase causes gradual telomere shortening over many generations without an immediate effect on chromosome stability and cell viability (Nakamura et al., 1998). Thus, at least in *S. pombe*, Pot1p apparently is more important for telomere maintenance in the short term than telomerase.

Pot1 Proteins Specifically Bind Single-Stranded Telomeric DNA.

Pot1 proteins bind directly to single-stranded telomeric DNA. The SpPot1 protein was expressed and purified from *E. coli*, using methodology described below, and the ability of the expressed protein to bind DNA was assayed using an electrophoretic mobility shift assay. SpPot1p interacts specifically with the G-rich strand of *S. pombe* telomeric DNA, but not with the complementary C-rich strand or double-stranded telomeric DNA (FIG. 3A).

Figure 4:
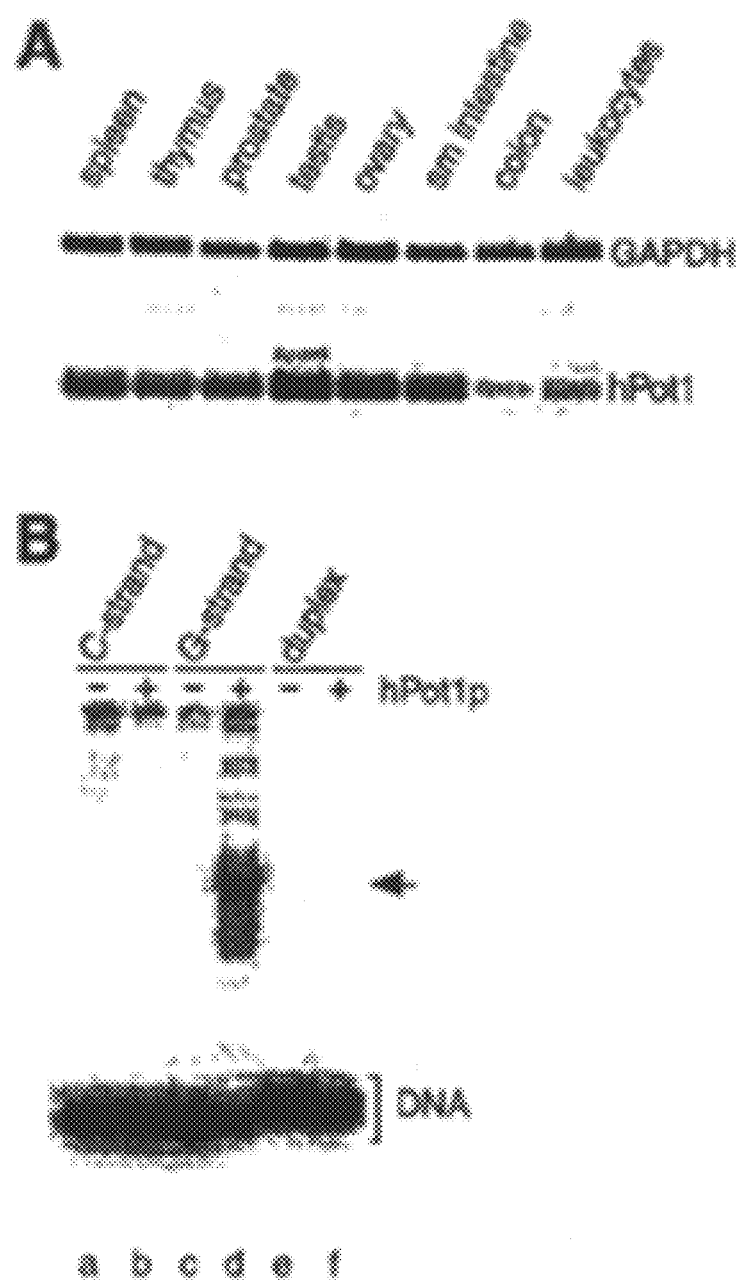
FIG. 4A: Expression of hPOT1 and DNA-binding. RT-PCR amplification of GAPDH and hPOT1 mRNA in various human tissues.
FIG. 4B: Binding of hPot1p to human C-strand (SEQ ID NO: 19) (CCCTAA)$_5$, G-strand (SEQ ID NO: 20) (TTAGGG)$_5$ and duplex (SEQ ID NO: 21) CCCTAA)$_5$•

N-terminal fragments of the SpPot1 protein maintain the ability to bind single-stranded telomeric DNA. Several truncated forms co-eluted with the full length protein from the Ni-NTA column used to purify the expressed SpPot1 protein. These polypeptides retain the N-terminal His₆ tag and thus are believed to arise either from premature termination or from proteolytic degradation of SpPot1p. These truncated proteins had a higher affinity for DNA while retaining the same specificity as displayed by the full length protein (FIG. 3B). Titration experiments indicated that the apparent $K_d$ for binding of a predominant N-terminal fragment of Pot1p to the G-rich oligo is approximately 10 fold higher than for the full length protein (10 nM versus 100 nM). Further purification and analysis by mass spectroscopy showed that the strong shift (indicated by a closed arrow in FIG. 3B, lane d) is attributable to the binding of a 22 kDa N-terminal fragment of SpPot1p. Increased DNA binding likewise has been observed with N-terminal fragments of the a subunit of TEBP from *Oxytricha nova* (Fang et al., 1993).

hPot1p N-terminal fragments show the same behavior as SpPot1p fragments. hPot1p, like SpPot1p, often lacks C-terminal sequences due to degradation or premature termination. These truncated forms of hPot1p also show the same DNA binding specificity as full length hPot1p obtained from in vitro translation reactions. In gel shift assays, hPot1p binds G-rich strands of human telomeric DNA (FIG. 4B). As with SpPot1p, binding was not observed with the complementary C-rich strand or with double-stranded telomeric DNA.

SpPot1p and hPot1p both bind specifically to telomeric DNA. That is, binding of both SpPot1p and hPot1p was unaffected by the presence of a 60-fold excess of herring sperm DNA and 2000-fold excess of an oligonucleotide of non-telomeric sequence. To further investigate the sequence specificity, G-rich strands of telomeric DNA from different species were tested as substrates in DNA-binding assays. In a side-by-side comparison, SpPot1p bound the human telomeric sequence (GGGTTA repeat) with a lower affinity than the *S. pombe* telomeric sequence (repeating units of the consensus sequence GGTTACA) (FIG. 5A). In competition experiments, a 1000-fold excess of unlabeled *S. pombe* sequence abolished binding to the radiolabeled substrate, whereas the human and *O. nova* DNA competitors reduced binding by only ~50% and <2%, respectively (FIG. 5B). Similarly, hPot1p showed only weak binding to the *S. pombe* sequence (FIG. 5C), which also was not an efficient competitor (FIG. 5D). In contrast, the presence of a 1000-fold excess of the *O. nova* sequence reduced binding to less than 25%. Accordingly, both SpPot1p and hPot1p specifically bind telomeric DNA, and each shows a higher affinity for telomeric DNA from their own species.

Pot1p binds a variety of related telomeric DNA sequences. Oligonucleotides that form a DNA-Pot1p complex, as determined by an electrophoretic mobility shift assay, are shown in Table I, below. The affinity between Pot1p and the oligonucleotide varies with the particular sequence (data not shown).

TABLE I

SpPot1p-binding oligonucleotides:
(SEQ ID NOS 23–25, respectively, in order of appearance)

| | |
|---|---|
| PBoli52 | GGT TAC GGT TAC AGG TTA CA |
| PBoli53 | CGG TTA CAC GGT TAC AGG T |
| PBoli54 | GTT ACA GGT TAC GGT TAC GG |
| PBoli86 | TGT GGT GTG TGG GTG TGC GGT T |
| PBoli110 | GGT TAC ACG GTT ACA GGT TAC AGG TTA CAG |
| PBoli112 | GGT TAC ACG GTT ACA GGT TAC AGG TTA CAG GGT TAC GGT TAC G |
| PBoli183 | CTG TAA GCA TAT CAT CAT TCG A GGT TAC |
| PBoli184 | GGT TAC GCA TAT CAT CAT TCG A ATC TCG |
| PBoli185 | CTG TAA GCA TAT CAT CGG TTA CGG TTA C |
| PBoli186 | GGT TAC GGT TAC CAT CAT TCG A ATC TCG |
| PBoli187 | CTG TAA GCA TAT GGT TAC TCG A ATC TCG |
| PBoli188 | CTG TAA GC GGT TAC GGT TAC GA ATC TCG |
| PT1 | GGT TAC AGG TTA CAG GTT AC | hPot1p-binding oligonucleotides:

(SEQ ID NOS 36–38, respectively, in order of appearance)

| | |
|---|---|
| PBoli177 | TTA GGG TTA GGG TTA GGG TT |
| PBoli178 | GG TTA GGG TTA GGG TTA GGG |
| PBoli179 | TTA GGG TTA GGG TTA GGG TTA GGG TTA GGG | hPOT1 mRNA is detected in all tissues examined, although a high steady-state level of hPOT1 mRNA is observed in testis and lower levels are observed in colon, skeletal muscle, and peripheral blood lymphocytes (FIG. 5A and data not shown). In contrast with mRNA levels of human TERT, which correlate with cellular immortality and proliferative activity, the presence of hPOT1 mRNA in all tissues examined is consistent with hPOT1 being a house keeping gene, required to ensure the integrity of chromosome ends independently of the proliferative state of cells.

Screening Methods to Identify Useful Compounds that Affect the Interaction of Pot1p with Single-Stranded Telomeric DNA.

The use of routine screens to find inhibitors and activators of Pot1p is facilitated by providing a polynucleotide that encodes a Pot1 protein, which allows Pot1p to be expressed recombinantly. Pot1p thus may be expressed in vitro or in a host cell, such as *E. coli*, yeast, or bacullovirus-infected insect cells, and tested against candidate compounds. Useful compounds will be those that affect the binding between a Pot1 polypeptide and telomeric DNA, especially the G-rich single-stranded component.

The interaction between Pot1p and telomeric DNA is readily assayed in vitro, by a number of routine methods that are well known to the artisan. In vitro assays can be configured as high throughput assays, to test candidate molecules simultaneously. In one embodiment, such assays can be designed around the electrophoretic mobility shift assays described in the examples.

Candidate molecules that will be useful for the invention generally will include small organic compounds that interact with a Pot1 protein or a Pot1 protein-DNA complex to change the binding constant. In one embodiment, candidate molecules are rapidly identified by their ability to change the amount of labeled probe that interacts with a Pot1 protein in vitro. Candidates with possible activity are then further analyzed to determine an apparent binding constant, which is compared to that of the control reaction lacking a candidate molecule, to determine whether the particular compound strengthens or weakens the interaction between Pot1p and the telomere. Promising candidates may be subsequently analyzed in a cell culture system, to analyze the effect of the candidate molecule on telomere length or integrity throughout repeated cell divisions. The examples describe a number of tests that can be used to assay the role of Pot1p on telomere structure.

Likely candidate compounds that will inhibit the interaction between a Pot1 polypeptide include compounds that can act as a substrate analogue. Since the substrate for a Pot1 protein is telomeric DNA, such compounds include single-stranded DNA comprising TTAGGG repeats, when used to inhibit a hPot1 protein or single-stranded DNA comprising GGTTACA repeats, when used to inhibit a SpPot1 protein. FIG. 5B, lanes d–e, and FIG. 5D, lanes g–h and k provide in vitro proof of principle of the efficacy of such inhibitors. The oligonucleotides listed in TABLE I represent a variety of useful compounds with a known ability to act as substrate analogues. Thus, these oligonucleotides themselves, or analogues of these oligonucleotides with advantageous pharmacological properties, will be useful compounds for the inhibition of Pot1p activity.

Preferred analogues of these oligonucleotides are non-hydrolyzable DNA analogues that have increased pharmacological longevity and efficacy. One DNA analogue with enhanced stability relative to DNA is a peptide nucleic acid (PNA) molecule that comprises a Pot1 protein binding site. Such molecules, along with methods of their formulation and delivery, are generally described in U.S. Pat. No. 6,046,307.

Candidate molecules that will be useful for the invention may also include small organic compounds that modulate telomerase activity. These compounds may be administered in combination with compounds that regulate Pot1p activity. Alternatively, these compounds themselves are candidates for regulators of Pot1p activity, and their possible effect on Pot1p activity can be determined by the screening methods of the invention. These compounds are described in U.S. Pat. Nos. 6,194,206, 6,156,763, 6,110,955, or 6,054,442, for example.

Methods to Extend the Life-Span of Cells.

The inventors have shown that chromosome of cells lacking Pot1p activity are susceptible to rapid disorganization and destabilization. Pot1p thus maintains telomere structure and function, which provides a means of therapeutic intervention in cases where it is desirable to alter telomere structure and function. Methods are provided alternatively to stabilize or to destabilize telomere structure, depending on the desirability of prolonging the proliferative capacity, or life-span, of the cell in question. "Proliferative capacity" and "life-span" both are used in this context in terms of how many times a cell can divide before it enters replicative senescence.

Enhancing the activity of a Pot1 protein in a cell advantageously can stabilize telomeres and thereby prolong the life-span of the cell. Examples of suitable target cells include those that are genetically engineered to produce a desired protein or those that produce useful antibodies. Other desirable target cell types include isolated stem cells, especially where disease otherwise would deplete various stem cell populations. Additional advantageous target cells include cells that proliferate in response to repeated tissue injury, such as endothelial cells, or cells whose functions are susceptible to aging or disease, such as CD4+ cells, connective tissue fibroblasts, or cells affected by age-related macular degeneration.

Pot1p activity can be increased in a number of ways in these desired target cells. In one method, Pot1p activity is increased by transfecting the cell with an expression construct that encodes a Pot1 protein. In this embodiment, the "effector compound" is an expression vector that directs high level or regulated expression of a Pot1 polypeptide. The expression causes higher levels of Pot1p to accumulate in the target cell, thereby increasing the overall level of Pot1p activity or replacing Pot1p lost through genetic mutation. In another method, the cell is treated with a small effector compound that stabilizes the interaction between Pot1p and telomeric DNA. In either case, the effector compound may be added to a cell ex vivo to affect Pot1p expression, followed by administration of the cell to the individual undergoing treatment. Alternatively, the effector compound may be administered to the cell in vivo. In this case a preferable means of administration directs or targets the effector compound to the desired cell. Suitable means of cell targeting are known in the art, and include liposome encapsulation and antibody-directed targeting, or combinations of these two.

In some instances, it may be desirable to increase Pot1p expression temporarily. When an effector compound is administered in vivo, this control typically can be achieved simply by discontinuing administration. Where Pot1p expression is increased through recombinant engineering, on the other hand, it may be desirable to control Pot1p expression with an inducible or regulated promoter. Expression then can be induced for as long as desired by administering the appropriate inducer or regulatory compound.

By contrast, an inhibitor of Pot1 protein function will be useful in shortening the life-span of cells, whose presence is undesirable, through the destabilization of telomere structure and function. Such cells include those that are immortalized by aberrant expression of telomerase, as in many cancer cell lines. Inhibitors may be delivered to the entire body, as is currently common in chemotherapeutic methods. Because Pot1p is expressed in a variety of cell types in humans, and may be expressed ubiquitously, the amount of administered inhibitor must be carefully monitored to prevent adverse side-effects to other non-targeted cell types that express Pot1p. As an alternative or supplement to whole-body delivery, localized delivery may be employed. For example, inhibitors can be formulated as a depot for internal delivery to the site of a tumor. In another embodiment, inhibitors may be targeted to a specific population of cells by one of the many available means of cell targeting, such as immunotargeting.

Parasitic or pathogenic cells, e.g. yeast, whose proliferation or life-span may be controlled by regulating telomere length, also are desirable targets for Pot1p inhibitors.

Accordingly, one embodiment of the invention is a method of controlling yeast infection through administration of a therapeutically effective amount of a Pot1p inhibitor.

FIG. 6 demonstrates the ability of Pot1p to inhibit telomerase action. Pot1p is believed to inhibit telomerase activity through the formation of a Pot1p-telomeric DNA complex. Compounds which strengthen or weaken this complex thus are expected to affect the level of telomerase activity in a cell. In one embodiment of the invention, a method in which Pot1p activity is increased in a cell, such as by recombinant expression of a POT1 polynucleotide, is combined with the administration of a compound that inhibits telomerase activity. A variety of telomerase inhibitors are known in the art, as described in U.S. Pat. No. 6,156,763, for example.

Pot1 Polypeptides.

The skilled artisan will appreciate that useful variants of a Pot1 protein include those that maintain the capability of binding single-stranded telomeric DNA. These variants will be useful, for example, in methods of screening for compounds that affect the ability of a Pot1 protein to interact with single-stranded DNA. Other useful protein variants may not exhibit DNA-binding activity, but may be useful for other purposes. Such purposes include raising antibodies that specifically bind a Pot1 protein, such as a non-functional, naturally occurring mutation of Pot1p. Such purposes also include the identification of dominant negative inhibitors that bind other cellular proteins that normally interact with Pot1p. Variants may occur naturally or may be created by modifying the primary sequence of the protein through manipulation of a polynucleotide encoding a Pot1 protein. "Protein" and "polypeptide" are used interchangeably throughout.

"Variants" of an hPot1 and SpPot1 protein include naturally occurring allelic variations of hPot1p and SpPot1 proteins, a fragment of a Pot1 protein that binds single-stranded telomeric DNA, or a fragment thereof that elicits an antigenic response when administered to a host animal. Variants also include polypeptides that have a modified amino acid sequence from the aforementioned polypeptides. Because protein function depends on three-dimension structure, skilled artisan will recognize that variants bearing the closest structural relationship to hPot1p and SpPot1p are most likely to preserve biological function. Sequence modifications include amino acid substitutions, insertions, and deletions. Amino acid insertions and deletions may be made in the interior of the protein sequence, as well as at the amino and carboxyl termini. Guidance in determining which and how many such sequence modifications may be made without abolishing biological or antigenic activity may be found using computer programs well known in the art, for example, DNAStar software.

The sequence of variants preferably will have an 80% identity to the full-length hPot1p and SpPot1 proteins. More preferably, variants will have at least about 85% identity to the full-length sequences. Even more preferably, the percent identity will be at least about 90%, and most preferably, the percent identity will be at least about 95%, or even 98%. Likewise, variants of fragments of hPot1p and SpPot1 proteins will be useful for the invention, for instance, as antigenic fragments. Such variants will have at least about 85% identity to fragments of the hPot1p and SpPot1 proteins. Even more preferably, the percent identity will be at least about 90%, and most preferably, the percent identity will be at least about 95%, or even 98%. Preferably, antigenic fragments will be 5, 10, 15, 20, or 30 amino acids in length. A preferred biologically active Pot1p fragment folds into DNA-binding domain. Biologically active fragments include the N-terminal fragments of Pot1p identified by gel shift assays, including the 22 kDa fragment of SpPot1p.

Variants may also include "splicing variants." It is well-known that, within a given eukaryotic gene, sequences that encode the polypeptide gene product are non-contiguous. The protein coding sequences, or exons, are divided by intervening non-coding sequences, known as introns. These introns are transcribed but then spliced out during maturation of the mRNA. Exons often correspond to functional domains of the protein product. Go, *Nature* 291:90–92 (1981); Branden et al., *EMBO J.* 3:1307–10 (1984).

Exons themselves may be spliced out during the maturation of the mRNA. In some cases, two exons may be mutually exclusive in the mature mRNA. Deletion or swapping of exons is known as alternative splicing. Andreadis et al., *Ann. Rev. Cell Biol.* 3:207–42 (1987). The family of proteins produced by alternatively spliced mRNAs exhibit different functional properties, depending on which exons are present in the mature mRNA. Typically, alternative splicing is regulated in a tissue-specific manner and involves only one or a few exons within a gene.

Thus, the polynucleotides of the invention encompass variants that differ by the addition, deletion or alternative splicing of exons. In general, exons alternatively added to the 5' or 3' termini of the open reading frame are encompassed by "addition" variants, whereas alternatively spliced exons that contribute additional coding sequences within the open reading frame are encompassed by "insertion" variants.

Specific splicing variants encompassed by the invention are shown in the Figures. The SpPOT1 gene, for example, has two introns, which normally are spliced from the mature transcript. However, in one splicing variant, intron 2 may not be spliced, so that it is included in the mature transcript (SEQ ID NO: 10). Because the intron does not contain a stop codon, the splicing variant mRNA gives rise a somewhat larger polypeptide (compare SEQ ID NO:9 and 11). When intron 1 is not spliced out, however, the resulting protein is truncated as a result of a stop codon within intron 1. The resulting peptide has the sequence:(SEQ ID NO:39)M G E D V I D S L Q L N E L L N A G E Y K I G V R Y Q W I Y I C F A N N E K G T Y I S V H. Alternatively, translational frame shifting may lead to a significantly larger protein product. Translational frame shifting has been observed in a number of proteins involved in telomere metabolism. Aigner et at., *EMBO J.* 19: 6230–39, 2000. Polypeptides resulting from translational frame shifting also are considered "splicing variants" for the purposes of the invention.

A more complex pattern of splicing variants is observed in hPOT1 polynucleotides. In one splice variant, exon 5 is not incorporated into the mature transcript (see FIG. 10G for nomenclature). The resulting polypeptide is 72 kDa in size and is shown in FIG. 9B (SEQ ID NO:13). When exon 5 is included in the mature transcript, the resulting protein is an N-terminal fragment that is 38 kDa in size, because of the presence of a stop codon within exon 5 (SEQ ID NO:15). When the mature transcript lacks exons 5 and 10, it gives rise to another N-terminal fragment 58 kDa in size. Additional variants may arise from translational frame shifting, as well.

Additional polypeptide sequences or other moieties, such as covalently attached detectable tags, may be added to the proteins of the invention. Additional polypeptide sequences may fused to either the amino or carboxyl termini of the polypeptides of the invention, and they may be useful, for example, in assisting the expression, purification, and/or detection proteins of the invention. For example, these various sequences include those well known in the art that are useful in purification of recombinantly expressed proteins. A preferred fusion protein, which the inventors have reduced to practice, comprises a "His$_6$ tag" sequence, which facilitates purification of the recombinantly expressed protein. A preferred purification system is the TALON™ non-denaturing protein purification kit for purifying His$_6$-tagged proteins under native conditions (CLONTECH, Palo Alto, Calif.).

"Isolated" polypeptides of the invention have been purified to remove at least some portion of cellular or non-cellular molecules with which the proteins are associated naturally. Isolated proteins include those that are partially purified or enriched, as well as those purified to homogeneity. Isolated proteins also include those produced artificially, such as by recombinant expression or by in vitro translation. The isolated protein may be included in compositions containing other polypeptides for specific purposes, for example, as stabilizers.

"Substitutions, insertions, additions and deletions" refer to changes in a particular polypeptide sequence, or any one its naturally occurring splicing variants. "Substitutions" generally refer to alterations in the amino acid sequence that do not change the overall length of the polypeptide, but only alter one or more amino acid residues, substituting one for another in the common sense of the word. Generally speaking, the number of amino acid substitutions for any given variant will not be more than about 20, 10, 5, or 3, such as 1–20 or any range or value therein. Substitutions preferably are conservative, such that one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

"Insertions" add extra amino acids to the interior (not the amino- or carboxyl-terminal ends) of the subject polypeptide. Insertions include amino acids encoded by exons that are alternatively spliced into a polypeptide, such as the splicing variants shown in FIGS. 8 and 9. "Deletions" diminish the overall size of the polypeptide by removal of amino acids from the interior or either end of the polypeptide. In one embodiment, deletions remove less than about 30% of the size of the subject molecule. Other preferred deletions include naturally occurring splicing variants of a Pot1 protein, such as those described above. These variants may be fragments of the size the full-length protein, which may be considerably smaller than 30% the size of the full-length protein.

"Additions," like insertions, also add to the overall size of the protein; however, instead of being made within the molecule, they are made on the N- or C-terminus of the encoded protein. Unlike deletions, additions may be of virtually any size; however, preferred additions do not exceed about 100% of the size of the native molecule. "Additions" also to encompass adducts to the amino acids of the native molecule.

In general, both the DNA and protein molecules of the invention can be defined with reference to "sequence iden-tity." As used herein, "sequence identity" refers to a comparison made between two molecules using standard algorithms well-known in the art. Although any sequence algorithm can be used to define "sequence identity," for clarity, the present invention defines identity with reference to the Smith-Waterman algorithm, where the open reading frame generally is used as the reference sequence to define the percentage identity of polynucleotide homologues over its length. When "sequence identity" is used with reference to a polypeptide, the designated polypeptide is used as a reference sequence over its length.

The choice of parameter values for matches, mismatches, and inserts or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and ⅓ for a mismatched residue (a residue being either a single nucleotide or a single amino acid). Insertions and deletions ("indels"), x, are weighted as:

$$x_k=1+k/3,$$

where k is the number of residues in a given insert or deletion (Waterman, *Bulletin of Mathematical Biology* 46:473–500 (1984)).

Polynucleotides of the Invention.

Polynucleotides of the invention are those that encode Pot1 proteins or their fragments and derivatives. These polynucleotides include those that encode SpPot1 polypeptides. An *S. pombe* genomic DNA sequence is described by the Sanger Centre as part of cosmid clone c26H5, having accession number SPAC26H5 (SEQ ID NO:7). This sequence contains an upstream promoter region, a coding region with two introns, and a downstream region that contains a terminator. Both upstream and downstream regions may play a role in the regulation of SpPot1p expression. The introns can be alternatively spliced, as described above (SEQ ID NOS:8 and 10). Preferred polynucleotides are non-genomic; i.e., they correspond to transcripts from genomic DNA. An example of non-genomic DNA is a mRNA or cDNA encoding the polypeptides of SEQ ID NO: 9 or SEQ ID NO:11.

The polynucleotides of the invention also include those that encode a hPot1p and its variants and fragments. A partial genomic clone is described for human POT1, having accession number AC004925 (SEQ ID NO:18). This partial genomic clone contains nine exons, shown diagrammatically in FIG. 10G. Of these exons, at least exons 5 and 10 can be alternatively spliced (compare SEQ ID NOS:12, 14, and 16). Various cDNA sequences encoding full-length hPot1p have been described: FLJ10368 (submitted Feb. 22, 2000), FLJ11073 (submitted Feb. 22, 2000), FLJ12518 (submitted Sep. 29, 2000), BC002923 (submitted Feb. 5, 2001), and NM_015450 (submitted Feb. 26, 2001). Various other partial cDNA sequences and ESTs that encode portions of hPot1 protein also have been described: FLJ22851 (submitted Sept. 29, 2000), AL050120 (submitted Feb. 18, 2000). Of the hPOT1 polynucleotides presently described, only the hPOT1 cDNA of SEQ ID NO:12 closely resembles the sequences described in FLJ10368, FLJ11073, and FLJ12518.

The invention also provides a nucleic acid molecule having a sequence complementary to one of the above sequences. Such isolated nucleic acid molecules are useful as probes for gene mapping by in situ hybridization with chromosomes. They are particularly useful for detecting transcription of a POT1 gene in human tissue, or transcripts of naturally occurring homologues that may themselves be therapeutically useful.

The polynucleotides of the invention may also be useful for detecting transcripts of naturally occurring POT1 variants occurring in disease states. The present polynucleotides thus may have diagnostic application in differentiating normal and abnormal genes, based on differential hybridization, as discussed in more detail below. Alternatively, a diagnostic application may include differentiating abnormally high or low levels of expression of a normal gene.

Isolated nucleic acid molecules of the present invention include nucleic acid molecules comprising the coding sequence for a Pot1 protein, and nucleic acid molecules which comprise a nucleotide sequence substantially different from those described above but which, due to the degeneracy of the genetic code, still encode at least one Pot1 protein as described and enabled herein. Of course, the genetic code is well-known in the art. Thus, it would be routine for one skilled in the art to generate such degenerate nucleic acid variants that code for specific Pot1 proteins of the present invention. See, e.g., Ausubel, et al.

The term "hybridization" refers to formation of double stranded polynucleotides through complementary nucleotide base pairing. High stringency hybridization occurs at a temperature between about 65° C. and 70° C. in a hybridization solution of 6× SSC, 0.5% SDS, 5× Denhardt's solution and 100 μg of non-specific carrier DNA. The preferred probe is 100 bases selected from contiguous bases of the polynucleotide sequence set forth in SEQ ID NO:1. A high stringency wash solution contains the equivalent in ionic strength of less than about 0.2× SSC and 0.1% SDS, with a preferred stringent solution containing about 0.1× SSC and 0.1% SDS. High stringency washing conditions comprise washing with 2× SSC with 0.05% SDS five times at room temperature, then washing with 0.1× SSC with 0.1% SDS at 68° C. for 1 h. Blots containing the hybridized, labeled probe are exposed to film for one to three days.

"Isolated" nucleic acid molecules are removed from their native or naturally occurring environment. For example, recombinant nucleic acid molecules in a vector and/or a host cell are considered isolated for the purposes of the present invention. Isolated RNA molecules include in vivo or in vitro RNA transcripts of the nucleic acid molecules of the present invention. Isolated nucleic acid molecules according to the present invention further include such molecules produced synthetically or purified from cells containing such nucleic acids, where the nucleic acid is in other than a naturally occurring form. Isolated nucleic acid molecules include genomic DNA that has been removed from the chromosome in which it occurs naturally.

Vectors of the Invention.

The term "vector" refers to a nucleic acid compound used for introducing exogenous nucleic acid into host cells. A vector comprises a nucleotide sequence which may encode one or more polypeptide molecules. Plasmids, cosmids, viruses, and bacteriophages, in a natural state or which have undergone recombinant engineering, are non-limiting examples of commonly used vectors to provide recombinant vectors comprising at least one desired isolated nucleic acid molecule.

The term "promoter" refers to a nucleic acid sequence that directs the initiation of transcription. An inducible promoter is one that is regulated by environmental signals, such as carbon source, heat, or metal ions.

"Host cell" refers to any eukaryotic, prokaryotic, or other cell that is suitable for propagating and/or expressing an isolated nucleic acid that is introduced into the host cell by any suitable means known in the art. The cell can be part of a tissue or organism, isolated in culture or in any other suitable form.

The present invention further provides recombinant expression cassettes comprising a nucleic acid of the present invention, and operably linked to transcriptional initiation regulatory sequences that will direct the transcription of the polynucleotide in the intended host cell. Both heterologous and endogenous promoters can be employed to direct expression. These promoters can also be used, for example, in recombinant expression cassettes to drive expression of antisense nucleic acids to reduce Pot1p content in a desired tissue.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution. Suitable promoters include the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiation codon at the beginning and a termination codon (UAA, UGA or UAG) appropriately positioned at the end of the polypeptide to be translated.

The polynucleotides can optionally be joined to a vector containing a selectable marker for propagation in a host. Such markers include, e.g., dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art. Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Sambrook, supra, Chapters 1–4 and 16–18; Ausubel, supra, Chapters 1, 9, 13, 15, 16.

Recombinant Protein Expression.

The polypeptide can be expressed in a modified form, such as a fusion protein, and can include not only secretion signals, but also additional heterologous functional regions. For instance, a region of additional amino acids, particularly charged amino acids, can be added to the N-terminus of a polypeptide to improve stability and persistence in the host cell, during purification, or during subsequent handling and storage. Also, peptide moieties can be added to a polypeptide to facilitate purification. Such regions can be removed prior to final preparation of a polypeptide. The addition of peptide moieties to polypeptides to engender secretion or excretion, to improve stability and to facilitate purification, among others, are familiar and routine techniques in the art. Such methods are described in many standard laboratory manuals, such as Sambrook, supra, Chapters 17.29–17.42 and 18.1–18.74; Ausubel, supra, Chapters 16, 17 and 18.

A Pot1 polypeptide can be recovered and purified from recombinant cell cultures by well known methods. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Polypeptides of the invention can also include an initial modified methionine residue, in some cases as a result of host-mediated processes. The monitoring of the purification process can be accomplished by DNA-binding activity assays, Western blot techniques, radioimmunoassay, or other standard immunoassay techniques. These methods are described in many standard laboratory manuals, such as Sambrook, supra, Chapters 17.37–17.42; Ausubel, supra, Chapters 10, 12, 13, 16, 18 and 20.

Antibodies of the Invention.

Antibodies raised against the proteins and protein fragments of the invention also are contemplated by the invention. In particular, the invention contemplates antibodies raised against Pot1p, and variants thereof. Described below are antibody products and methods for producing antibodies capable of specifically recognizing one or more epitopes of the presently described proteins and their derivatives. Antibodies include, but are not limited to polyclonal antibodies, monoclonal antibodies (mAbs), humanized or chimeric antibodies, single chain antibodies including single chain Fv (scFv) fragments, Fab fragments, F(ab')$_2$ fragments, fragments produced by a Fab expression library, anti-idiotypic (anti-Id) antibodies, epitope-binding fragments, and humanized forms of any of the above.

As known to one in the art, these antibodies may be used, for example, in the detection of a target protein in a biological sample. They also may be utilized as part of treatment methods, and/or may be used as part of diagnostic techniques whereby patients may be tested for abnormal levels or preferably for the presence of abnormal forms of the proteins.

In general, techniques for preparing polyclonal and monoclonal antibodies as well as hybridomas capable of producing the desired antibody are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21 (1980); Kohler and Milstein, *Nature* 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96).

i) Polyclonal Antibodies.

Polyclonal antibodies are heterogeneous populations of antibody molecules derived from the sera of animals immunized with an antigen, such as an inventive protein or an antigenic derivative thereof. Polyclonal antiserum, containing antibodies to heterogeneous epitopes of a single protein, can be prepared by immunizing suitable animals with the expressed protein described above, which can be unmodified or modified, as known in the art, to enhance immunogenicity. Immunization methods include subcutaneous or intraperitoneal injection of the polypeptide.

Effective polyclonal antibody production is affected by many factors related both to the antigen and to the host species. For example, small molecules tend to be less immunogenic than others and may require the use of carriers and/or adjuvant. In addition, host animal response may vary with site of inoculation. Both inadequate or excessive doses of antigen may result in low titer antisera. In general, however, small doses (high ng to low $\mu$g levels) of antigen administered at multiple intradermal sites appears to be most reliable. Host animals may include but are not limited to rabbits, mice, and rats, to name but a few. An effective immunization protocol for rabbits can be found in Vaitukaitis, J. et al., *J. Clin. Endocrinol. Metab.* 33:988–991 (1971).

The protein immunogen may be modified or administered in an adjuvant in order to increase the protein's antigenicity. Methods of increasing the antigenicity of a protein are well known in the art and include, but are not limited to coupling the antigen with a heterologous protein or through the inclusion of an adjuvant during immunization.

Booster injections can be given at regular intervals, with at least one usually being required for optimal antibody production. The antiserum may be harvested when the antibody titer begins to fall. Titer may be determined semi-quantitatively, for example, by double immunodiffusion in agar against known concentrations of the antigen. See, for example, Ouchterlony et al., Chap. 19 in: *Handbook of Experimental Immunology*, Wier, ed, Blackwell (1973). Plateau concentration of antibody is usually in the range of 0.1 to 0.2 mg/ml of serum (about 12 $\mu$M). The antiserum may be purified by affinity chromatography using the immobilized immunogen carried on a solid support. Such methods of affinity chromatography are well known in the art.

Affinity of the antisera for the antigen may be determined by preparing competitive binding curves, as described, for example, by Fisher, Chap. 42 in: *Manual of Clinical Immunology*, second edition, Rose and Friedman, eds., Amer. Soc. For Microbiology, Washington, D.C. (1980).

ii) Monoclonal Antibodies.

Monoclonal antibodies (MAbs), are homogeneous populations of antibodies to a particular antigen. They may be obtained by any technique that provides for the production of antibody molecules by continuous cell lines in culture or in vivo. MAbs may be produced by making hybridomas, which are immortalized cells capable of secreting a specific monoclonal antibody.

Monoclonal antibodies to any of the proteins, peptides and epitopes thereof described herein can be prepared from murine hybridomas according to the classical method of Kohler, G. and Milstein, C., *Nature* 256:495–497 (1975) (and U.S. Pat. No. 4,376,110) or modifications of the methods thereof, such as the human B-cell hybridoma technique (Kosbor et al., 1983, *Immunology Today* 4:72; Cole et al., 1983, *Proc. Natl. Acad. Sci.* USA 80: 2026–2030), and the EBV-hybridoma technique (Cole et al., 1985, MONOCLONAL ANTIBODIES AND CANCER THERAPY, Alan R. Liss, Inc., pp. 77–96).

In one method a mouse is repetitively inoculated with a few micrograms of the selected protein over a period of a few weeks. The mouse is then sacrificed, and the antibody producing cells of the spleen are isolated. The spleen cells are fused, typically using polyethylene glycol, with mouse myeloma cells, such as SP2/0-Ag14 myeloma cells. The excess, unfused cells are destroyed by growth of the system on selective media comprising aminopterin (HAT media). The successfully fused cells are diluted, and aliquots are plated to microliter plates where growth is continued. Antibody-producing clones (hybridomas) are identified by detection of antibody in the supernatant fluid of the wells by immunoassay procedures. These include ELISA, as originally described by Engvall, *Meth. Enzymol.* 70:419 (1980), western blot analysis, radioimmunoassay (Lutz et al., *Exp. Cell Res.* 175:109–124 (1988)) and modified methods thereof.

Selected positive clones can be expanded and their monoclonal antibody product harvested for use. Detailed procedures for monoclonal antibody production are described in Davis, L. et al. BASIC METHODS IN MOLECULAR BIOLOGY, Elsevier, N.Y. Section 21–2 (1989). The hybridoma clones may be cultivated in vitro or in vivo, for instance as ascites. Production of high titers of mAbs in vivo makes this the presently preferred method of production. Alternatively, hybridoma culture in hollow fiber bioreactors provides a continuous high yield source of monoclonal antibodies.

The antibody class and subclass may be determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). MAbs may be of any immunoglobulin class including IgG, IgM, IgE, IgA, IgD and any subclass thereof. Methods of purifying monoclonal antibodies are well known in the art.

iii) Antibody Derivatives and Fragments.

Fragments or derivatives of antibodies include any portion of the antibody which is capable of binding the target antigen, or a specific portion thereof. Antibody fragments specifically include F(ab')$_2$, Fab, Fab' and Fv fragments. These can be generated from any class of antibody, but typically are made from IgG or IgM. They may be made by conventional recombinant DNA techniques or, using the classical method, by proteolytic digestion with papain or pepsin. See CURRENT PROTOCOLS IN IMMUNOLOGY, chapter 2, Coligan et al., eds., (John Wiley & Sons 1991–92).

F(ab')$_2$ fragments are typically about 110 kDa (IgG) or about 150 kDa (IgM) and contain two antigen-binding regions, joined at the hinge by disulfide bond(s). Virtually all, if not all, of the Fc is absent in these fragments. Fab' fragments are typically about 55 kDa (IgG) or about 75 kDa (IgM) and can be formed, for example, by reducing the disulfide bond(s) of an F(ab')$_2$ fragment. The resulting free sulfhydryl group(s) may be used to conveniently conjugate Fab' fragments to other molecules, such as detection reagents (e.g., enzymes).

Fab fragments are monovalent and usually are about 50 kDa (from any source). Fab fragments include the light (L) and heavy (H) chain, variable ($V_L$ and $V_H$, respectively) and constant ($C_L$ and $C_H$, respectively) regions of the antigen-binding portion of the antibody. The H and L portions are linked by an intramolecular disulfide bridge.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interacts and, thus, they readily dissociate; however, they have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers.

Other antibody derivatives include single chain antibodies (U.S. Pat. No. 4,946,778; Bird, Science 242:423–426 (1988); Huston et al., Proc. Natl. Acad. Sci. USA 85:5879–5883 (1988); and Ward et al., Nature 334:544–546 (1989)). Single chain antibodies are formed by linking the heavy and light chain fragments of the Fv region via an amino acid bridge, resulting in a single chain Fv (SCFv).

One preferred method involves the generation of scFvs by recombinant methods, which allows the generation of Fvs with new specificities by mixing and matching variable chains from different antibody sources. In a typical method, a recombinant vector would be provided which comprises the appropriate regulatory elements driving expression of a cassette region. The cassette region would contain a DNA encoding a peptide linker, with convenient sites at both the 5' and 3' ends of the linker for generating fusion proteins. The DNA encoding a variable region(s) of interest may be cloned in the vector to form fusion proteins with the linker, thus generating a scFv.

In an exemplary alternative approach, DNAs encoding two Fvs may be ligated to the DNA encoding the linker, and the resulting tripartite fusion may be ligated directly into a conventional expression vector. The scFv DNAs generated any of these methods may be expressed in prokaryotic or eukaryotic cells, depending on the vector chosen.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab)$_2$ fragments. Alternatively, Fab expression libraries may be constructed (Huse et al., 1989, *Science*, 246:1275–1281) to allow rapid and easy identification of monoclonal Fab fragments with the desired specificity.

Derivatives also include "chimeric antibodies" (Morrison et al., *Proc. Natl. Acad. Sci.*, 81:6851–6855 (1984); Neuberger et al., *Nature*, 312:604–608 (1984); Takeda et al., *Nature*, 314:452–454 (1985)). These chimeras are made by splicing the DNA encoding a mouse antibody molecule of appropriate specificity with, for instance, DNA encoding a human antibody molecule of appropriate specificity. Thus, a chimeric antibody is a molecule in which different portions are derived from different animal species, such as those having a variable region derived from a murine mAb and a human immunoglobulin constant region. These are also known sometimes as "humanized" antibodies and they offer the added advantage of at least partial shielding from the human immune system. They are, therefore, particularly useful in therapeutic in vivo applications.

iv) Labeled Antibodies.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well-known in the art, for example see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ diagnostic assays.

v) Immobilized Antibodies.

The foregoing antibodies also may be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as for immunoaffinity purification of the proteins of the present invention.

Pharmaceutical Compositions Comprising a POT1 Gene.

Pharmaceutical compositions comprising polynucleotides encoding functional Pot1 polypeptides of the invention are those useful for gene therapy to cause the overexpression of functional Pot1 polypeptides in cells in which chromosome stabilization is desired, or the overexpression of a variant Pot1 polypeptide with dominant negative interference activity in cells in which chromosome destabilization is desired.

Overexpression of POT1 in a cell may be accomplished by transfecting a cell with a POT1 polynucleotide. The POT1 polynucleotide generally is a component on an expression vector of the invention, defined above. The vector may be delivered to a cell by transfection of a cell ex vivo, followed by selection and cloning of transfected cells expressing the POT1 nucleotide and then by administration of the stably transfected cells to an individual in need of the modified cells.

Alternatively, the POT1 polynucleotide may be delivered to a cell or a population of cells in an individual. Various methods of introducing exogenous genes into cells in vivo are known in the art. See Rosenberg et al., *Science* 242:1575–1578 (1988) and Wolff et al., *PNAS* 86:9011–9014 (1989), which are incorporated herein by reference. A listing of suitable vectors is set forth in Hodgson, *Bio/Technology* 13: 222 (1995), which is incorporated by reference. One example of a suitable vector is a cationic liposome, such as DC-Chol/DOPE liposome, which is an appropriate vehicle to deliver DNA to a wide range of tissues through intravenous injection of DNA/cationic liposome complexes. See Caplen et al., *Nature Med.* 1:39–46 (1995) and Zhu et al., *Science* 261:209–211 (1993), herein incorporated by reference.

Viral vector-mediated gene transfer is also a suitable method for the introduction of the vector into a target cell. Appropriate viral vectors include adenovirus vectors and adeno-associated virus vectors, retrovirus vectors and herpesvirus vectors. Adenoviruses are linear, double stranded DNA viruses complexed with core proteins and surrounded by capsid proteins. The common serotypes 2 and 5, which are not associated with any human malignancies, are typically the base vectors. By deleting parts of the virus genome and inserting the desired gene under the control of a constitutive viral promoter, the virus becomes a replication-deficient vector capable of transferring the exogenous DNA to differentiated, non-proliferating cells. To enter cells, the adenovirus interacts with specific receptors on the cell surface, and the adenovirus surface proteins interact with the cell surface integrins. The virus penton-cell integrin interaction provides the signal that brings the exogenous gene-containing virus into a cytoplasmic endosome. The adenovirus breaks out of the endosome and moves to the nucleus, the viral capsid falls apart, and the exogenous DNA enters the cell nucleus where it functions, in an epichromosomal fashion, to express the exogenous gene. Detailed discussions of the use of adenoviral vectors for gene therapy can be found in Berkner, *Biotechniques* 6:616–629 (1988) and Trapnell, *Advanced Drug Delivery Rev.* 12:185–199 (1993), which are herein incorporated by reference. Adenovirus-derived vectors, particularly non-replicative adenovirus vectors, are characterized by their ability to accommodate exogenous DNA of 7.5 kB, relative stability, wide host range, low pathogenicity in man, and high titers ($10^4$ to $10^5$ plaque forming units per cell). See Stratford-Perricaudet et al., *PNAS* 89:2581 (1992).

Pharmaceutical compositions may be formulated with one or more physiologically acceptable carriers or excipients. In one embodiment, the composition is formulated for injection. Long acting formulations are generally known in the art and can be adapted to the administration of a POT1 polynucleotide. Such compositions may be in the form of suspensions, solutions, emulsions in vesicles, or any other form known in the art. Additional suspending, stabilizing, or dispersing agents may be added as necessary. Alternatively, the active ingredient may be in the form of a powder for reconstitution prior to administration.

Diagnostic Methods.

The present invention also contemplates methods for diagnosis of human disease. In particular, patients can be screened for the occurrence of cancers, or likelihood of occurrence of cancers, associated with mutations in the Pot1 protein or with changes in its level of expression. By examining a number of patients in this manner, mutations in the gene that are associated with a malignant cellular phenotype can be identified. In addition, correlation of the nature of the observed mutations with subsequent observed clinical outcomes allows development of prognostic model for the predicted outcome in a particular patient.

Screening for mutations conveniently can be carried out at the DNA level by use of PCR, although the skilled artisan will be aware that many other well known methods are available for the screening. PCR primers can be selected that flank known mutation sites, and the PCR products can be sequenced to detect the occurrence of the mutation. Alternatively, the 3' residue of one PCR primer can be selected to be a match only for the residue found in the unmutated gene. If the gene is mutated, there will be a mismatch at the 3' end of the primer, and primer extension cannot occur, and no PCR product will be obtained. Alternatively, primer mixtures can be used where the 3' residue of one primer is any nucleotide other than the nonmutated residue. Observation of a PCR product then indicates that a mutation has occurred. Other methods of using, for example, oligonucleotide probes to screen for mutations are described, or example, in U.S. Pat. No. 4,871,838, which is herein incorporated by reference in its entirety.

Alternatively, antibodies can be generated that selectively bind either mutated or non-mutated Pot1 protein. The antibodies then can be used to screen tissue samples for occurrence of mutations in a manner analogous to the DNA-based methods described above.

The diagnostic methods described above can be used not only for diagnosis and for prognosis of existing disease, but may also be used to predict the likelihood of the future occurrence of disease. For example, clinically healthy patients can be screened for mutations in the Pot1 protein that correlate with later disease onset. Such mutations may be observed in the heterozygous state in healthy individuals. In such cases a single mutation event can effectively disable proper functioning of the gene encoding the Pot1 protein and induce a transformed or malignant phenotype. This screening also may be carried out prenatally or neonatally.

DNA molecules according to the invention also are well suited for use in so-called "gene chip" diagnostic applications. Such applications have been developed by, inter alia, Synteni and Affymetrix. Briefly, all or part of the DNA molecules of the invention can be used either as a probe to screen a polynucleotide array on a "gene chip," or they may be immobilized on the chip itself and used to identify other polynucleotides via hybridization to the surface of the chip. In this manner, for example, related genes can be identified, or expression patterns of the POT1 gene in various tissues can be simultaneously studied. Such gene chips have particular application for diagnosis of disease, or predisposition to disease, which may be indicated by a change in the level or tissue distribution of POT1 mRNA or by the presence of a particular POT1 mRNA species. Suitable chip technology is described for example, in Wodicka et al., *Nature Biotechnology,* 15:1359 (1997) which is hereby incorporated by reference.

Detection of a Pot1 Polypeptide.

The presence of a Pot1 protein may be assayed in a biological sample isolated from an individual. Pot1p may be detected in any number of ways commonly known in the art. For example, Pot1p may be detected by a specific interaction with a labeled antibody of the invention. The antibody label allows rapid detection of an immune complex by such well known methods as Western blotting. Formation of an immune complex will be useful in detecting Pot1 proteins with or without biological function. Thus, an immune complex formation will be the preferred mode of detection of a Pot1 protein in a sample from an individual, where the Pot1 protein in the sample is suspected of lacking activity through genetic alteration. Such an assay thus will be useful in a diagnostic method, to detect altered forms of Pot1p.

Alternatively, a Pot1 protein may be assayed by virtue of its biological function. In one embodiment, a sample suspected of containing a Pot1 polypeptide is exposed to isolated labeled telomeric DNA. A Pot1 protein is then detected by its ability to interact with the telomeric DNA. A convenient method of assaying this interaction is with a gel shift assay, which is well known in the art and used to form the Pot1p-DNA complexes in Example 2.

Pharmaceutical Compositions Comprising Compounds that Affect Pot1p Activity, and Routes of Administering the Same.

Pharmaceutical compositions comprising compounds that affect Pot1 protein activity can be formulated and administered according to well known methods. These compounds include those small molecule compounds that affect Pot1p binding to telomeric DNA identified by the screening methods of the invention. These compounds may be delivered in a pharmaceutically acceptable carrier vehicle. Suitable vehicles and their formulation are described, for example, in *Remington's Pharmaceutical Sciences* (16th ed., Osol, A., Ed., Mack, Easton Pa. (1980)).

Pharmaceutical compositions are formulated to provide a "therapeutically effective amount" of a compound that affects the activity of a Pot1 protein. The amount of a compound required for therapeutic efficacy depends on the individual or animal to be treated, and on the precise condition involving a Pot1 protein. The amount actually administered will be optimized to reduce side-effects while having a maximum effect on the activity of a Pot1 protein. Preferably, the amount delivered to the body will be reduced by directed delivery to a population of target cells, where possible.

Pharmaceutical compositions for use in accordance with the present invention may be formulated in conventional manner using one or more physiologically acceptable carriers or excipients. Thus, the compounds and their physiologically acceptable salts may be formulated for administration by a variety of routes. The compounds may be delivered by parenteral, inhalation or insufflation (either through the mouth or the nose), topical, oral, or depot administration.

The compounds may be formulated for parenteral administration by injection, e.g., by bolus injection, repeated injections, or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain agents that aid in suspending, stabilizing or dispersing the active compounds. Alternatively, the active ingredient may be in powder form for constitution with a suitable vehicle, e.g., sterile pyrogen-free water, before use. Instead of injection, the compounds may be administered as an irrigation fluid used to wash areas or organs of the body.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoro-ethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

In addition to the formulations described previously, the compounds may also be formulated as a depot preparation. Such long acting formulations may be administered by implantation (for example subcutaneously or intramuscularly) or by intramuscular injection. The compounds may also be formulated in rectal compositions such as suppositories or retention enemas, e.g., containing conventional suppository bases such as cocoa butter or other glycerides.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated or formulated for sustained release by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preferred formulations for oral delivery are described by U.S. Pat. Nos. 5,574,018 and 5,428,023. Biologically active conjugates of a therapeutically useful protein are made with vitamin $B_{12}$ ($VB_{12}$) by covalently binding the primary (5') hydroxyl group of the ribose moiety of $VB_{12}$ to the therapeutic protein. When the resulting conjugate is orally delivered, it binds intrinsic factor (IF) transporter protein in the gastrointestinal tract and is then taken up through the epithelium into the bloodstream, retaining the biological activity of the protein therapeutic. The conjugates may be orally administered in the presence of purified IF, resulting in greater absorption.

WO 93/25221 describes compositions formulated for oral delivery, comprising therapeutic proteins contained in microspheres made of protein and/or synthetic polymer. The microspheres protect their protein contents against gastrointestinal proteases and provide controlled and sustained release of their contents. Microspheres can be designed to pass through the intestinal epithelium into the blood or lymph, and they may be targeted to particular cells or organs. Formulations and methodology useful for targeting orally administered microparticles to various organs are described in EP 531,497, for example.

The present invention, thus generally described, will be understood more readily by reference to the following examples, which are provided by way of illustration and are not intended to be limiting of the present invention.

EXAMPLES

Example 1

Expression and Purification of SpPot1p

SpPot1p containing N-terminal V5 and $His_6$-tags was cloned into the pQE30 expression vector (Qiagen), which introduces an additional N-terminal $His_6$-tag, and expressed in *E. coli* strain M15 (pRep4) using tryptone phosphate media. Following induction (0.8 mM IPTG) for 6 hours at 24° C. cells were harvested, resuspended in lysis buffer at pH 8.0 (50 mM $NaH_2PO_4$; 0.1 M NaCl; 2 mM imidazole; 10% glycerol; 0.2% Tween20; 5 mM β-mercaptoethanol, 1 mM PMSF) and lysed by the addition of lysozyme (0.5 mg/ml). After 30 min the concentration of NaCl was increased to 0.6 M, genomic DNA was sheared by sonication and cell debris was removed by centrifugation at 10,000 g for 30 min. The supernatant was incubated with Ni-NTA resin (Qiagen) at 4° C. for 90 min, which was then loaded onto a column and washed sequentially with P buffer (50 mM $NaH_2PO_4$; 600 mM NaCl; 10% glycerol; 0.2% Tween20; 5 mM β-mercaptoethanol) containing increasing concentrations of imidazole. Pot1p eluted around 90 mM imidazole. Pot1 containing fractions were dialysed against T buffer (50 mM Tris/HCl pH 8.0; 10% glycerol; 0.5 mM EDTA; 0.5 mM DTT) containing 0.2 M KCl and Pot1p was further purified on a Q-sepharose column (Pharmacia) using a linear gradient of KCl (0.2 M-1 M). Pot1p eluted around 0.5M KCl, was dialysed against T buffer plus 0.2 M KCl and stored in aliquots at −80° C.

Example 2

DNA-Binding Specificity of SpPot1p

C-strand (CGTAACCGTAACCCTGTAACCT- GTAACCT GTAACCGTGTAACC) (SEQ ID NO: 40) and G-strand (GGTTACACGGTTACAGGTTACAGG- TTACAGGGTTACGGTTACG) (SEQ ID NO: 28) were 5' $^{32}$P-labeled using T4 polynucleotide kinase and γ-$^{32}$P-ATP. Duplex DNA was generated by annealing equimolar amounts of radiolabeled C-strand and unlabelled G-strand. Binding reactions (10 μl) were carried out in 25 mM HEPES (pH 7.5), 1 mM EDTA, 50 mM NaCl, 5% glycerol, and 2.5 μM PBoli109 (CCGTAAGCATTTCATTATTGGA- ATTCGAGCTCGTTTTCGA) (SEQ ID NO: 41) as non-specific competitor. Pot1p (50 ng) was incubated with the indicated DNA substrates (1 ng) for 15 mm at 20° C. Complexes were analyzed by electrophoresis at 4° C. through a 4–20% TBE gel (Invitrogen) run at 150 V for 80 min. The Pot1p-DNA complex is indicated by an open arrow in FIG. 3A. FIG. 3B shows the same experiment except that the added protein (100 ng) contained truncated Pot1p as well as full length protein. Truncated Pot1p-DNA complex is indicated by a closed arrow.

Example 3

Substrate Specificity of SpPot1p and hPot1p

FIG. 6A shows binding of SpPot1p to radiolabeled *S. pombe* and human G-strand DNAs. FIG. 6B shows binding of SpPot1p (50 ng) to radiolabeled G-strand (15 pg or 1.5 fmol) in the presence of 10-, 100-, and 1000-fold excess of unlabeled *S. pombe*, human or *O. nova* G-strand. FIG. 6C shows binding of hPot1p to radiolabeled *S. pombe* and human G-strand DNAs. FIG. 6D shows binding of hPot1p to radiolabeled human G-strand DNA under same conditions as in FIG. 6B.

Example 4

Cloning of the hPOT1 Gene

Oligos PBoli164T (SEQ ID NO: 42) (TTCAGATGTTATCTGTCAATCAGAACCTG) and PBoli194B (SEQ ID NO: 43) (GAACACTGTTTA- CATCCATAGTGATGTATTGTTCC) were used to amplify a 614 bp fragment of hPOT1 from multiple tissue cDNA panels (Clontech) with Advantage 2 Polymerase mix in the buffer supplied by Clontech. Cycling parameters of touchdown PCR were 94° C. for 5 s, 68° C. for 120 s (32 cycles). The gene encoding glyceraldehyde phosphate dehydrogenase (GAPDH) was used as a positive control for the integrity of the cDNA sample and was amplified for 26 cycles with primers (SEQ ID NO: 44) TGAAGGTCG- GAGTCAACGGATTTGGT and (SEQ ID NO: 45) CAT- GTGGGCCATGAGGTCCACCAC.

hPOT1 was PCR amplified from ovary cDNA and cloned into a pQE30 expression vector. Recombinantly expressed hPot1p (carrying an N-terminal $His_6$-tag) was purified from *E. coli*. The protein was purified over Ni-NTA resin under the same conditions as SpPot1p. The human protein eluted at around 135 mM imidazole.

The description, specific examples, and data, while indicating exemplary embodiments, are given by way of illustration and are not intended to limit the present invention. Various changes and modifications within the present invention will become apparent to the skilled artisan from the disclosure, and thus are considered part of the invention.

What is claimed is:

1. An isolated hPot 1 polypeptide having the amino acid sequence set forth in SEQ ID NO: 15.

2. The polypeptide according to claim 1, wherein said polypeptide is encoded by the polynucleotide set forth in SEQ ID NO: 14.

3. An isolated hPot 1 polypeptide having the amino acid sequence set forth in SEQ ID NO: 17.

4. The polypeptide according to claim 3, wherein said polypeptide is encoded by the polynucleotide act forth in SEQ ID NO: 16.

* * * * *

SEQUENCE LISTING

<160> NUMBER OF SEQ ID NOS: 45

<210> SEQ ID NO 1
<211> LENGTH: 118
<212> TYPE: PRT
<213> ORGANISM: Euplotes crassus

<400> SEQUENCE: 1

```
Gln Lys Ala Ala Lys Lys Asp His Tyr Gln Tyr Ser Asp Leu Ser Ser
 1               5                  10                  15

Ile Lys Lys Glu Gly Glu Glu Asp Gln Tyr His Phe Tyr Gly Val Val
            20                  25                  30

Ile Asp Ala Ser Phe Pro Tyr Lys Gly Glu Lys Arg Tyr Val Val Thr
        35                  40                  45

Cys Lys Val Ala Asp Pro Ser Ser Val Ala Lys Gly Gly Lys Leu Asn
    50                  55                  60

Thr Val Asn Val Val Phe Phe Ser Gln Asn Phe Glu Asp Leu Pro Ile
65                  70                  75                  80

Ile Gln Arg Val Gly Asp Ile Val Arg Val His Arg Ala Arg Leu Gln
                85                  90                  95

His Tyr Asn Asp Ala Lys Gln Leu Asn Val Asn Met Tyr Tyr Arg Ser
            100                 105                 110

Ser Trp Cys Leu Phe Ile
            115
```

<210> SEQ ID NO 2
<211> LENGTH: 123
<212> TYPE: PRT
<213> ORGANISM: Stylonychia mytilis

<400> SEQUENCE: 2

```
Lys Lys Arg Glu Gln Ser Thr Arg Tyr Lys Tyr Val Glu Leu Asn Lys
 1               5                  10                  15

Ala Ser Leu Thr Ser Ala Glu Ala Gln His Phe Tyr Gly Val Val Ile
            20                  25                  30

Asp Ala Thr Phe Pro Tyr Lys Thr Asn Gln Glu Arg Tyr Ile Cys Ser
        35                  40                  45

Leu Lys Val Val Asp Pro Ser Leu Tyr Leu Lys Ser Gln Lys Gly Thr
    50                  55                  60

Gly Asp Ala Ser Asp Tyr Ala Thr Leu Val Leu Tyr Ala Lys Arg Phe
65                  70                  75                  80

Glu Asp Leu Pro Ile Ile His Arg Ile Gly Asp Ile Ile Arg Val His
                85                  90                  95

Arg Ala Thr Leu Arg Leu Tyr Asn Gly Gln Arg Gln Phe Asn Ala Asn
            100                 105                 110

Val Phe Tyr Asn Ser Ser Trp Ala Leu Phe Ser
            115                 120
```

<210> SEQ ID NO 3
<211> LENGTH: 123
<212> TYPE: PRT
<213> ORGANISM: Oxytricha trifallax

<400> SEQUENCE: 3

```
Lys Lys Ala Glu Lys Gly Ser Lys Tyr Glu Tyr Val Glu Leu Thr Lys
 1               5                  10                  15
```

```
Ala Gln Leu Thr Ser Val Thr Ala Gln His Phe Tyr Ala Val Val Ile
            20                  25                  30

Asp Ala Thr Phe Pro Tyr Lys Thr Asn Gln Glu Arg Tyr Ile Cys Ser
        35                  40                  45

Leu Lys Ile Val Asp Pro Ser Leu Tyr Leu Lys Glu Lys Gly Thr
    50                  55                  60

Gly Asp Asn Ser Asp Tyr Ala Thr Leu Val Leu Tyr Ala Lys Arg Phe
 65              70                  75                  80

Glu Asp Leu Pro Ile Ile His Arg Leu Gly Asp Ile Ile Arg Ile His
                85                  90                  95

Arg Ala Thr Ile Arg Leu Tyr Asn Gly Gln Arg Gln Phe Asn Ala Asn
            100                 105                 110

Ile Phe Tyr Ser Ser Ser Trp Ala Leu Phe Ser
            115                 120

<210> SEQ ID NO 4
<211> LENGTH: 123
<212> TYPE: PRT
<213> ORGANISM: Oxytricha nova

<400> SEQUENCE: 4

Lys Lys Ser Asp Lys Gly His Lys Tyr Glu Tyr Val Glu Leu Ala Lys
 1               5                  10                  15

Ala Ser Leu Thr Ser Ala Gln Pro Gln His Phe Tyr Ala Val Val Ile
            20                  25                  30

Asp Ala Thr Phe Pro Tyr Lys Thr Asn Gln Glu Arg Tyr Ile Cys Ser
        35                  40                  45

Leu Lys Ile Val Asp Pro Thr Leu Tyr Leu Lys Gln Gln Lys Gly Ala
    50                  55                  60

Gly Asp Ala Ser Asp Tyr Ala Thr Leu Val Leu Tyr Ala Lys Arg Phe
 65              70                  75                  80

Glu Asp Leu Pro Ile Ile His Arg Ala Gly Asp Ile Ile Arg Val His
                85                  90                  95

Arg Ala Thr Leu Arg Leu Tyr Asn Gly Gln Arg Gln Phe Asn Ala Asn
            100                 105                 110

Val Phe Tyr Ser Ser Ser Trp Ala Leu Phe Ser
            115                 120

<210> SEQ ID NO 5
<211> LENGTH: 109
<212> TYPE: PRT
<213> ORGANISM: Homo sapiens

<400> SEQUENCE: 5

Met Ser Leu Val Pro Ala Thr Asn Tyr Ile Tyr Thr Pro Leu Asn Gln
 1               5                  10                  15

Leu Lys Gly Gly Thr Ile Val Asn Val Tyr Gly Val Val Lys Phe Phe
            20                  25                  30

Lys Pro Pro Tyr Leu Ser Lys Gly Thr Asp Tyr Cys Ser Val Val Thr
        35                  40                  45

Ile Val Asp Gln Thr Asn Val Lys Leu Thr Cys Leu Leu Phe Ser Gly
    50                  55                  60

Asn Tyr Glu Ala Leu Pro Ile Ile Tyr Lys Asn Gly Asp Ile Val Arg
 65              70                  75                  80

Phe His Arg Leu Lys Ile Gln Val Tyr Lys Lys Glu Thr Gln Gly Ile
                85                  90                  95
```

Thr Ser Ser Gly Phe Ala Ser Leu Thr Phe Glu Gly Thr
          100                 105

<210> SEQ ID NO 6
<211> LENGTH: 116
<212> TYPE: PRT
<213> ORGANISM: Schizosaccharomyces pombe

<400> SEQUENCE: 6

Lys Ile Gly Glu Leu Thr Phe Gln Ser Ile Arg Ser Ser Gln Glu Leu
 1               5                  10                  15

Gln Lys Lys Asn Thr Ile Val Asn Leu Phe Gly Ile Val Lys Asp Phe
             20                  25                  30

Thr Pro Ser Arg Gln Ser Leu His Gly Thr Lys Asp Trp Val Thr Thr
         35                  40                  45

Val Tyr Leu Trp Asp Pro Thr Cys Asp Thr Ser Ser Ile Gly Leu Gln
     50                  55                  60

Ile His Leu Phe Ser Lys Gln Gly Asn Asp Leu Pro Val Ile Lys Gln
 65                  70                  75                  80

Val Gly Gln Pro Leu Leu Leu His Gln Ile Thr Leu Arg Ser Tyr Arg
                 85                  90                  95

Asp Arg Thr Gln Gly Leu Ser Lys Asp Gln Phe Arg Tyr Ala Leu Trp
            100                 105                 110

Pro Asp Phe Ser
        115

<210> SEQ ID NO 7
<211> LENGTH: 3980
<212> TYPE: DNA
<213> ORGANISM: Schizosaccharomyces pombe

<400> SEQUENCE: 7
tatgagtgaa gttccatcca tgatgcaaaa agccatgctg tcaaccttaa aaagtatatc      60
ggccattccc gatgatgtac cccctcctta ttctgagttt gctgatgata cgacagcgca     120
agctggttct agtaaaagag atagcgctat atctgaagat cccgatcatc acaaaagtgt     180
ttggtggtct ttgagatggc aatctcggct tgttggtcgt ggaaaatcta ctgctcttac     240
tcctgaagaa accagagcaa tacaggagca ggcaaagaca ctgaaaaagg caggaatgga     300
ctttatgcta ttctctttct ggttacctgc cctacttttg ctgagtatct tggtcttcg      360 aagctatgct caaatgatcg ggggatattt atatcgctgc ataattggca tttaggtttg     420
acgaacaacc atgcatgttt ttttcttttct tttagtttta ttcttttttg tagattatga    480
gcaaactact gtcaaaactt aggtattatg acaatgaaat cgtatatatt atattcgatt     540
ggatcaattt tttattatat tgaaagtaat tgcttatttt gtaagttaaa cttacatggg     600
tttaaacgca tagagcaggt tggcgctttt aaaccaaaa tagatcgttg caggtttgct      660
gttctggatc gtgaatgcaa taccttagga aagtctttta ataagctatc gcttttgca     720 ttgcattctt tttctaaact gaacgttaga ttagctaaag taagcgtctt gagttttcga     780
gatgaaccgc atacattaaa atttttaagt accaattggc atgaaccggt atgcgatctg     840
cttattataa tactagtaaa tcttgatact cggcaaactc tttcaataat agcctagcag     900
aaactgggat atgtctaaag ttttacaact gcgctcagct taaggacttt acggcgatcc     960
atttaatagc tagccatgaa cactcataac ctcaagattg aggagtgggt cattcttttg    1020
cttgataaag aaacaaattc attattggta aaataaaact gaataaccct tagttcatcc    1080

```
taggaatttg aagaagggga atgatcaagc ttgaacaagt aactctcacg cagtctattg   1140
aataatctga aggttcatca ctttcaaggg gttgtcttgg tttaaaaagc ttttaccaat   1200
tccatttagg tttctgagaa aggctaaaac tcatttgttg ttcttaaagg atatttggat   1260
cattcgttga tcaagcatgg gagaggacgt tattgacagt cttcagttga atgagttatt   1320
aaatgctgga gaatataaga ttggagtgag atatcaatgg atttatattt gttttgctaa   1380
caatgaaaaa ggaacttaca tttcagtcca ttagaagctc tcaagaatta caaagaaga   1440 atactattgt caatttgttt ggaatagtaa aagattttac ccctagtcgc caaagtctac   1500
atggaactaa gggtatgctt gcttatcatg gtggaaacta acttttttat ttttccagtc   1560
aagagctaat aatcatgttt ttagattggg taaccaccgt atatttgtgg gatccaacat   1620
gtgatacatc aagcatcgga ctacagatac acttgttcag caaacaggga atgatttgc    1680 ctgtaatcaa gcaggtgggg caaccgcttt tgcttcatca aatcacatta agaagttata   1740
gagacaggac tcaaggtttg tctaaggatc aatttcgata tgcactttgg ccagactttt   1800
cttctaattc caaagatact ctctgtcctc aaccaatgcc tcgtttaatg aaaacgggag   1860
acaaggaaga gcaattcgcc ttgttgttaa ataaaatttg ggatgagcaa actaataaac   1920
ataaaaatgg cgaattattg agtacctctt ctgctcgtca aaatcaaact ggattgagtt   1980
acccttctgt ctcttttct  ctgctatcac aaataactcc acatcaacgt tgtagctttt   2040
acgctcaggt aattaaaact tggtacagtg ataaaaactt tactctttat gtcactgatt   2100
atacggaaaa tgagcttttt tttccaatgt ctccgtatac tagctcctcg agatggaggg   2160
gcccttttgg tcggttttct ataaggtgca ttttatggga tgagcacgac ttttactgcc   2220
gcaactacat taagaaggt  gactatgtgg ttatgaaaaa tgtgcgaacc aaaattgatc   2280
accttggtta tctggaatgt atacttcatg gggattcagc aaaacgttat aatatgagta   2340
tagaaaaagt cgattcggaa gaacccgaac taaacgaaat taagtcacgt aaaaggcttt   2400
atgttcagaa ttgccaaaat ggtatagaag cagtaatcga gaaactcagt caaagccaac   2460
aatcggaaaa tccttttatc gcccatgaat taaagcaaac ttctgttaat gaaattacgg   2520
cccatgtcat aaatgaacct gctagtttaa aattgactac tatttctacc atacttcatg   2580 caccttgca  gaatcttctc aaaccgagga acataggct  acgcgttcag gtggtagatt   2640
tttggccaaa gagtttgacg cagtttgctg tgctatctca accaccatct tcgtatgttt   2700
ggatgtttgc cttgctcgta agggatgtat cgaatgtgac tttaccggtc atattttttg   2760
attctgacgc tgcggaactt attaacagct caaaaatcca accttgcaat ttagctgatc   2820
acccgcagat gactcttcag cttaaagaaa gattatttct gatttggggg aacttggaag   2880
aacgcattca gcatcacata tcgaagggtg aatcgccaac tctggctgct gaagatgttg   2940
aaacaccatg gtttgatata tatgtcaaag aatacattcc tgtaattggg aacaccaaag   3000
accatcaatc tttgactttt cttcagaagc gctggcgagg atttggcacg aaaattgttt   3060
gactattgtg atacaaaact tacaataatg aaatgcttac ggaaaagaaa cataagaaaa   3120
acaatattta aatttaagga aagctctata ttgggagaat tttataaagc gagcgaattt   3180
gtactaagga aaaacacaga ggggaaacgt gaaatatcta attgcttaga ctttatataa   3240
catcaacttc gaaataatct tagaaattaa ttacaaaaat aataaggatt ggtttgatgt   3300
atggtggtta catctaagca ggcttttgct tagaagttgc aagtgttgag gcatcatcat   3360
cactttcatc gtcaacagcg aatagagctt gatgctcatc ggcactgcca tgaataatat   3420
gagggttggc tggagatgta ggacgctcat gatgcagatg caaactatca tttgagagag   3480
```

-continued

```
aggaagtcat ctcaaactca tctacatctt gagcaacttg ctcactcatt gcgaaacgac    3540
ggttattctc ggtaggacgc cacaagtaca aaatggtaag catcaagatc aaaacaagaa    3600
tatcagtgta tccgtaatta aggaaccaaa gaagtttcca gtattttaag taatagttca    3660
tttgaccgta gataccaatc aaaatggcat tggctgcgac aatcgaagca taagcgacaa    3720
tgccaaaaca tataacaatc aaagacgag tatacatctg agccttaaca gtttgcttac    3780
gaatacggag atcacgaatt gtattattta aagccaatac aatccaaagg aacatagcga    3840
agagggtgat taaaaagaca ggagcggcaa acaaaatgac caaagactct ttattagatg    3900
ggctaatgaa caaagatgac aagaaaaagc atgaagaaac gaactgcaaa ccagcaagaa    3960
tttgacactt acgaagaaga                                                3980
```

<210> SEQ ID NO 8
<211> LENGTH: 2087
<212> TYPE: DNA
<213> ORGANISM: Schizosaccharomyces pombe

<400> SEQUENCE: 8

```
gattgaggag tgggtcattc ttttgcttga taaagaaaca aattcattat tggtaaaata      60
aaactgaata acccttagtt catcctagga atttgaagaa ggggaatgat caagcttgaa     120
caagtaactc tcacgcagtc tattgaataa tctgaaggtt catcactttc aagggggttgt    180 cttggtttaa aaagctttta ccaattccat ttaggtttct gagaaaggct aaaactcatt     240
tgttgttctt aaaggatatt tggatcattc gttgatcaag catgggagag gacgttattg     300
acagtcttca gttgaatgag ttattaaatg ctggagaata taagattgga gaacttacat     360
ttcagtccat tagaagctct caagaattac aaaagaagaa tactattgtc aatttgtttg     420
gaatagtaaa agattttacc cctagtcgcc aaagtctaca tggaactaag gattgggtaa     480
ccaccgtata tttgtgggat ccaacatgtg atacatcaag catcggacta cagatacact     540
tgttcagcaa acagggaaat gatttgcctg taatcaagca ggtggggcaa ccgcttttgc     600
ttcatcaaat cacattaaga agttatagag acaggactca aggtttgtct aaggatcaat     660
ttcgatatgc actttggcca gactttcctt ctaattccaa agatactctc tgtcctcaac     720
caatgcctcg tttaatgaaa acgggagaca aggaagagca attcgccttg ttgttaaata     780
aaatttggga tgagcaaact aataaacata aaaatggcga attattgagt acctcttctg     840
ctcgtcaaaa tcaaactgga ttgagttacc cttctgtctc ttttttctctg ctatcacaaa    900 taactccaca tcaacgttgt agcttttacg ctcaggtaat taaaacttgg tacagtgata    960
aaaactttac tctttatgtc actgattata cggaaaatga gcttttttttt ccaatgtctc   1020 cgtatactag ctcctcgaga tggagggggcc cttttggtcg gttttctata aggtgcattt   1080
tatgggatga gcacgacttt tactgccgca actacattaa agaaggtgac tatgtggtta   1140
tgaaaaatgt gcgaaccaaa attgatcacc ttggttatct ggaatgtata cttcatgggg   1200
attcagcaaa acgttataat atgagtatag aaaaagtcga ttcggaagaa cccgaactaa   1260
acgaaattaa gtcacgtaaa aggctttatg ttcagaattg ccaaaatggt atagaagcag   1320
taatcgagaa actcagtcaa agccaacaat cggaaaatcc ttttatcgcc catgaattaa   1380
agcaaacttc tgttaatgaa attacggccc atgtcataaa tgaacctgct agtttaaaat   1440
tgactactat ttctaccata cttcatgcac ctttgcagaa tcttctcaaa ccgaggaaac   1500
ataggctacg cgttcaggtg gtagattttt ggccaaagag tttgacgcag tttgctgtgc   1560
```

```
tatctcaacc accatcttcg tatgtttgga tgtttgcctt gctcgtaagg gatgtatcga    1620
atgtgacttt accggtcata ttttttgatt ctgacgctgc ggaacttatt aacagctcaa    1680
aaatccaacc ttgcaattta gctgatcacc cgcagatgac tcttcagctt aaagaaagat    1740
tatttctgat ttgggggaac ttggaagaac gcattcagca tcacatatcg aagggtgaat    1800
cgccaactct ggctgctgaa gatgttgaaa caccatggtt tgatatatat gtcaaagaat    1860
acattcctgt aattgggaac accaaagacc atcaatcttt gacttttctt cagaagcgct    1920
ggcgaggatt tggcacgaaa attgtttgac tattgtgata caaaacttac aataatgaaa    1980
tgcttacgga aaagaaacat aagaaaaaca atatttaaat ttaaggaaag ctctatattg    2040
ggagaatttt ataaagcgag cgaatttgta ctaaggaaaa acacaga                  2087
```

<210> SEQ ID NO 9
<211> LENGTH: 555
<212> TYPE: PRT
<213> ORGANISM: Schizosaccharomyces pombe

<400> SEQUENCE: 9

```
Met Gly Glu Asp Val Ile Asp Ser Leu Gln Leu Asn Glu Leu Leu Asn
  1               5                  10                  15

Ala Gly Glu Tyr Lys Ile Gly Glu Leu Thr Phe Gln Ser Ile Arg Ser
             20                  25                  30

Ser Gln Glu Leu Gln Lys Lys Asn Thr Ile Val Asn Leu Phe Gly Ile
         35                  40                  45

Val Lys Asp Phe Thr Pro Ser Arg Gln Ser Leu His Gly Thr Lys Asp
     50                  55                  60

Trp Val Thr Thr Val Tyr Leu Trp Asp Pro Thr Cys Asp Thr Ser Ser
 65                  70                  75                  80

Ile Gly Leu Gln Ile His Leu Phe Ser Lys Gly Asn Asp Leu Pro
                 85                  90                  95

Val Ile Lys Gln Val Gly Gln Pro Leu Leu His Gln Ile Thr Leu
            100                 105                 110

Arg Ser Tyr Arg Asp Arg Thr Gln Gly Leu Ser Lys Asp Gln Phe Arg
        115                 120                 125

Tyr Ala Leu Trp Pro Asp Phe Ser Ser Asn Ser Lys Asp Thr Leu Cys
    130                 135                 140

Pro Gln Pro Met Pro Arg Leu Met Lys Thr Gly Asp Lys Glu Glu Gln
145                 150                 155                 160

Phe Ala Leu Leu Leu Asn Lys Ile Trp Asp Glu Gln Thr Asn Lys His
                165                 170                 175

Lys Asn Gly Glu Leu Leu Ser Thr Ser Ser Ala Arg Gln Asn Gln Thr
            180                 185                 190

Gly Leu Ser Tyr Pro Ser Val Ser Phe Ser Leu Leu Ser Gln Ile Thr
        195                 200                 205

Pro His Gln Arg Cys Ser Phe Tyr Ala Gln Val Ile Lys Thr Trp Tyr
    210                 215                 220

Ser Asp Lys Asn Phe Thr Leu Tyr Val Thr Asp Tyr Thr Glu Asn Glu
225                 230                 235                 240

Leu Phe Phe Pro Met Ser Pro Tyr Thr Ser Ser Arg Trp Arg Gly
                245                 250                 255

Pro Phe Gly Arg Phe Ser Ile Arg Cys Ile Leu Trp Asp Glu His Asp
            260                 265                 270

Phe Tyr Cys Arg Asn Tyr Ile Lys Glu Gly Asp Tyr Val Val Met Lys
        275                 280                 285
```

```
Asn Val Arg Thr Lys Ile Asp His Leu Gly Tyr Leu Glu Cys Ile Leu
        290                 295                 300
His Gly Asp Ser Ala Lys Arg Tyr Asn Met Ser Ile Glu Lys Val Asp
305                 310                 315                 320
Ser Glu Glu Pro Glu Leu Asn Glu Ile Lys Ser Arg Lys Arg Leu Tyr
                325                 330                 335
Val Gln Asn Cys Gln Asn Gly Ile Glu Ala Val Ile Glu Lys Leu Ser
            340                 345                 350
Gln Ser Gln Gln Ser Glu Asn Pro Phe Ile Ala His Glu Leu Lys Gln
        355                 360                 365
Thr Ser Val Asn Glu Ile Thr Ala His Val Ile Asn Glu Pro Ala Ser
370                 375                 380
Leu Lys Leu Thr Thr Ile Ser Thr Ile Leu His Ala Pro Leu Gln Asn
385                 390                 395                 400
Leu Leu Lys Pro Arg Lys His Arg Leu Arg Val Gln Val Val Asp Phe
                405                 410                 415
Trp Pro Lys Ser Leu Thr Gln Phe Ala Val Leu Ser Gln Pro Pro Ser
            420                 425                 430
Ser Tyr Val Trp Met Phe Ala Leu Leu Val Arg Asp Val Ser Asn Val
        435                 440                 445
Thr Leu Pro Val Ile Phe Phe Asp Ser Asp Ala Ala Glu Leu Ile Asn
    450                 455                 460
Ser Ser Lys Ile Gln Pro Cys Asn Leu Ala Asp His Pro Gln Met Thr
465                 470                 475                 480
Leu Gln Leu Lys Glu Arg Leu Phe Leu Ile Trp Gly Asn Leu Glu Glu
                485                 490                 495
Arg Ile Gln His His Ile Ser Lys Gly Glu Ser Pro Thr Leu Ala Ala
            500                 505                 510
Glu Asp Val Glu Thr Pro Trp Phe Asp Ile Tyr Val Lys Glu Tyr Ile
        515                 520                 525
Pro Val Ile Gly Asn Thr Lys Asp His Gln Ser Leu Thr Phe Leu Gln
    530                 535                 540
Lys Arg Trp Arg Gly Phe Gly Thr Lys Ile Val
545                 550                 555

<210> SEQ ID NO 10
<211> LENGTH: 1740
<212> TYPE: DNA
<213> ORGANISM: Schizosaccharomyces pombe

<400> SEQUENCE: 10
atgggagagg acgttattga cagtcttcag ttgaatgagt tattaaatgc tggagaatat      60
aagattggag aacttacatt tcagtccatt agaagctctc aagaattaca aaagaagaat     120
actattgtca atttgtttgg aatagtaaaa gattttaccc ctagtcgcca aagtctatat     180
ggaactaagg gtatgcttgc ttatcatggt ggaaactata ctttttattt ttccagtcaa     240
gagctaataa tcatgttttt agattgggta accaccgtat atttgtggga tccaacatgt     300
gatacatcaa gcatcggact acagatacac ttgttcagca acagggaaa tgatttgcct      360 gtaatcaagc aggtggggca accgcttttg cttcatcaaa tcacattaag aagttataga     420
gacaggactc aaggtttgtc taaggatcaa tttcgatatg cactttggcc agacttttct     480
tctaattcca aagatactct ctgtcctcaa ccaatgcctc gtttaatgaa acgggagac     540 aaggaagagc aattcgcctt gttgttaaat aaaatttggg atgagcaaac taataaacat     600
```

-continued

```
aaaaatggcg aattattgag tacctcttct gctcgtcaaa atcaaactgg attgagttac    660
ccttctgtct cttttctct gctatcacaa ataactccac atcaacgttg tagcttttac    720
gctcaggtaa ttaaaacttg gtacagtgat aaaaacttta ctctttatgt cactgattat    780
acggaaaatg agcttttttt tccaatgtct ccgtatacta gctcctcgag atggaggggc    840 cctttttggtc ggttttctat aaggtgcatt ttatgggatg agcacgactt ttactgccgc    900
aactacatta agaaggtga ctatgtggtt atgaaaaatg tgcgaaccaa aattgatcac    960
cttggttatc tggaatgtat acttcatggg gattcagcaa aacgttataa tatgagtata    1020
gaaaaagtcg attcggaaga acccgaacta acgaaaatta agtcacgtaa aaggctttat    1080
gttcagaatt gccaaaatgg tatagaagca gtaatcgaga aactcagtca agccaacaa    1140 tcggaaaatc cttttatcgc ccatgaatta aagcaaactt ctgttaatga aattacggcc    1200
catgtcataa atgaacctgc tagttttaaaa ttgactacta tttctaccat acttcatgca    1260
cctttgcaga atcttctcaa accgaggaaa cataggctac gcgttcaggt ggtagatttt    1320
tggccaaaga gtttgacgca gtttgctgtg ctatctcaac caccatcttc gtatgtttgg    1380
atgtttgcct tgctcgtaag ggatgtatcg aatgtgactt taccggtcat atttttttgat    1440 tctgacgctg cggaacttat taacagctca aaaatccaac cttgcaattt agctgatcac    1500
ccgcagatga ctcttcagct taaagaaaga ttatttctga tttgggggaa cttggaagaa    1560
cgcattcagc atcacatatc gaagggtgaa tcgccaactc tggctgctga agatgttgaa    1620
acaccatggt ttgatatata tgtcaaagaa tacattcctg taattgggaa caccaaagac    1680
catcaatctt tgacttttct tcagaagcgc tggcgaggat ttggcacgaa aattgtttga    1740
```

<210> SEQ ID NO 11
<211> LENGTH: 579
<212> TYPE: PRT
<213> ORGANISM: Schizosaccharomyces pombe

<400> SEQUENCE: 11

```
Met Gly Glu Asp Val Ile Asp Ser Leu Gln Leu Asn Glu Leu Leu Asn
  1               5                  10                  15

Ala Gly Glu Tyr Lys Ile Gly Glu Leu Thr Phe Gln Ser Ile Arg Ser
             20                  25                  30

Ser Gln Glu Leu Gln Lys Lys Asn Thr Ile Val Asn Leu Phe Gly Ile
         35                  40                  45

Val Lys Asp Phe Thr Pro Ser Arg Gln Ser Leu His Gly Thr Lys Gly
     50                  55                  60

Met Leu Ala Tyr His Gly Gly Asn Tyr Thr Phe Tyr Phe Ser Ser Gln
 65                  70                  75                  80

Glu Leu Ile Ile Met Phe Leu Asp Trp Val Thr Thr Val Tyr Leu Trp
                 85                  90                  95

Asp Pro Thr Cys Asp Thr Ser Ser Ile Gly Leu Gln Ile His Leu Phe
            100                 105                 110

Ser Lys Gln Gly Asn Asp Leu Pro Val Ile Lys Gln Val Gly Gln Pro
        115                 120                 125

Leu Leu Leu His Gln Ile Thr Leu Arg Ser Tyr Arg Asp Arg Thr Gln
    130                 135                 140

Gly Leu Ser Lys Asp Gln Phe Arg Tyr Ala Leu Trp Pro Asp Phe Ser
145                 150                 155                 160

Ser Asn Ser Lys Asp Thr Leu Cys Pro Gln Pro Met Pro Arg Leu Met
                165                 170                 175
```

-continued

Lys Thr Gly Asp Lys Glu Glu Gln Phe Ala Leu Leu Leu Asn Lys Ile
            180                 185                 190

Trp Asp Glu Gln Thr Asn Lys His Lys Asn Gly Glu Leu Leu Ser Thr
        195                 200                 205

Ser Ser Ala Arg Gln Asn Gln Thr Gly Leu Ser Tyr Pro Ser Val Ser
    210                 215                 220

Phe Ser Leu Leu Ser Gln Ile Thr Pro His Gln Arg Cys Ser Phe Tyr
225                 230                 235                 240

Ala Gln Val Ile Lys Thr Trp Tyr Ser Asp Lys Asn Phe Thr Leu Tyr
                245                 250                 255

Val Thr Asp Tyr Thr Glu Asn Glu Leu Phe Phe Pro Met Ser Pro Tyr
            260                 265                 270

Thr Ser Ser Ser Arg Trp Arg Gly Pro Phe Gly Arg Phe Ser Ile Arg
        275                 280                 285

Cys Ile Leu Trp Asp Glu His Asp Phe Tyr Cys Arg Asn Tyr Ile Lys
    290                 295                 300

Glu Gly Asp Tyr Val Val Met Lys Asn Val Arg Thr Lys Ile Asp His
305                 310                 315                 320

Leu Gly Tyr Leu Glu Cys Ile Leu His Gly Asp Ser Ala Lys Arg Tyr
                325                 330                 335

Asn Met Ser Ile Glu Lys Val Asp Ser Glu Pro Glu Leu Asn Glu
            340                 345                 350

Ile Lys Ser Arg Lys Arg Leu Tyr Val Gln Asn Cys Gln Asn Gly Ile
        355                 360                 365

Glu Ala Val Ile Glu Lys Leu Ser Gln Ser Gln Ser Glu Asn Pro
    370                 375                 380

Phe Ile Ala His Glu Leu Lys Gln Thr Ser Val Asn Glu Ile Thr Ala
385                 390                 395                 400

His Val Ile Asn Glu Pro Ala Ser Leu Lys Leu Thr Thr Ile Ser Thr
                405                 410                 415

Ile Leu His Ala Pro Leu Gln Asn Leu Leu Lys Pro Arg Lys His Arg
            420                 425                 430

Leu Arg Val Gln Val Val Asp Phe Trp Pro Lys Ser Leu Thr Gln Phe
        435                 440                 445

Ala Val Leu Ser Gln Pro Pro Ser Ser Tyr Val Trp Met Phe Ala Leu
    450                 455                 460

Leu Val Arg Asp Val Ser Asn Val Thr Leu Pro Val Ile Phe Phe Asp
465                 470                 475                 480

Ser Asp Ala Ala Glu Leu Ile Asn Ser Lys Ile Gln Pro Cys Asn
                485                 490                 495

Leu Ala Asp His Pro Gln Met Thr Leu Gln Leu Lys Glu Arg Leu Phe
            500                 505                 510

Leu Ile Trp Gly Asn Leu Glu Glu Arg Ile Gln His His Ile Ser Lys
        515                 520                 525

Gly Glu Ser Pro Thr Leu Ala Ala Glu Asp Val Glu Thr Pro Trp Phe
    530                 535                 540

Asp Ile Tyr Val Lys Glu Tyr Ile Pro Val Ile Gly Asn Thr Lys Asp
545                 550                 555                 560

His Gln Ser Leu Thr Phe Leu Gln Lys Arg Trp Arg Gly Phe Gly Thr
                565                 570                 575

Lys Ile Val

<210> SEQ ID NO 12
<211> LENGTH: 1905
<212> TYPE: DNA
<213> ORGANISM: Homo sapiens

<400> SEQUENCE: 12

```
atgtctttgg ttccagcaac aaattatata tatacacccc tgaatcaact taagggtggt      60
acaattgtca atgtctatgg tgttgtgaag ttctttaagc ccccatatct aagcaaagga     120
actgattatt gctcagttgt aactattgtg gaccagacaa atgtaaaact aacttgcctg     180
ctctttagtg gaaactatga agcccttcca ataatttata aaaatggaga tattgttcgc     240
tttcacaggc tgaagattca agtatataaa aaggagactc agggtatcac cagctctggc     300
tttgcatctt tgacgtttga gggaactttg ggagcccctca tcatacctcg cacttcaagc     360
aagtatttta acttcactac tgaggaccac aaaatggtag aagccttacg tgtttgggca     420
tctactcata tgtcaccgtc ttggacatta ctaaaattgt gtgatgttca gccaatgcag     480
tattttgacc tgacttgtca gctcttgggc aaagcagaag tggacggagc atcatttctt     540
ctaaaggtat gggatggcac caggacacca tttccatctt ggagagtctt aatacaagac     600
cttgttcttg aaggtgattt aagtcacatc catcggctac aaaatctgac aatagacatt     660
ttagtctacg ataaccatgt tcatgtggca agatctctga aggttggaag ctttcttaga     720
atctatagcc ttcataccaa acttcaatca atgaattcag agaatcagac aatgttaagt     780
ttagagtttc atcttcatgg aggtaccagt tacggtcggg gaatcagggt cttgccagaa     840
agtaactctg atgtggatca actgaaaaag gatttagaat ctgcaaattt gacagccaat     900
cagcattcag atgttatctg tcaatcagaa cctgacgaca gctttccaag ctctggatca     960
gtatcattat acgaggtaga aagatgtcaa cagctatctg ctacaatact tacagatcat    1020
cagtatttgg agaggacacc actatgtgcc attttgaaac aaaaagctcc tcaacaatac    1080
cgcatccgag caaaattgag gtcatataag cccagaagac tatttcagtc tgttaaactt    1140
cattgcccta atgtcatttt gctgcaagaa gttccacatg agggcgattt ggatataatt    1200
tttcaggatg gtgcaactaa aaccccagtt gtcaagttac aaaatacatc attatatgat    1260
tcaaaaatct ggaccactaa aaatcaaaaa ggacgaaaag tagcagttca ttttgtgaaa    1320
aataatggta ttctcccgct ttcaaatgaa tgtctacttt tgatagaagg aggtacactc    1380
agtgaaattt gcaaactctc gaacaagttt aatagtgtaa ttcctgtgag atctggccac    1440
gaagacctgg aacttttgga cctttcagca ccatttctta caaggaac aatacatcac    1500
tatggatgta acagtgttc tagtttgaga tccatacaaa atctaaattc cctggttgat    1560
aaaacatcgt ggattccttc ttctgtggca gaagcactgg gtattgtacc cctccaatat    1620
gtgtttgtta tgacctttac acttgatgat ggaacaggag tactagaagc ctatctcatg    1680
gattctgaca aattcttcca gattccagca tcagaagttc tgatggatga tgaccttcag    1740
aaaagtgtgg atatgatcat ggatatgttt tgtcctccag aataaaaaat tgatgcatat    1800
ccgtggttgg aatgcttcat caagtcatac aatgtcacaa atggaacaga taatcaaatt    1860
tgctatcaga ttttttgacac cacagttgca gaagatgtaa tctaa               1905
```

<210> SEQ ID NO 13
<211> LENGTH: 634
<212> TYPE: PRT
<213> ORGANISM: Homo sapiens

<400> SEQUENCE: 13

-continued

```
Met Ser Leu Val Pro Ala Thr Asn Tyr Ile Tyr Thr Pro Leu Asn Gln
 1               5                  10                  15

Leu Lys Gly Gly Thr Ile Val Asn Val Tyr Gly Val Val Lys Phe Phe
                20                  25                  30

Lys Pro Pro Tyr Leu Ser Lys Gly Thr Asp Tyr Cys Ser Val Val Thr
                35                  40                  45

Ile Val Asp Gln Thr Asn Val Lys Leu Thr Cys Leu Leu Phe Ser Gly
         50                  55                  60

Asn Tyr Glu Ala Leu Pro Ile Ile Tyr Lys Asn Gly Asp Ile Val Arg
 65                  70                  75                  80

Phe His Arg Leu Lys Ile Gln Val Tyr Lys Lys Glu Thr Gln Gly Ile
                85                  90                  95

Thr Ser Ser Gly Phe Ala Ser Leu Thr Phe Glu Gly Thr Leu Gly Ala
                100                 105                 110

Pro Ile Ile Pro Arg Thr Ser Ser Lys Tyr Phe Asn Phe Thr Thr Glu
                115                 120                 125

Asp His Lys Met Val Glu Ala Leu Arg Val Trp Ala Ser Thr His Met
                130                 135                 140

Ser Pro Ser Trp Thr Leu Leu Lys Leu Cys Asp Val Gln Pro Met Gln
145                 150                 155                 160

Tyr Phe Asp Leu Thr Cys Gln Leu Leu Gly Lys Ala Glu Val Asp Gly
                165                 170                 175

Ala Ser Phe Leu Leu Lys Val Trp Asp Gly Thr Arg Thr Pro Phe Pro
                180                 185                 190

Ser Trp Arg Val Leu Ile Gln Asp Leu Val Leu Glu Gly Asp Leu Ser
                195                 200                 205

His Ile His Arg Leu Gln Asn Leu Thr Ile Asp Ile Leu Val Tyr Asp
                210                 215                 220

Asn His Val His Val Ala Arg Ser Leu Lys Val Gly Ser Phe Leu Arg
225                 230                 235                 240

Ile Tyr Ser Leu His Thr Lys Leu Gln Ser Met Asn Ser Glu Asn Gln
                245                 250                 255

Thr Met Leu Ser Leu Glu Phe His Leu His Gly Gly Thr Ser Tyr Gly
                260                 265                 270

Arg Gly Ile Arg Val Leu Pro Glu Ser Asn Ser Asp Val Asp Gln Leu
                275                 280                 285

Lys Lys Asp Leu Glu Ser Ala Asn Leu Thr Ala Asn Gln His Ser Asp
                290                 295                 300

Val Ile Cys Gln Ser Glu Pro Asp Ser Phe Pro Ser Ser Gly Ser
305                 310                 315                 320

Val Ser Leu Tyr Glu Val Glu Arg Cys Gln Gln Leu Ser Ala Thr Ile
                325                 330                 335

Leu Thr Asp His Gln Tyr Leu Glu Arg Thr Pro Leu Cys Ala Ile Leu
                340                 345                 350

Lys Gln Lys Ala Pro Gln Gln Tyr Arg Ile Arg Ala Lys Leu Arg Ser
                355                 360                 365

Tyr Lys Pro Arg Arg Leu Phe Gln Ser Val Lys Leu His Cys Pro Lys
                370                 375                 380

Cys His Leu Leu Gln Glu Val Pro His Glu Gly Asp Leu Asp Ile Ile
385                 390                 395                 400

Phe Gln Asp Gly Ala Thr Lys Thr Pro Val Val Lys Leu Gln Asn Thr
                405                 410                 415

Ser Leu Tyr Asp Ser Lys Ile Trp Thr Thr Lys Asn Gln Lys Gly Arg
```

```
                420             425              430
Lys Val Ala Val His Phe Val Lys Asn Asn Gly Ile Leu Pro Leu Ser
            435                 440                 445
Asn Glu Cys Leu Leu Leu Ile Glu Gly Gly Thr Leu Ser Glu Ile Cys
        450                 455                 460
Lys Leu Ser Asn Lys Phe Asn Ser Val Ile Pro Val Arg Ser Gly His
465                 470                 475                 480
Glu Asp Leu Glu Leu Leu Asp Leu Ser Ala Pro Phe Leu Ile Gln Gly
                485                 490                 495
Thr Ile His His Tyr Gly Cys Lys Gln Cys Ser Ser Leu Arg Ser Ile
            500                 505                 510
Gln Asn Leu Asn Ser Leu Val Asp Lys Thr Ser Trp Ile Pro Ser Ser
        515                 520                 525
Val Ala Glu Ala Leu Gly Ile Val Pro Leu Gln Tyr Val Phe Val Met
    530                 535                 540
Thr Phe Thr Leu Asp Asp Gly Thr Gly Val Leu Glu Ala Tyr Leu Met
545                 550                 555                 560
Asp Ser Asp Lys Phe Phe Gln Ile Pro Ala Ser Glu Val Leu Met Asp
                565                 570                 575
Asp Asp Leu Gln Lys Ser Val Asp Met Ile Met Asp Met Phe Cys Pro
            580                 585                 590
Pro Gly Ile Lys Ile Asp Ala Tyr Pro Trp Leu Glu Cys Phe Ile Lys
        595                 600                 605
Ser Tyr Asn Val Thr Asn Gly Thr Asp Asn Gln Ile Cys Tyr Gln Ile
    610                 615                 620
Phe Asp Thr Thr Val Ala Glu Asp Val Ile
625                 630

<210> SEQ ID NO 14
<211> LENGTH: 1298
<212> TYPE: DNA
<213> ORGANISM: Homo sapiens

<400> SEQUENCE: 14
atgtctttgg ttccagcaac aaattatata tatacacccc tgaatcaact taagggtggt      60
acaattgtca atgtctatgg tgttgtgaag ttctttaagc ccccatatct aagcaaagga     120
actgattatt gctcagttgt aactattgtg gaccagacaa atgtaaaact aacttgcctg     180
ctctttagtg gaaactatga agcccttcca ataatttata aaaatggaga tattgttcgc     240
tttcacaggc tgaagattca gtatataaaa aaggagactc agggtatcac cagctctggc     300
tttgcatctt tgacgtttga gggaactttg ggagccccta tcatacctcg cacttcaagc     360
aagtatttta acttcactac tgaggaccac aaaatggtag aagccttacg tgtttgggca     420
tctactcata tgtcaccgtc ttggacatta ctaaaattgt gtgatgttca gccaatgcag     480
tattttgacc tgacttgtca gctcttgggc aaagcagaag tggacggagc atcatttctt     540
ctaaaggtat gggatggcac caggacacca tttccatctt ggagagtctt aatacaagac     600
cttgttcttg aaggtgattt aagtcacatc catcggctac aaaatctgac aatagacatt     660
ttagtctacg ataaccatgt tcatgtggca agatctctga aggttggaag ctttcttaga     720
atctatagcc ttcataccaa acttcaatca atgaattcag agaatcagac aatgttaagt     780
ttagagtttc atcttcatgg aggtaccagt tacggtcggg gaatcagggt cttgccagaa     840
agtaactctg atgtggatca actgaaaaag gatttagaat ctgcaaattt gacagccaat     900
```

```
cagcattcag atgttatctg tcaatcagaa cctgacgaca gctttccaaa tggagtctcg      960
cttcgtcctc caggctggag ttcagtggca cggtctcggc tcattgcagc ctccacctcc     1020
tgagttcaag cttctcctgc ctcagcctcc caagtagctg ggattacagg ctctggatca     1080
gtatcattat acgaggtaga aagatgtcaa cagctatctg ctacaatact tacagatcat     1140
cagtatttgg agaggacacc actatgtgcc attttgaaac aaaaagctcc tcaacaatac     1200
cgcatccgag caaaattgag gtcatataag cccagaagac tatttcagtc tgttaaactt     1260
cattgcccta aatgtcattt gctgcaagaa gttccaca                             1298
```

<210> SEQ ID NO 15
<211> LENGTH: 340
<212> TYPE: PRT
<213> ORGANISM: Homo sapiens

<400> SEQUENCE: 15

```
Met Ser Leu Val Pro Ala Thr Asn Tyr Ile Tyr Thr Pro Leu Asn Gln
  1               5                  10                  15

Leu Lys Gly Gly Thr Ile Val Asn Val Tyr Gly Val Val Lys Phe Phe
             20                  25                  30

Lys Pro Pro Tyr Leu Ser Lys Gly Thr Asp Tyr Cys Ser Val Val Thr
         35                  40                  45

Ile Val Asp Gln Thr Asn Val Lys Leu Thr Cys Leu Leu Phe Ser Gly
     50                  55                  60

Asn Tyr Glu Ala Leu Pro Ile Ile Tyr Lys Asn Gly Asp Ile Val Arg
 65                  70                  75                  80

Phe His Arg Leu Lys Ile Gln Val Tyr Lys Lys Glu Thr Gln Gly Ile
                 85                  90                  95

Thr Ser Ser Gly Phe Ala Ser Leu Thr Phe Glu Gly Thr Leu Gly Ala
            100                 105                 110

Pro Ile Ile Pro Arg Thr Ser Ser Lys Tyr Phe Asn Phe Thr Thr Glu
        115                 120                 125

Asp His Lys Met Val Glu Ala Leu Arg Val Trp Ala Ser Thr His Met
    130                 135                 140

Ser Pro Ser Trp Thr Leu Leu Lys Leu Cys Asp Val Gln Pro Met Gln
145                 150                 155                 160

Tyr Phe Asp Leu Thr Cys Gln Leu Leu Gly Lys Ala Glu Val Asp Gly
                165                 170                 175

Ala Ser Phe Leu Leu Lys Val Trp Asp Gly Thr Arg Thr Pro Phe Pro
            180                 185                 190

Ser Trp Arg Val Leu Ile Gln Asp Leu Val Leu Glu Gly Asp Leu Ser
        195                 200                 205

His Ile His Arg Leu Gln Asn Leu Thr Ile Asp Ile Leu Val Tyr Asp
    210                 215                 220

Asn His Val His Val Ala Arg Ser Leu Lys Val Gly Ser Phe Leu Arg
225                 230                 235                 240

Ile Tyr Ser Leu His Thr Lys Leu Gln Ser Met Asn Ser Glu Asn Gln
                245                 250                 255

Thr Met Leu Ser Leu Glu Phe His Leu His Gly Gly Thr Ser Tyr Gly
            260                 265                 270

Arg Gly Ile Arg Val Leu Pro Glu Ser Asn Ser Asp Val Asp Gln Leu
        275                 280                 285

Lys Lys Asp Leu Glu Ser Ala Asn Leu Thr Ala Asn Gln His Ser Asp
    290                 295                 300
```

```
Val Ile Cys Gln Ser Glu Pro Asp Asp Ser Phe Pro Asn Gly Val Ser
305                 310                 315                 320

Leu Arg Pro Pro Gly Trp Ser Ser Val Ala Arg Ser Arg Leu Ile Ala
            325                 330                 335

Ala Ser Thr Ser
            340

<210> SEQ ID NO 16
<211> LENGTH: 1816
<212> TYPE: DNA
<213> ORGANISM: Homo sapiens

<400> SEQUENCE: 16
atgtctttgg ttccagcaac aaattatata tatacacccc tgaatcaact taagggtggt      60
acaattgtca atgtctatgg tgttgtgaag ttctttaagc ccccatatct aagcaaagga     120
actgattatt gctcagttgt aactattgtg gaccagacaa atgtaaaact aacttgcctg     180
ctctttagtg gaaactatga agcccttcca ataatttata aaaatggaga tattgttcgc     240
tttcacaggc tgaagattca agtatataaa aaggagactc agggtatcac cagctctggc     300
tttgcatctt tgacgtttga gggaactttg ggagccccta tcatacctcg cacttcaagc     360
aagtatttta acttcactac tgaggaccac aaaatggtag aagccttacg tgtttgggca     420
tctactcata tgtcaccgtc ttggacatta ctaaaattgt gtgatgttca gccaatgcag     480
tattttgacc tgacttgtca gctcttgggc aaagcagaag tggacggagc atcatttctt     540
ctaaaggtat gggatggcac caggacacca tttccatctt ggagagtctt aatacaagac     600
cttgttcttg aaggtgattt aagtcacatc catcggctac aaaatctgac aatagacatt     660
ttagtctacg ataaccatgt tcatgtggca agatctctga aggttggaag ctttcttaga     720
atctatagcc ttcataccaa acttcaatca atgaattcag agaatcagac aatgttaagt     780
ttagagtttc atcttcatgg aggtaccagt tacggtcggg aatcagggt cttgccagaa      840 agtaactctg atgtggatca actgaaaaag gatttagaat ctgcaaattt gacagccaat     900
cagcattcag atgttatctg tcaatcagaa cctgacgaca gctttccaag ctctggatca     960
gtatcattat acgaggtaga aagatgtcaa cagctatctg ctacaatact tacagatcat    1020
cagtatttgg agaggacacc actatgtgcc atttttgaaac aaaaagctcc tcaacaatac    1080
cgcatccgag caaaattgag gtcatataag cccagaagac tatttcagtc tgttaaactt    1140
cattgcccta atgtcatttt gctgcaagaa gttccacatg agggcgattt ggatataatt    1200
tttcaggatg gtgcaactaa aaccccagat gtcaagctac aaaatacatc attatatgat    1260
tcaaaaatct ggaccactaa aaatcaaaaa ggacgaaaag tagcagttca ttttgtgaaa    1320
aataatggta ttctcccgct ttcaaatgaa tgtctacttt tgatagaagg aggtacactc    1380
agtgaaattt gcaaactctc gaacaagttt aatagtgtaa ttcctgtgag atctggccac    1440
gaagacctgg aacttttgga cctttcagca ccatttctta tacaaggaac aatacatcac    1500
tatggcactg gtattgtac ccctccaata tgtgtttgtt atgaccttta cacttgatga     1560
tggaacagga gtactagaag cctatctcat ggattctgac aaattcttcc agattccagc    1620
atcagaagtt ctgatggatg atgaccttca gaaaagtgtg gatatgatca tggatatgtt    1680
ttgtcctcca ggaataaaaa ttgatgcata tccgtggttg gaatgcttca tcaagtcata    1740
caatgtcaca aatggaacag ataatcaaat ttgctatcag attttgaca ccacagttgc      1800 agaagatgta atctaa                                                    1816
```

```
<210> SEQ ID NO 17
<211> LENGTH: 518
<212> TYPE: PRT
<213> ORGANISM: Homo sapiens

<400> SEQUENCE: 17

Met Ser Leu Val Pro Ala Thr Asn Tyr Ile Tyr Thr Pro Leu Asn Gln
  1               5                  10                  15

Leu Lys Gly Gly Thr Ile Val Asn Val Tyr Gly Val Val Lys Phe Phe
                 20                  25                  30

Lys Pro Pro Tyr Leu Ser Lys Gly Thr Asp Tyr Cys Ser Val Val Thr
             35                  40                  45

Ile Val Asp Gln Thr Asn Val Lys Leu Thr Cys Leu Leu Phe Ser Gly
         50                  55                  60

Asn Tyr Glu Ala Leu Pro Ile Ile Tyr Lys Asn Gly Asp Ile Val Arg
 65                  70                  75                  80

Phe His Arg Leu Lys Ile Gln Val Tyr Lys Glu Thr Gln Gly Ile
                 85                  90                  95

Thr Ser Ser Gly Phe Ala Ser Leu Thr Phe Glu Gly Thr Leu Gly Ala
                100                 105                 110

Pro Ile Ile Pro Arg Thr Ser Ser Lys Tyr Phe Asn Phe Thr Thr Glu
            115                 120                 125

Asp His Lys Met Val Glu Ala Leu Arg Val Trp Ala Ser Thr His Met
        130                 135                 140

Ser Pro Ser Trp Thr Leu Leu Lys Leu Cys Asp Val Gln Pro Met Gln
145                 150                 155                 160

Tyr Phe Asp Leu Thr Cys Gln Leu Leu Gly Lys Ala Glu Val Asp Gly
                165                 170                 175

Ala Ser Phe Leu Leu Lys Val Trp Asp Gly Thr Arg Thr Pro Phe Pro
                180                 185                 190

Ser Trp Arg Val Leu Ile Gln Asp Leu Val Leu Glu Gly Asp Leu Ser
            195                 200                 205

His Ile His Arg Leu Gln Asn Leu Thr Ile Asp Ile Leu Val Tyr Asp
        210                 215                 220

Asn His Val His Val Ala Arg Ser Leu Lys Val Gly Ser Phe Leu Arg
225                 230                 235                 240

Ile Tyr Ser Leu His Thr Lys Leu Gln Ser Met Asn Ser Glu Asn Gln
                245                 250                 255

Thr Met Leu Ser Leu Glu Phe His Leu His Gly Gly Thr Ser Tyr Gly
                260                 265                 270

Arg Gly Ile Arg Val Leu Pro Glu Ser Asn Ser Asp Val Asp Gln Leu
            275                 280                 285

Lys Lys Asp Leu Glu Ser Ala Asn Leu Thr Ala Asn Gln His Ser Asp
        290                 295                 300

Val Ile Cys Gln Ser Glu Pro Asp Asp Ser Phe Pro Ser Ser Gly Ser
305                 310                 315                 320

Val Ser Leu Tyr Glu Val Glu Arg Cys Gln Gln Leu Ser Ala Thr Ile
                325                 330                 335

Leu Thr Asp His Gln Tyr Leu Glu Arg Thr Pro Leu Cys Ala Ile Leu
                340                 345                 350

Lys Gln Lys Ala Pro Gln Gln Tyr Arg Ile Arg Ala Lys Leu Arg Ser
            355                 360                 365

Tyr Lys Pro Arg Arg Leu Phe Gln Ser Val Lys Leu His Cys Pro Lys
        370                 375                 380
```

```
Cys His Leu Leu Gln Glu Val Pro His Glu Gly Asp Leu Asp Ile Ile
385                 390                 395                 400

Phe Gln Asp Gly Ala Thr Lys Thr Pro Asp Val Lys Leu Gln Asn Thr
            405                 410                 415

Ser Leu Tyr Asp Ser Lys Ile Trp Thr Thr Lys Asn Gln Lys Gly Arg
            420                 425                 430

Lys Val Ala Val His Phe Val Lys Asn Asn Gly Ile Leu Pro Leu Ser
            435                 440                 445

Asn Glu Cys Leu Leu Leu Ile Glu Gly Gly Thr Leu Ser Glu Ile Cys
            450                 455                 460

Lys Leu Ser Asn Lys Phe Asn Ser Val Ile Pro Val Arg Ser Gly His
465                 470                 475                 480

Glu Asp Leu Glu Leu Leu Asp Leu Ser Ala Pro Phe Leu Ile Gln Gly
            485                 490                 495

Thr Ile His His Tyr Gly Thr Gly Tyr Cys Thr Pro Pro Ile Cys Val
            500                 505                 510

Cys Tyr Asp Leu Tyr Thr
        515

<210> SEQ ID NO 18
<211> LENGTH: 27377
<212> TYPE: DNA
<213> ORGANISM: Homo sapiens

<400> SEQUENCE: 18
gatctttttt tctgggctaa ttcatatgac tcaaattcat tatagttgca taataataat      60
gttatgcttt tttcattttt catttaatag atgttgagat cgttaccagt tttttgctct     120
tacaaataat actttaataa acatccttga atatatgtac ttccatgttt ttacttctcc     180
acaataaact aaaagtgagg tcgatgtatc taaggttatg cattttttt aatagatgct      240 gccagattat ttaccaaagg tcatagaaat ttatatccaa atagcagtgt aggagaatat     300
actttactca caccttcaca gtattggaag ttaacactat atgtaatttt tgacagttaa     360
gcaggtgaaa ggtgttttct tacttaattt tcctggctac ttggaaactt gaaaatctta     420
ctatatattt acaaacgttt ttaattccct cttcctcaga ttttctgctc ttactcttta     480
tctgattttc tgttgaatta tattttttgtc agtttgtggg caaccatgta tgttttacac    540
attttcttat ttgactactt ttatggtttc tgccattatt tccatctcat gttgtaatgg     600
ccaatattaa ttactaaatt agatttattg aaattatacc atgccagctt gagatgtcca     660
ttcaagtcct cttgacttgg attttttatac cacttattag caatattgag gatatgtttg    720
tgtatgatgc tttataaaat aaattataaa aacataatgt actgttatgt ataatagaat    780
gtaagctaaa gtgattacaa aatacacatt tttaaagtct taagttcttc tttttagaaa    840
gcattttgta accttagtgc tatgactact acttttgctt tcttgttaga gtaaaatcct     900
atttttgatg ttcatttggt cattctatta aatttcataa gtttactatt ttatccatct     960 ccgctttat ttcctctaca ctgtattttt tcaacatgat aaaaactttc atacatggta    1020
gaattaaaac agttgtacaa tgaatactca ataactacc agctagactc tccaataact    1080
attttacttt gtgtgctctg tcacgtgtat ttatttctac atatctcttt ttttttttt    1140 ttttcttttg agatggagtc tcgcttcgtc ctccaggctg gagttcagtg cacggtctc    1200 ggctcattgc agcctccacc tcctgagttc aagcttctcc tgcctcagcc tcccaagtag   1260
ctgggattac aggtgcccac caccacgccc agctaatttt tgtattttta gtagagacac   1320
```

-continued

```
agtttcacca tgttggccag gctggtctcg aactcctgac cttagataat ctgcccgcct   1380
cggcctccta aagtgctggg attacaggtg caagccaccg tgcctggcct atgtgcctct   1440
tcattcatta atttatattt tttatacatt tcaaagtaag ttgcagacat aagtacattt   1500
tctaaacact gtggtatgaa cataattagc tagagtttag tagttattta gagttttta   1560 tttttgaggt aaaattagca gtgaaatgga caactttcca ttttatgaac cactccatga   1620
gttttgacta atacataaac gtgtaaccca atccctcta gatttgctgt tctagaactt   1680
tgaaaaaatt gaatcatatg tactcttttt gtatatacta tatgttttg agagttaatc   1740 acattgttgc atatatcatt agtttgtttc cttttaatg cctagtcaca tgatatgcgg   1800
tagacatttt ttctttagat aggaatttct agttgttatg acatcatttg tttccttttt   1860
cctattagat ggcttcaatg tctttgtcaa aaatcaagcg agtataaatg tgggcttatg   1920
tctaggcttc ccattcaatg cttactagta tagtgtgaag tatgcatttt cctcacacta   1980
aattttcagt tattgcagca ccatttgcat tctccttgca ttgctttgct gctttagtaa   2040
aaaatcaaaa tacaatgtaa atgtgggttt atttccaggc tctctattta atttaattca   2100
gttgatctat ttttcaatcc tgatgccagt accgtgttgt cttaaattac tgtaagttta   2160
tagtaagtct tgaagtcatg tacatggttc tccaactttg ttattttta aaatgttatt   2220 taatattcta gattttctgc acttccacat aagtgatagc atctgctttg caatctctac   2280
aataaagcct ctgctatttg tttgtttgtt gttgttttga gcagagtct cattctgttg   2340 cccaggctgg agtgcaatgg cacaatctca gctcactgca gcctccacct cctgggttca   2400
agtgattctc atgcctcagc ctgctgagta gctgggatta caggcatctg caccacactt   2460
ggctaatttt tgtatttgta gtagagatgg ggtttcacca ttttggccag gctggtctct   2520
aactcctgat ctcaagtgat ctgcccacct cagtcctccg aagtgttggg attataggcg   2580
tgagccactg tgcccacccc agcctctgct attttcgaag gattatgctg aatttacaga   2640
ttaatttgga gagaattgat atcttaacaa tattgagcct tctaaatcat gaatgtggca   2700
tatctcacca tttatttata ttttcttcag tttctctcag caacgctcca ttgttttcag   2760
ttctacaatg aagttgtaat ggacttaatt ttttgcctt ttcctttta taggctctgg   2820 atcagtatca ttatacgagg tagaaagatg tcaacagcta tctgctacaa gtaagactat   2880
gtatcatttt tgagatgggc acagtaatga gcataataaa gtctgcctct acacttacca   2940
gctaatccat ttctttctaa tagtagaaca catatccttt aaagctaaaa tatgtccata   3000
tttaactttc ttcttctacc gtgtcttgtt ggcataaaat ggaacccata agataacgt   3060 gtctttacat tgcatatttt aagtcatcta tctctaacag acttaatgtt taaaacagat   3120
atgttttaaa cattaaatac atgatgtatt tgaagtcatg tatctctgtt agagttacat   3180
gacttaaaat gtgcaatgta aagacacata tctttaaact attacatgaa gagttatcct   3240
gtcacatgat gcatttaaca gtgtaccata aaggagctcc ttgcaatatg cctcaaaatt   3300
ttaatttaat gttagtaatg atagtgtgtc tatcaagtac cctccttctg ctacatcagc   3360
taagattaaa aaaaatttt cagaaaaata tttttaacca caaatttatt aaatgtgcta   3420
ttgtaaaaat tttaatttct caaattggag aaggaagata acaaatgtga atggaagaag   3480
gattgatgaa atctttaat gttgtgttgt aattggaggt accattatgt actcatgttt   3540
tctaggtaaa tacagaagtc gatgtagctg tgtgtatgta tgatacgcat atattcacac   3600
gtgtacacat ttgtttatat tataggggtg tgtgtgtgtg tgtgtgtgtc agtatgaatg   3660
```

-continued

```
tgtgttcata tgtaccctat ctctctctcc atgaaaaagc atagaggcag cagcactcca    3720
gttgccataa gcacacctgg tgctcagatc ttggtttata aataatattt ctctctaaag    3780
gaatcagagc tccttggtga acagcagat ttctgaacta aacaaggga attacaagat     3840 tagtatggag taaccttgta ctagaaagta aggggttct cagttaatga tgaaactcgt    3900
caaatggctt aggatagaac atgtctagga acatttgagc atcaaaacaa ataatactaa    3960
ttgagtaaag caggaatgca tgagcccatg ttgatgatga taaaggaaaa ataaaatata    4020
tggggttaag tggaaatatc tttcttaaag taaaataaca aatataaaag ggataatgaa    4080
attagaaaaa aaaagctac cattttgtaa ccatgatagt cattgttgag ttagttgtga    4140
atctgtggat tctaaactat caggatattt gatgaaaaat aagatattta cattttctct    4200
agtatattct tgttaaatac aaggggggaaa cagtaagttt ttagtagaga agtgattgga   4260
cactaccttt accagctgaa taaagtttag gtctacagta atagaaacac tcactttgta    4320 tgcccttga tgtgatgcac tgagaagcat acagtatcac ttacgcatta ttcctgccaa    4380
aaatgcataa gctaaatctg agcctgagga ataaccagac aacacccaaa ttggtgttta    4440
ttctacagaa taaatggctg tactcttcaa atatatcagt gttgtgaaag ataaagaaaa    4500
gccgaggact tattttacat taaagaagtc taaagagaca tgagaattaa atgtgataca    4560
tggtccagaa ttggatctta gacttgaaaa taaaatgaat gctaagaaga acattttgag    4620
gacaattgta gaaatttgag taatgtttgt taattaattc gattatagta ataaatcagt    4680
taaatgttct aatgttgaaa attgcctgta attatgtcaa taaaatgtct tcttttgaaa    4740
tacatactgg aggatttaga ggaaaggagg cataatgtct ggtagttatt ctcaaatgat    4800
tcaataatat ttatgtggtg agagacagat aaagacaggc acagtgacaa tgataaatgt    4860
gcaaaaatgt taacaattgg tgaatcttgg tgaatattat acagaaggtc tttgtattgt    4920
ttttgcaatt ttccttaagt ttgaaagcat tttaaaatga aaagttaaaa actttaggtt    4980
aaaatatgag tttgaagcaa ttgctcttat cactgtgtag caatgtacac taaattgatc    5040
aggtctgcca atggccttt ttttttttt tttttttttg aggcggagtc tcgctgtcgc    5100
ccaggctgga gtgcagtggc actatcttgg ctcactgcaa gctctgcctt ccgggttcac    5160
gccattctcc tgcctcagcc tcccgagtag ctgggactac aggtgcccgc caccacaccg    5220
gctaattttt tgtattttta gtagagacgg ggtttcaccg tgttagccag gatggtctcg    5280
ctctcttgac ctcgtgatct acccgcctcg gcctcccaaa gtgctgggat tacaggcgtg    5340
agccaccgcg cccggtgcca atggcctttt taaaagcatc accagctggg tgcagtggct    5400
cacgcccgta atcccagcac tttgggaggc cgaggcgggc agatcacctg aggacgggag    5460
ttcgaagcca gcctgaccaa catggagaaa ccccgtttct actagaagta caaaaattag    5520
ctgggcgtgg tggtgcatgc ctgtaatccc agctacttag gaggctgagg caggagaatc    5580
gcttgaacct gggaggtaga ggttgtggtg agcagagatc gcaccattgc actccagcct    5640
gggcaacaag agggaaactc cgtctccgaa aaaaaaaaa aaaaccaca atcgccacca     5700 caacaaaatg ttccactgta ataaatgttc cactctgatg taataaatgt tccactctga    5760
taaaggcaag tgagaaataa taaatgatga atatatttgg gcagactcat ttgtcacaga    5820
agtatcttaa atataaactt tattaactga aatatttgaa aagaggtgta attacttgaa    5880
atatctaatt aagtgataca gagagccttg ttggtaaact tctgtccttc ttggccatt     5940 gctccttgaa ggaaaactaa ttcaacaaga atttcattgg attaaagctc agtactgaaa    6000
ggaattgtct tcgccattga ggttaataag atttgtacat catttcccctt ttctaaaaca   6060
```

```
catgaaagtg ttaagctaga atgtatagca agctgttgcc ttaagctaag ggtcaccagc   6120
aattttatac ttttcccag  taaaaactga tcactacaat cccaggccat ctttccacaa   6180
gtagctgagg agacctattg tacctatttc ccaggcaatt gctcctaatg cttttgtctg   6240
agttttttt  ccagtttgac tcaacttcct cttatttttc ctctccctcc tcctccactc   6300
cctccttcca actccccaaa cttcctcttc tccactacta caccactcct gtgacagtta   6360
gatcacccctt aatgtccctt cctattctta atctgatttt ataatgatgg ttctgtaaaa   6420
agtaactgat tgaaacatc  caagagcctg caaataatat ttgcaaataa tattttacaa   6480
gtgtgttttg ttacattctt ttgtggcaga caccagttag aacttaaacg gttgcctagc   6540
gtaatatttt cttagctaaa taaaccttgc ttttttgaat gcttactagg cagttaagtt   6600
acttatttct tcccccaaat tatccagcgt ttatttagta cacatttgtt gagtacctac   6660
tgtgcctggc actatgctag tgggccttgg gtatacatca gggaataaag acataaccct   6720
tcctttcatg gagtgacact taatagagct taaattaatt agattttata gtatatattt   6780
ggttcaggag gatgcatgtc ataaatatga ttcttgttat tctgattgaa tataaaaatt   6840
cttttacagta cttacagatc atcagtattt ggagaggaca ccactatgtg ccattttgaa   6900
acaaaaagct cctcaacaat accgcatccg agcaaaattg aggtcatata agcccagaag   6960
actatttcag tctgttaaac ttcattgccc taaatgtcat ttgctgtgag tattttccat   7020
aataaaacaa acgttttcat attatttgtg tgtatatgta cacatatgta taattttgtg   7080
tcttaggaat aagtaaattg ttaatatata tattatatttt tgcaagaatg gtaaattttt   7140
taggtaaagt gctaaattct tagagaataa attattctga tagtaataaa agtgggtgct   7200
attttcagat ctaaaattca gcttagtcac tctgataaag gcaaatgaga aataataaat   7260
gatgaatata tttgggcaga ctcatttgtc acagaagtat cttctgaaat ataaaccttt   7320
attaactgaa attttgaaa  ggagttgtaa ttacttgaaa tatctaatta agtgataaag   7380
agagccttgt tggtaaactt ctgtcctgct taataactag aatataataa atataattta   7440
aatttctttt agtaattgag aatttctcag tgcctttact ctgaacatca gtgattatat   7500
aaatatgtaa taaatgtata taactgtttt gtaatccttt tactacataa tcggctcaag   7560
acatattctg aaaatcattt ttaaaagctc ctcatctttt tgcaatttgc ctacttttcc   7620
tctgaatatc taaaatgatg ttttggaaaa tgtagataat tgatggttat atgcatttgg   7680
atgccctaaa ttgagtcttc actaaaaatgt gctacaatgt gtaaatatct atgtacatcg   7740
ccatgtattt gtgtgcttat aaattgtgag tatctgtgtt cattaatata catatatttt   7800
ccaatccaaa atttgggttt gtttgaagaa attttttatt ttaaaatctc tttaaataaa   7860
atgtgaggga actgttttta cccatttgag cttgaaatgg tggttgggat taaaatgtat   7920
atataaggat tttagataat tcttcaaata ttatcaaact ttggtttatt gaattttgta   7980
aaatcataca gctttgtaaa ataaaaccac tctccgcgat cattttttaa acaaataagg   8040
atattatctc agaaattaac ggaaactgtc taaagttaca cagttaactg gcaacagaac   8100
cagaagaaag ccatacacct tttgattcca aatgatgcca tttctgctac atggtaccta   8160
accatatgac ttcttaaaat tattaattat taaacagaat tggaaatatt attagtttag   8220
aagtgcccctt ctccctaagt gtggtaagtg gatatttaac tggagtgaag acggggccac   8280
tgcattttt  tctcctactg ggaaatttag cattctttac agaggagaaa aaaattgatg   8340
ctagaaataa ttatgagtaa cttttgtatca caaaaccagg catagaaatc actggtagtt   8400
```

-continued

```
aatgtaaata tgatttggat atacttaccc acaaaatatc aaataattat ctattgaaaa    8460
aaagttattt gttctgcaaa gtgaattatc tccataattt acataattta agaaaaagta    8520
actgactcat ctacatgtaa gaatgatact ttttaatttg ataacttgtt aaatggaaat    8580
cttcacgctt acaccaaaat cgatttctat catttcattg ccaataattt taggcaagaa    8640
gttccacatg agggcgattt ggatataatt tttcaggatg gtgcaactaa aaccccagat    8700
gtcaagctac aaaatacatc attatatgat tcaaaaatct ggaccactaa aaatcaaaaa    8760
ggacgaaaag tagcagttca ttttgtgaaa aataatggta ttctcccgct ttcaaatgaa    8820
tgtctacttt tgatagaagg taagatattt aagtcactgt tttgttagaa tactccttt    8880 gcatatttt cctaattaat tattgtttaa tacattttac agacaaccta gtacatataa     8940
agtaaaaata gtatttaaat ttaacaaaat tgaatatata tgttaactag gttcaaatat    9000
atataagcac acgttcataa atttatctta attacatttg aaattgtact tcagactcaa    9060
gtgttaacat ttaactatat tgttggattg cattttattt tgtcaatgct aagctgattg    9120
tctagttaag taataataaa agaggctgat tgcttatgta ccattgctgt tttcttggcc    9180
tctggatgtc actgttgttt catagaaata gggtgaaagt catctattgt atcaaaatca    9240
aagaagagac cattgaaaca gtaaagata acttgacaag ttttaaatga aatttatcat     9300
gtttggtttt tcattttctt ttcattttca tctaattttt atctcattta tctaaaatat    9360
gtactgtgaa ttttttttca tggcaaattt agagttttc ttaaggcttc tcttcccttg     9420
taaccttttc attgtttttc ttaaggctttt ccttcccttg aaacctttttc attgtttttc   9480 ttaaggcttt ccttcccttg aaacctttttc attgttttc tgaaggcttt tcttcccttg    9540
aaaccttttg taatagaaga aaaataccttt ctttaatttg ccttagagta atatttaact   9600 ttattttaa taaatgaggg aattctatgt aaattataga ctttgggtga ttatgtgtca     9660
gtataggttc attttaaca aatgtaccac gctggtagag gatgttgata ctggaggagg     9720
ctagcatgta tggtagaagg ggatacggaa aatctctgta ccttcctctt aatttgctg     9780 tgaacctaaa actgctcctt aaaaaaaaaa aaatgaagt cttaaaaaga aacatagaa      9840 tgtacaacac tgagagtaaa ccctaatata gactggactt tgagtgataa tggtttgtta   9900
gtaatgtaaa gtgtggactt tgagtgataa tggtttgtta ctaatgtaaa ctgtggactt    9960
tgagtgataa tggtttttta aaataggttt cttgattgac taaatttacc actctggtgc   10020
aagatgttga taatggggaa gaggctaggg gacataggga aactttgtac cttttgctta   10080
attttgcagt gaacctaaaa ctgctttta aaaaggctt atttaaaaaa ataatgagaa     10140
tgtatgtaaa agcactttga aatgtaaaag gaatataaga aatgtgagct atttttattt   10200
tatgtttcta agtattataa cctggaccaa gggctaggat cttactgcag tatggcactg   10260
ctctggttag gaagtaacaa aatcaaaaac tgacctggac ttagagatga accaaagaaa   10320
acgatataaa tacaaagtca ttcttagact ttaaggacct gcagcagtat tcactgatat   10380
tcatgccaag ttaatgcagt tgacactatt ttattgtgac catagtttac attagggttc   10440
actcattctg ctttacagtt ctttatgttt tgacaaatgc agaataccat gtacccacca   10500
ttagagtctc atataaaaca gtatcactta atttctgtaa aagctctaag atctgtgtcc   10560 agatttttt ttgcatgcag atgtccagtt ttccagtacc atttcttaaa aagactgttc    10620
cttctccatt gaattgcctt tgcttctttg tcaaccagt tgtgtgaat ttgcttctgt      10680 gttctctatt ctgttttaat ctgtctgtta ttttcctaat atcacaccat ccttatttct   10740
aaagctatat agtaattctt gaaattgtgt agtgtttgtc ctgcaacttt cttctttttc   10800
```

```
ttgagtattg tgttggctat tgtaaatctt ttgcatttcc atgtaaactt tataatcagt    10860
ttgtcaatat ccaaaaataa cttgctggga tttttattaa gattgccagc tgggcgcagt    10920
ggctcactct ggtaatctta gcactttggg aggccgaggc aggcagatca cctgaggtcg    10980
ggagttcgag accagcctga ccaacatgaa gaaaccctgt ctctactaaa aatacaaaat    11040
tagccaggca tcatggtgca tacctgtaat cccaactact cgggaggctg aggcagtaga    11100
atggcttgaa cccgggaggc ggaggttgcg gtgagccgag atcgcgccat tgcactccag    11160
cctgggtaac aagagcgaaa cttcatctca aaaaaaaaa agattgccat aatctataag    11220
tcacggtgga gacagagaac taacaacttg atgttattga cgatgaacat ggactatctt    11280
tctatgtaga tcttcttaga tcccttta ac tagggtttta tagttttact cagataaacc    11340
ttataaatcc aacaaaatat agatcacatt ttgttagctt tatatctaag tattttcttt    11400
tttggtgcta attatttaat gttaaattca actttgatt atttattgct tatgtatagg    11460
gaagcaattg atttttttt taattaacct tgtatcctct accgttgcta taattgcttg    11520
ttatttcagg aattttttg ttgtgatttc ctgtaaacaa agacagctta tttcttcctt    11580
cctaatatgt atacctttg tttccttttc ttactgcatt agatagggct tccagtacaa    11640
tattgaatag gagcaatgag agggaatgtt cttgctttta tcccagtctt aggtggaaag    11700
tgtcaccatt aaatgtaatt ttagctgtgg ctatttatc gatgttcttt atcaagttga    11760
agaagttccc caatattcct agtttgctga gaatttttat tattaatgat gttggatttt    11820
atcaaatgct tttctattg catctattaa tatgatcata caattttct tctttagcct    11880 attaatgtga taaattacat taattgattt tgaggtgttt aaccagcctt gcctacctaa    11940
aataaatctc atttggtcat ggtgaataat tattttcttt tttgattcaa tttttaaata    12000
ctttctgagt attttttat gtgttttctt aagagaagtt gatcaatagg tcttcattct    12060
tgtaatgtat ttggttatgt attagaatat tgctggcctc ataagagtta ggaaacattc    12120
cctctacttc cattttctgg aatacatagt agagaattag tgtcatttca gtgtttgggt    12180
agacttagct attgaaacaa tctgagcctg gtgactttt tcaagattat tattattgat    12240
ttaatttctc tatagacata gacctattca gattatctgt ttctccttgt gtgagttttg    12300
atagattatg cctttcaaga aatggaacca ttttatctaa ggtgtcaaac ttgtgggttc    12360
gaattgttta taatatttat ttattattaa cactatattt taaactgcat aacatttaac    12420
ttcctctgaa acattttgta ttgttttccaa ttgaattgaa tccaatttgt atggaactct    12480
aatgtcactg aatcatttta tcataatatt tattattaat acctataatt tactgaatag    12540
actatgtgtc aggcactgta ctagtttagt atttttatctt taactctcat aacagttctt    12600
ctgtaagctg gatatatccc ctttgtaaac agaagaggaa actgagacca agagaaaatg    12660
gtgaagtact caaggttaaa gacttaataa atgtcagaaa aaaattcaaa cttaggcctt    12720
tctgtctcca tagtccatgt taaatatttc tactgattgc aaataaattg ctctcagtta    12780
ggatgtctcc agatacaaac cttgagaaat gtagtatgca catatataca tgtaaatgtc    12840
tttctttgtt cttattcatt tgtttagcac atgtttattg aatgcctact atgtgccaga    12900
cactgattta ggcattagtg gcaatgtagc aaacacaaca aagttcttcc tttcatggac    12960
tttacattaa gaggaaatca ctaaaatatt gatagtaata gtcactcatg gctctaagtg    13020
ctttacaaat attaactcat ttaatctttta taatgatctt acagagtaac attattctca    13080
gttttgcaaa tggggaaact gttataccag agtttaagta acttgaccaa ggttgtccag    13140
```

```
cttatgtgcc agagccaaac tcgtgtgact ggccagtgtg aatgactaga tgagctctca    13200
ccagattctt tgaaatagtg tttttgggga ggaactcata gagaaaagag ttagtgaatg    13260
gtcacctatt gcagttttga acagtaggca ggagtctctt cagcagggct aggtatcagt    13320
ctccaaaaga tagactaact tttgggctgt gaaacttttta agtagcatgc ttagggaata    13380
ttgttttgag ttttttaagca tgcataatga gagtttctat ctagctgcaa tatgatatag    13440
cagaactctg gcttccagta acaaagagct tgggggaagg aggatgggaa cagggcaagt    13500
taaaatgcca cagagctcac cgttcttgcc aaaattcagc ccttttttctg gagcaaacac    13560 tccttggatt gttgaaggcc tctggtaatt tccagaattc taaaaaaggt tttacagttt    13620
ttgccaatat tcttactgct gttatagtca agtgtgtctt tggatgtcct cactctgcta    13680
taccagaagt gcttctcctt tataattgaa tgttgacatt acaaattcta cccaaatttt    13740
aggaaataca cagaggtatt ttttaaatcc ttttcatttt gcctggagag aggaagcatt    13800
attagctaag taaaaaggac actgccttct aataatggat gccattggac aatacttctc    13860
agccagcctg gtcatttgaa tgcttactct gtcatagaat taactgtgat aattttccca    13920
ggaaaaatga acaaatttta tatgtgaatt catattacat gaactactca tatctatatt    13980
taaatgaaat attgacctga aaattgagat ttaaactcta aatttgccca gatattaatt    14040
agtatatagc aaattagtga gaatctgatc ataacttagc ttttaattta tattccctct    14100
tttggttatt tgaaccaaag tgttcctgaa ataaagagca atttgtttaa atttaagaag    14160
ttggttaaaa tttcacaagc tttatatttt accaaagtct cagcattttt gtgcattgat    14220
ttttttaatc aatgtatagg attgtacatt tacaaattaa tatttttttac atacattcat    14280 tgtctttttc tgtcaattcc tttagtcttt tattatacct cacacgttat ttaataggac    14340
tgtacttgtc tacattttat ttgcactact tgaaggattt atttattctc ttaacaggag    14400
gtacactcag tgaaatttgc aaactctcga acaagtttaa tagtgtaatt cctgtgagat    14460
ctggccacga agacctggaa cttttggacc tttcagcacc atttcttata caaggaacaa    14520
tacatcacta tgggtatttt gttttgtttt gttttgtttt gttttgttta ttatactttt    14580
aagttctggg gtcatgtgct gaacatggag gtttgttacg taggtataca cgtgctattg    14640
tggtttgctg cacccatcaa cccgtcacct gcattaggca tttctcctaa tgctgtcctt    14700
cccctagcct cccacccccct gacaggccct ggtgtgtgat gttcccctcc ctgtctccat    14760
gtgttctcat tgttcaactc ccacttatga gtgagaacat gcagtgtttg gttttctgtt    14820
ctggtgttag tttgctgaga atgatggttt ccggctttat ccatatgcct ggcaaggaca    14880
tgaactcatc ctttttttgg ctgcatagta ttccatggtg cgtatgtgcc acattttctt    14940
aatccagtct atcactgatg gacatttggt atagttccag gtctttgcta ttgtgaatag    15000
tgctgcaata aacgtacatg tgcatgtgtc tttatagcag aatgatttat aatcctttgg    15060
gtatataccc agtaatggga ttgctggatc aaatggtatt tctagttcta gatccttgag    15120
gagttgccat accgtgttcc acaaagattg aactaattta cactcccacc aacagtgtaa    15180
aagcattcct gtttctccac attgtctcaa gcatctgttg tttcctgact ttttaatgat    15240
cgccattcta agtggcgtga gatggtatct cattgtggtt ttgatttgca tttctctaat    15300
gatcagtgac attgagcttt cttttcatatg tttgttggcgt gtgtaaatgt ctccttttaa    15360
gaactgtctg ttcatatcct tcacccactt tttgatgggg ttgttttttt cttttaaatt    15420
taagttcttt gtagagtcta gatattagcc ctttgtcaga tggattgcaa aaatttcctc    15480
ccattctgta ggttgcctgt ttactctgat gatagtttct tttgccgtgc agaagctctt    15540
```

```
tagtttaatt aggtcccatt tgtcaattt ggctttatt gcctttgctt ttggtgtttt    15600
agacatgaag tctttgccca tgcctatgtc ctgaatggta ttgcccaggt ttccttctag    15660
gattttatg gttttaggtc ttacatttaa gtctttaatc catcttgagt tgattttgt     15720
ataaggtgta aggggatcca gtttcagttt tctgcatatg gctagccagt tttcccaaca    15780
tttattaaat agggaatcct ttccccattg cttgttttg tcaggtttgt caaagatcag     15840
atggttgcag atgtgtggtg gtgttttcaa ctgagaaaac ttttggaatt aaaaactgtt    15900
gaagagtaat ttttattagt ttatttcatt ggttactata tgttcagcat gaacttacag    15960
tgtatcaact tatatgtact aggttttct ggcatatatc tgttcttttg ataagcatat     16020
atagtgagag tacacgcaat gtgtgaggca taaggctgct gtcttttgat tcctcagcca    16080
gaggctggta ctcacttgtt ttctttaaca gtgaggattt agattccagt tacagagaaa    16140
aattcagagc tgcaaaccta gtaaaaatta agtgattcaa tttcagaatt tctgagccac    16200
taaattacaa atttgctgcc actgaaaatt ggaatataaa agaattcatt aggagctata    16260
aacagatttc tacatttaga aggagggggt agggataaaa tctcctctac tgcttgatga    16320
aacaatcacc ctggacacat tctgatttga gaaaccttgg attataacat atgttttatc    16380
atcctattcc tctttctttc cgacttctac atttgtagca attagtagtc attgtcataa    16440
tgtgtaaatc ctgattgaaa aattatatac tggttgaaaa atattatacg gtaagcatga    16500
tacctcccta attgtgtggt aaagtcactg ttaggcattg ccctctgtcc ttccaacata    16560
tcataaaatt ttagccataa agcgaaagtg tatgccactg acttaaatct ctgtgttata    16620
gctgttttta ctgatatact cagtgtctaa ttctccctct cattagactc atgatctgag    16680
agtccatctt ttttgaaaat aaaatgattt ttaattaagc caattaatta aaaaattaaa    16740
actcataaaa ttcagttttt cttgtataat aagtcactga gctttctctt tttgcatgct    16800
catcctcgct cacttgcttt tgttctttcc cctttctctc tattttgcct tgccagtact    16860
gggcaccgtg acgcgtctaa accaggaaag gaaatattca tattcatttt aaactctgaa    16920
atactactac ttcttttact agaagtctca aaaaaattac cttaaggacc ccatttttt     16980
tttttttttt gagatgaagt cttgctctat tgcccagata ggagtgcagt ggcatgatct    17040
cagctcactg caacctctgc ctccccggtt caagcgattc tcctgtctca ccccccgc     17100
cgagtagctg ggactacagg catgcaccac taacacccgg ctgattgttt cgtattgtta    17160
ttagaaacga ggtttcacca tgttggccag gctggttttg acctcctgac cttaggtgat    17220
ctgcccacct cggcctccca aagtgctggg attacaggtg tgagccactg tgcccaacca    17280
aggctgttga cttttactg gttgcttcaa aactaaggca aatgctgttc acactccaga    17340
ttttaagaca ttttacatt ttttattact tgagtttcat catcaaaagc cagtatatct     17400
tttaattgat tcttctttt attttggggt tatgaaataa ttttaactta tagaaaaatt    17460
aaaaagtaa catcacaaca attacgtatc caccatttag atttaacaaa tcgtaacgtt     17520
ttgacattat ttcagacttt ttttttttt tttttttttg gagacagtgt cattctgata    17580
cccaggctga agtggcatga tttcagctca ttgtagcctt gacatcctgg gctcaagcaa    17640
tcctactatc tcagcctccc aactagctgg gactacaggt gcacaccacc acacctggct    17700
aattttgta gggatggggt tttgccatgt tgcccaggct gttcttgaac tctggagttc    17760
aagcaatctg cctaccttgg cctccaaact ttttttttt tttttttttt ttattttaa     17820
gaaattaaat gttacagaga agtagtataa tgccatatca atcccttctc taactctttt    17880
```

```
ttctcagagg tagctacttt tccaaacttg gattaaatcc ttctcatcaa tgttttatg    17940
ccttcattat atgtgtgaac tcttaagcag tatggcatat ttttcatttt ttaaatttat    18000
ataaactgtt tcgtactatg ccaagccttt tgcagcttgc ttttttttgat tcattaaaat   18060
tttcaagatt taccactatt gacgcatgta gatttagatt atttaacatc tttggagtat   18120
gttatgaaat atcagaattt attagcctat tttcctatta atggatatgt gttattttt    18180
gtttcattta cagaccataa tgaagtcacg ttatatgttt tcttgtctat ttcccttgtc   18240
ataaaatgag ttcagtgggt cataaacagt ttttttttaa attatatgat gtggttgtag   18300
taaaaatgg aatgagaggg aatggataat agagaacatt ttacacagta agggtcagtg    18360
ttgtttccta aactttcatt tcaattgtat gtgtatgtat gtattactaa gatatgatat   18420
taaatgaatt tcttactgtg agtccttaac aaaaatgttt gaaagttact cctaaggtgt   18480
ttacctgaaa ttagaattac tggattataa ggtgtatata agttttgctt tatgggaaga   18540
aataccaaat tgttcttccc atggttttaa caatatatgg tcccatcagt aatgtataaa   18600
atttagttt ctaccaagtt cactccaaca cttggtatta gtctatttct gtctgatact    18660
tggcattaat tttgtaattt tgtcaggcca gcgagcatca gatggtatcc ataatgtttt   18720
tatttgtatt tcctagatgt ctagtgtgtt taagcagccc ccgtgtttat cagctacata   18780
ggttccctac tctatgaatt ccatgttcac atcttttgcc tgttttttcta tgtggttact  18840
gatttctttg ttggttcatg tgtgagcgca catacatgta attgattgta aggtttcttt   18900
ccgtgttaga gatactaatc tttgtcagtt tcatccatac ttctagtgta ttccatgcct   18960
ttttaacttt atggtttctt gtgttttata ggttttttta aaattttgt ttggtaattg    19020
ctttataggt tactctcatc cctttgcttt caagtttctg gcattctaat ttgtatgtca   19080
ctcataaata aaagcttatg gctaaatttt agttttaata gtggagttta aatatgttct   19140
taagttattg atatatttag tttatgtttc taatttttc tgtttcccct ttcactgctt    19200
tggaagtaag tagttctgta tttaattttg acttaatatc cttaattttt aatttttata  19260
ctaactttaa taatgtctaa tgctaatcaa tatcgtagtc ttttcttag gcaataatat   19320
tcttttgtta aattgacatc ttttattaga aagaaacac ctatatattt aataaataga   19380
agggtataag atgtaatgtg gttaccctct tgttttcctc aaagtgcaaa tgaaaacaaa    19440
ttgcatggac ctttcgaact tttattttta ttcaagtata tcttttcaag tatattttct   19500
tatcaacatc tcataaacat tatgatgatg cataataaaa aataaattac tcatagttaa   19560
aatatgttgg tattcaagta aagcaaaata actgtactac acaatgcaca actttagtgt   19620
attgtgtagt cttagattta tatacatttc aaaagttaac tatggaatta ggcatcataa   19680
actacaaacc tctggatatg tgcttactaa aaatattaat tatctagaat cttgcatgtt   19740
gtgactgttt agtaattttt ctctattggc catatttatt aacactttga atttattaag   19800
atattactta cagaggccag gtatggtggc tcacacctgt aatcccagta ctttgggagg   19860
ccaaggcagg cagatggctt gagctcagga gttgagacca gcctgggcat tgtggcaaga   19920
ccctgtctct ataaaattac aaaaatcacc caggcatggt ggtgtgcaac tgtggttcta   19980
gctacttgga aggctgaggt gggaggctca cttgagccca ggaggcagag gtgacagtgc   20040
ctgggtgaca gagtgagacc ttgtcttaaa aaatatatat atatagatat agatatagat   20100
atagatatag atcatagaat cagagaattc ttagagatga tcattttctt caacttttca   20160
ttttaacaaa taaggaaatt gagagcaaaa ttaattaatg atttgaccct ggaaccgagc   20220
accctgttct caatttagag ttgtttattc tgaatcttat actgtctttt ttattgccct   20280
```

```
tatgtaataa gcttactctt tcataattct cttgtgaaac aaacaagcac attacaatat    20340
aggggatgca gtattcttct gtttaataat ttatatttta aaactacaca tgtttgagca    20400
gtaaaaagtt ataacaaaca agctaaatta ttttttaaata tttatggttc tttcttttat    20460
aaatttcaga tgtaaacagt gttctagttt gagatccata caaaatctaa attccctggt    20520
tgataaaaca tcgtggattc cttcttctgt ggcagaaggt tagctaaatt tccatgccct    20580
gcaattttaa ctgtttgttt acaaggttat ttcacctact tatatttcag tatacctgaa    20640
agtatacctg ttccttcttt gtatacttat tccttcctct gtaagataaa cagactttgt    20700
aaatttaaag atatctgcca agccttcctt tagtctgtat ttcttcaagc aggcaccgtc    20760
acatactttc ccctatgcct tactatttg ttttcctcc tcagtaagca ttccacttta    20820
ccagtgcttt tctcagaatt tggcattcag agctggacat tgtgctgcag atgttgtttg    20880
gccaattcag aatagagtga aattattatt tacctgaaac tggacactca gcttctacta    20940
gcctgaaatg tcattgtata gctatttatt tgtacacttg gttttgtttt ctttcctttt    21000
tgatacagcc atctcatgtt ttatttgtgg tccagtgaaa tcctagggtc ctgtcacatg    21060
aacttcttga acttggtctt ctcattctat tcttaatgta attttttttt ctgtcacatg    21120
aacttcttga acttggtctc ttcgttctat tcttaatgta atatctttgt ttttatggtt    21180
cctgggagta ggtgctaagt tcatctttct tagttttagt tcacagtttt aacctattga    21240 gacctttga agcctaaaat tcagttcccc tgtattaatg tctgttgtat gccctagttc    21300
atgtctgtat gtcctaattt attcttactt tccctgttaa ttagttatac tgtttaaata    21360
tgggttccac agataaaagc taataaaaca ttctataaat tgagtatctt ccatttccaa    21420
acaagaagat atttatctta acctgtgaat tttcattta cccagtatgt ctaatttctt    21480
atttcttcct tatcttacca aattattaaa tctcagattc tgacattctt gtccattcaa    21540
ccagatgata tcccttttttt cttttttaaa gttataaatt attcccctag cttataaatag    21600 aaaggagaga ggcatgctaa aacggtattt aactgcatgc tattttttag aatattctgt    21660
attttaattt tatctttcat aaaactaaca tgcaatgagt tacatttcat gaatcacttt    21720
ttgtggtttc tatggaggct atcaactgtt tttttatttt attttattttt atttattttg    21780 agacagagcc ttactctgtc gcccaggctg gagtgcagtg gtgcaatctc gactcactgc    21840
aacctctgcc tcccaggttc aagcaattct catgcctcag cctccagagg agctggaatt    21900
acaggtgtat gttaccaagc ctagctattt ttttggtat ttttagtaga gacagggttt    21960
catcatgttg gccaggctgg tcttgaactc ctcaagatcc gcccaggtga tctgcccacc    22020
tcagcctccc aaagtgctga gaatacaggt gtgagggtgt caacttatttt taaatacgtt    22080 aatatttaat caaaagatt aaattgctta tcataagata ttctccctat gtaggtatag    22140
tgaaatattc caaatgaat ctgctaaatg agcttaatta taggttgagt atctgtggag    22200
ttaaaaacac aaactgtcct ctgctctgcc accacagcaa tcagcgcaga agacttatgt    22260
gaccaaatgc ataggggttt tcacccacac accaagcagg caatccctca gcagacgcca    22320
gctgggtgtc ctccagttca attctgacac tatctacctg gagataatgc caagttttc    22380 tttgtatctt gagttatttt agtaaataaa atttacaggt ctatactatc ataaaacaat    22440
tttaacttta ccttgataat aaggaatagc agactcatat ggtttgatct ttttttcctt    22500
cactagcact gggtattgta cccctccaat atgtgtttgt tatgaccttt acacttgatg    22560
atggaacagg agtactagaa gcctatctca tggattctgt aagtatcaga ggtaataaag    22620
```

```
atatttttaa ttaaaaaata atatttaaaa aattgaatac atttattcat acctgctttg    22680
ttcctaaaag gacttaaggc accttaaaaa tataagtaaa atatgagcac ataaatcttg    22740
aatcatctgt gtatgtatct ctttttttat ttgacactaa atcttaacat ttgaatagtg    22800
aaaaattaag gaacagggat ttaaagagtc attccctata ccatggccaa aatgcagaga    22860
tacggccaca ctatggaagc attatttgta gtcaacattt tatcgtactt ttgtttgttt    22920
gtttgtttgt ttgtttgttt tttgagatgg agtcttgctc tgttgcccag gctggagtgc    22980
agtggcacga tctcagctca ctgcaacctc cgcctcccgg gttcaagcag ttctctgcct    23040
cagcctccca gtagctggga ttgcaggta tgcaccacca cgcccagcta attttttgtat    23100 ttttgtagag acagggtttc accatcttgg ccaggctggt cttgaactcc tgacctcatg    23160
atccacccac ccttggcctc ccaaagtgct gagattacag gcgtgagcca ccgtgcccag    23220
ccttgatcat acttttttaaa cctccacatt tcatattaga ggaatgaagt tactttaaca    23280
gggaagatag atattattgt ataaagtttt gaggcagtct acaaaacctt cctcatttct    23340
gacactaatt gcaattggaa gtcctcaagg ccactcttag atttgataat tcacaagact    23400
cctagaactc actgaaaact gttatactga cagttacaga ttattacagc taaaggatgt    23460
acattaaaat cagataatga aagagatgta taggacagag tccaggaaag ttccagacat    23520
ggaacttata gttgtcctct ccccatagag ttgtggactg ttactttccc tgcaacagtg    23580
tgtagcagta tacataatat attgccagat agggaagctc tgctaaaaga ttttagtggg    23640
actctatcac gtaggtatgg ttgactgccc atatggctga tcatagtctt cagcccctct    23700
tgagatcaag ctgataccac atgctccaaa ctttccaccc tacatcatat tgttaaacta    23760
ttcatagtga cccagggctt ccaggcaaaa atacttctat caagtgtgac atagaaaggg    23820
cttagagatt acgttccaca agctaaggtc aaagcccaga cctctcttag ggtaaagtta    23880
aaatgtttac tacatggatt ggaaaagatc tgagttatag ttgagaggag aattttttctc    23940 ccacctacac aattcatttta accttcatt aaatatttaa tgagcacctg ctatgtacta    24000
ggtactatcc tatgtgatgg agacacagcg gtgaacaaag taaacaaaat tccttccttc    24060
ttgaaactta taacatagta gggaagagaa aaattaaata actatataat acatatactg    24120
tatgttatat tcatttaagc ttagcacaag atttttttttt ctatgcacaa agagaatagt    24180
cagcctcatt gtttttaaat cattattacc atcatcatta ttaaatcaga gcaatttact    24240
tgattacgtg tatctcaaag ctattttaag attaaagagt aaataagatt ttggagttga    24300
gaccagcatt ctagtttatg aattctacaa tcttgataga gggaaactgt ctagattatc    24360
ttttaattgg acaatattga aatatgtgtt aataataaca ttaaaaagga ttaatatatt    24420
ttcctttttt tttctctcat gaaacatttt taaggacaaa ttcttccaga ttccagcatc    24480
agaagttctg atggatgatg accttcagaa aagtgtggat atgatcatgg atatgttttg    24540
tcctccagga ataaaaattg gtaggcaaga atattttaac aatcccacac ttctttttact    24600 tgagatagca ctaacatata tgtactctgt ggacttttag aagtctgaaa gctttgcttc    24660
caaatgattt actaagtagt gagtgattac tctatgatca acctttgatg aagagagtgg    24720
cagggataaa atagttatga atcataattc ctgcagtcaa aagatttttta aaatattttt    24780 aaatatagga aagggagata gttttgatca caagcacatt tgacattgtc atgctacaag    24840 catttagtt gaaattagac caaaagtgat gaattgttgg cagtaaacat tttctgtaac    24900
aaactccaat tatccaattt aattcatgga ttaattttt tatttattgt taactagttt    24960
cagattttac aagcttttgt tttaccaatt ttttgtgagc tttgttttct gcataaacat    25020
```

```
ttgattaata aaccagatct tcctcatttc aaattgtact gcttatacct gctgccactg    25080
aattttcctt ctgtgactat atttgtactt atgttgaaac ttgcagatct aagtcatatt    25140
aagacaattt tgatttttct aacaattttt tatcgtagga aattttacca gctgcagatt    25200
tagcagctgg tttattttt atatactatt tttaatcagg ctttactctc cctggtcaat     25260
ctttgcatct tataatagtt acataatgat aggaatttgt gttgatctct aaccaagttt    25320
aacttgaata cctttatttg ttgtcagttt taatttgtgt taactgtttg gattcttttg    25380
gatagatttc tagaagtaag tctttatatc caaaagcatg ggcctggtag acccattgta    25440
accactattt tagattttta aaatatatac caaccatttt gaaacccaag atgtactcac    25500
tgttacctgc ttgtggcaaa aaattcaaat tagtcacaat tgctccaaaa caataacatg    25560
aatctagtat gtattttgaa gagagaataa tgttaaattt ggaagggacg tttacttact    25620
tttcaagcca aaataaatgt taattttct agctcagtgg taagcttagg tacctatttc     25680
agagttattt attttgtttt aatggttaaa tcgctttttt tgttttttgtt tttgtagatg   25740 catatccgtg gttggaatgc ttcatcaagt catacaatgt cacaaatgga acagataatc    25800
aaatttgcta tcagattttt gacaccacag ttgcagaaga tgtaatctaa tattgccatc    25860
caatttagca tacataaaat gttgccactc accttccctg tttgagcttc ttttcctgac    25920
ctgagttttg tatcagcaat gttgatgatg ttagcatggg tatgggatta gaaaatgtcc    25980
ttaccttaaa tctcttggct tttactgggt gcaaggtaaa taatggctat ggattttgtt    26040
ttgctttctg ttttgctttt gtacaaagag acctgcttaa acaagtactg ctgagataag    26100
tgtctgatca agctacagtg tactttaagt agaaatggca aagttgcttt gttggggtgc    26160
tgatactgat gattttagga taaattcatt tctttaaact tgtaatacat ggttttattg    26220
cttgtttctc tccaggatag tagagatttc tctatttcac ctcaacctaa taaaagtggt    26280
cagatttata atgttaatga cttaatatta tccttttcta atagtctcat gtaaaatatg    26340
ccgctattac aacttacaac taattgaatg agatgttaac ttagtaaaat agtttgattt    26400
ttacctgaca gtgtttgtca aatttaaaat catgaatatt caattttata caaacattta    26460
tatatatata tatagatttg tgtatgttat ttgccaaaga cagatataaa ttacctggtt    26520
taatattagt gaagaataaa taagtgcaca catttcaact gtttcattta tttgccctaa    26580
gttgagctga aaaatgatat gaggcaaaga atcgaaatag gtgtggcaat gcagcagatg    26640
tttagggctg tctacatccc aggtactgtg ctaagcacta acatgtatt tgatcctcac      26700 agcaacctat ttttccgata agaaatctga ggcttgattg ataagctgac ttgactaagt    26760
tcacacagtt tgtaaaagct agagtctgtg ccttaattca cataatctct attcagagcc    26820
tgtactgtta accactcaag gattctggaa cagaagctaa cagttttctg caacgagtct    26880
ttgacttaaa catctgaaat aacattggaa atagattata agaggagtca gtgtgttttt    26940
ctatagtttc aaaatacttt taacatctta ttgtcaaaaa gattggataa ctgactttct    27000
ttgctcataa taactctaaa ttctagttcc tgagtacatt aacacatctt ctttacctaa    27060
ctaccaatgt cccccatcat cgacttatca gcttgtttga gacaatgaga aagactgatt    27120
ttattttcaa gaatatagac tcttggttca aaacattttc aggaaaaata ttttaaaacc    27180
ctacagttga acaggtgtgt ttccgtgttg atgatgtgct caggatacaa aggtgaaata    27240 aacattttt ctgccttcag gaagccctca atctagaaga gtagaggtcc aaaggtgcca     27300
tatgttcaca ctgtgagcct gcaagatctc cacgttaaca aaggaaaact cttcctatga    27360
```

```
atcttcatga tgatagg                                                    27377
```

<210> SEQ ID NO 19
<211> LENGTH: 30
<212> TYPE: DNA
<213> ORGANISM: Homo sapiens

<400> SEQUENCE: 19

```
ccctaacccT aaccctaacc ctaaccctaa                                         30
```

<210> SEQ ID NO 20
<211> LENGTH: 30
<212> TYPE: DNA
<213> ORGANISM: Homo sapiens

<400> SEQUENCE: 20

```
ttagggttag ggttagggtt agggttaggg                                         30
```

<210> SEQ ID NO 21
<211> LENGTH: 60
<212> TYPE: DNA
<213> ORGANISM: Homo sapiens

<400> SEQUENCE: 21

```
ccctaacccT aaccctaacc ctaaccctaa ttagggttag ggttagggtt agggttaggg        60
```

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Telomeric
      primer PBoli82

<400> SEQUENCE: 22

```
tgtggtgtgt gggtgtgc                                                      18
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 23

```
ggttacggtt acaggttaca                                                    20
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 24

```
cggttacacg gttacaggt                                                     19
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
      SpPot1p-binding oligonucleotide

```
<400> SEQUENCE: 25
gttacaggtt acggttacgg                                                    20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 26
tgtggtgtgt gggtgtgcgg tt                                                 22

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 27
ggttacacgg ttacaggtta caggttacag                                         30

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 28
ggttacacgg ttacaggtta caggttacag ggttacggtt acg                          43

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 29
ctgtaagcat atcatcattc gaggttac                                           28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 30
ggttacgcat atcatcattc gaatctcg                                           28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence:
      SpPot1p-binding oligonucleotide
```

-continued

```
<400> SEQUENCE: 31
ctgtaagcat atcatcggtt acggttac                                           28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 32
ggttacggtt accatcattc gaatctcg                                           28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 33
ctgtaagcat atggttactc gaatctcg                                           28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 34
ctgtaagcgg ttacggttac gaatctcg                                           28

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
      SpPot1p-binding oligonucleotide

<400> SEQUENCE: 35
ggttacaggt tacaggttac                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:
      hPot1p-binding oligonucleotide

<400> SEQUENCE: 36
ttagggttag ggttagggtt                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:
      hPot1p-binding oligonucleotide

<400> SEQUENCE: 37
```

-continued

```
ggttagggtt agggttaggg                                              20

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:
      hPot1p-binding oligonucleotide

<400> SEQUENCE: 38
ttagggttag ggttagggtt agggttaggg                                   30

<210> SEQ ID NO 39
<211> LENGTH: 45
<212> TYPE: PRT
<213> ORGANISM: Schizosaccharomyces pombe

<400> SEQUENCE: 39

Met Gly Glu Asp Val Ile Asp Ser Leu Gln Leu Asn Glu Leu Leu Asn
 1               5                  10                  15

Ala Gly Glu Tyr Lys Ile Gly Val Arg Tyr Gln Trp Ile Tyr Ile Cys
            20                  25                  30

Phe Ala Asn Asn Glu Lys Gly Thr Tyr Ile Ser Val His
        35                  40                  45

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: C-strand
      binding specificity of SpPot1p

<400> SEQUENCE: 40
cgtaaccgta accctgtaac ctgtaacctg taaccgtgta acc                    43

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: PBoli109
      oligonucleotide

<400> SEQUENCE: 41
ccgtaagcat ttcattattg gaattcgagc tcgttttcga                        40

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: PBoli164T
      oligonucleotide

<400> SEQUENCE: 42
ttcagatgtt atctgtcaat cagaacctg                                    29

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: PBoli194B
```

```
                                oligonucleotide

<400> SEQUENCE: 43
gaacactgtt tacatccata gtgatgtatt gttcc                              35

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 44
tgaaggtcgg agtcaacgga tttggt                                        26

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 45
catgtgggcc atgaggtcca ccac                                          24
```